(12) United States Patent
Lee et al.

(10) Patent No.: US 11,992,504 B2
(45) Date of Patent: *May 28, 2024

(54) CELL-MEDIATED TRANSIENT DELIVERY OF IMMUNE-ENHANCING MOLECULES INTO THE TUMOR MICROENVIRONMENT

(71) Applicant: ImmunityBio, Inc., Culver City, CA (US)

(72) Inventors: John H. Lee, San Diego, CA (US); Laurent H. Boissel, San Diego, CA (US); Hans G. Klingemann, San Diego, CA (US)

(73) Assignee: ImmunityBio, Inc., Culver City, CA (US)

( * ) Notice: Subject to any disclaimer, the term of this patent is extended or adjusted under 35 U.S.C. 154(b) by 206 days.

This patent is subject to a terminal disclaimer.

(21) Appl. No.: 16/953,879

(22) Filed: Nov. 20, 2020

(65) Prior Publication Data

US 2021/0145879 A1    May 20, 2021

Related U.S. Application Data

(60) Provisional application No. 62/938,201, filed on Nov. 20, 2019.

(51) Int. Cl.
| | | |
|---|---|---|
| *A61K 35/17* | (2015.01) | |
| *C07K 14/735* | (2006.01) | |
| *C07K 16/28* | (2006.01) | |
| *C12N 5/0783* | (2010.01) | |
| *A61K 39/00* | (2006.01) | |

(52) U.S. Cl.
CPC ........ *A61K 35/17* (2013.01); *C07K 14/70535* (2013.01); *C07K 16/2827* (2013.01); *C12N 5/0646* (2013.01)

(58) Field of Classification Search
None
See application file for complete search history.

(56) References Cited

U.S. PATENT DOCUMENTS

| | | | |
|---|---|---|---|
| 7,618,817 B2 | 11/2009 | Campbell | |
| 8,017,755 B2* | 9/2011 | Liu | C12N 15/1086 435/320.1 |
| 8,034,332 B2 | 10/2011 | Klingemann | |
| 8,313,943 B2 | 11/2012 | Campbell | |
| 9,150,636 B2* | 10/2015 | Campbell | C07K 16/28 |
| 9,181,322 B2 | 11/2015 | Campbell | |
| 10,138,462 B2 | 11/2018 | Klingemann | |
| 10,456,420 B2* | 10/2019 | Lee | A61P 35/02 |
| 10,763,921 B1* | 9/2020 | Kerselaers | H04B 5/0012 |
| 10,774,310 B2* | 9/2020 | Klingemann | A61K 48/00 |
| 10,801,013 B2* | 10/2020 | Klingemann | C07K 14/55 |
| 10,960,024 B2* | 3/2021 | Klingemann | C07K 14/7051 |
| 11,000,550 B2* | 5/2021 | Lee | C07K 16/32 |
| 11,058,723 B2* | 7/2021 | Klingemann | C12N 15/625 |
| 11,129,850 B2* | 9/2021 | Klingemann | C07K 14/7158 |
| 11,207,350 B2* | 12/2021 | Lee | A61P 35/02 |
| 11,230,699 B2* | 1/2022 | Lee | C07K 14/71 |
| 11,547,727 B2* | 1/2023 | Boissel | C07K 16/1063 |
| 2017/0129967 A1 | 5/2017 | Wels et al. | |
| 2017/0304364 A1 | 10/2017 | Lee et al. | |

FOREIGN PATENT DOCUMENTS

| | | |
|---|---|---|
| EP | 3 406 631 A1 | 11/2018 |
| KR | 10-2018-0008862 A | 1/2018 |
| WO | 2016/138491 A1 | 9/2016 |
| WO | 2016/201304 A1 | 12/2016 |
| WO | 2019/177986 A1 | 9/2019 |
| WO | 2021/100001 A1 | 5/2021 |

OTHER PUBLICATIONS

Oxford Reference (2023, one page) (Year: 2023).*
Wu et al (Mol. Canc. Ther., 2015, 14 (12 suppl 2): abstract C173) (Year: 2015).*
Uherek et al (Blood, 2002, 100: 1265-1273) (Year: 2002).*
Koneru et al (OncoImmunol. 4:3, Mar. 2015, pp. 1-11) (Year: 2015).*
Zwaagstra et al (Mol. Canc. Ther. 2012, 11: 1477-1487) (Year: 2012).*
Knudson et al (Oncoimmunol. 2018, 7(5): e1426519, pp. 1-14) (Year: 2018).*
Scitable (2011, pp. 1-6) (Year: 2011).*
Suck et al (Canc. Immunol. Immunother. 2016, 65: 485-492) (Year: 2016).*
Fallon et al (Oncotarget, 2017 8(13): 20558-20571) (Year: 2017).*
David et al (Oncoimmunol. 2017, 6(10), e1349589: pp. 1-16) (Year: 2017).*
Emboss Needle 2023, 3 pages (Year: 2023).*
Ng et al (Mol.Ther. Oncolytics, Mar. 16, 2020, pp. 75-85 doi.org/10.1016/jomto.2019.12.006). (Year: 2020).*
Schomer et al (Blood, Nov. 29, 2018, 132 (Supplement 1): 4547) (Year: 2018).*
Gong et al, "Characterization of a Human Cell Line (NK-92) with Phenotypical and Functional Characteristics of Activated Natural Killer Cells", Leukemia, vol. 8, No. 4, Apr. 1994: pp. 652-658.
Konstantinidis et al, "Targeting IL-2 to the endoplasmic reticulum confines autocrine growth stimulation to NK-92 cells", Experimental Hematology 33 (2005) 159-164.

(Continued)

*Primary Examiner* — G. R. Ewoldt
*Assistant Examiner* — Marianne DiBrino
(74) *Attorney, Agent, or Firm* — Martin Fessenmaier; Umberg Zipser LLP

(57) ABSTRACT

A recombinant natural killer (NK) cell or T-cell composition is transfected with a nucleic acid encoding i) a homing receptor; ii) an antigen binding protein (ABP) or a chimeric antigen receptor (CAR) that specifically binds a target antigen; iii) an Fc Receptor; and/or iv) a secreted immune modulator selected from a TGFβ inhibitor and/or IL-12, where the recombinant cell is gamma (γ)-irradiated conferring inhibition of cell proliferation with transient activity of the transfected molecules including the secreted immune modulators for up to 72 hours.

11 Claims, 31 Drawing Sheets

Specification includes a Sequence Listing.

(56) References Cited

OTHER PUBLICATIONS

Paul et al, "Widespread Decreased Expression of Immune Function Genes in Human Peripheral Blood Following Radiation Exposure", Radiation Research 180, 575-583 (2013).
Schönfeld et al, "Selective Inhibition of Tumor Growth by Clonal NK Cells Expressing an ErbB2/HER2-Specific Chimeric Antigen Receptor", Molecular Therapy vol. 23 no. 2, 330-338 Feb. 2015.
International Preliminary Report on Patentability (Chapter II) received for PCT Application Serial No. PCT/IB2020/060945 dated Mar. 8, 2022, 8 pages.
International Search Report and Written Opinion received for PCT Application Serial No. PCT/IB2020/060945 dated Feb. 26, 2021, 11 pages.
First Office Action received for Canadian Patent Application Serial No. 3,159,602 dated Apr. 3, 2023, 4 pages.
Examination Report No. 1 received for Australian Patent Application No. 2020387167 dated Nov. 30, 2023, 03 pages.
Extended European Search Report received for European Patent Application No. 20888769.5 dated Nov. 20, 2023, 12 pages.
Fabian et al., "P217: An NK cell line (PD-LI t-haNK) engineered to target PD-LI efficiently kills tumor cells and myeloid derived suppressor cells", Journal for Immunotherapy of Cancer, vol. 7, No. Suppl 1, Nov. 6, 2019 (Nov. 6, 2019), p. 282 : p. 171.
Robbins et al., "P148: High affinity NK cells expressing a PD-LI chimeric antigen receptor demonstrate anti-tumor activity in head and neck cancer through multiple distinct mechanisms", Journal for Immunotherapy of Cancer, vol. 7, No. Suppl 1, Nov. 6, 2019 (Nov. 6, 2019), 282 : p. 81.
Jochems et al., "An NK cell line (haNK) expressing high levels of granzyme and engineered to express the high affinity CD16 allele", ONCOTARGET, vol. 7, No. 52, Dec. 27, 2016 (Dec. 27, 2016), pp. 86359-86373.
Yang et al., "Blocking transforming growth factor-[beta] signaling pathway augments antitumor effect of adoptive NK-92 cell therapy", International Immunopharmacology, vol. 17, No. 2, Oct. 17, 2013 (Oct. 17, 2013), pp. 198-204.
Examination Report No. 2 received for CA Application No. 3159602 dated Feb. 15, 2024, 04 pages.

\* cited by examiner

Post-irradiation Evaluation of Cell Growth (PD-L1 t-haNK)

Days in Culture / Viable Cell Density Counts (x 10⁶)

| Dose (Gy) | D0[1] | D1 | D2 | D3 | D4 | D10 | D15 | D21 | D28 | D35 |
|---|---|---|---|---|---|---|---|---|---|---|
| 0 | 0.5 | 0.48 | 0.44 | 0.79 | 0.43 | 0.96 | 0.9 | 1.27 | 0.9 | 0.8 |
| 2.5 | 0.5 | 0.4 | 0.35 | 0.39 | 0.16 | 0.03 | 0.008 | 0 | 0 | 0.003 |
| 5 | 0.5 | 0.4 | 0.28 | 0.25 | 0.078 | 0.03 | 0.002 | 0 | 0.0006[2] | 0 |
| 10 | 0.5 | 0.43 | 0.25 | 0.26 | 0.067 | 0.03 | 0.004 | 0.0006 | 0 | 0 |
| 15 | 0.5 | 0.38 | 0.26 | 0.23 | 0.088 | 0.01 | 0.001 | 0.0006 | 0.0006 | 0 |
| 20 | 0.5 | 0.37 | 0.24 | 0.21 | 0.063 | 0.02 | 0.002 | 0.0006 | 0 | 0.0006 |
| 30 | 0.5 | 0.31 | 0.21 | 0.22 | 0.057 | 0.01 | 0.004 | 0 | 0 | 0 |

1 D0: 0 Day post irradiation
2 Limit of detection (LOD) ≥ 0.0006 x 10⁶ cells

FIG. 5B

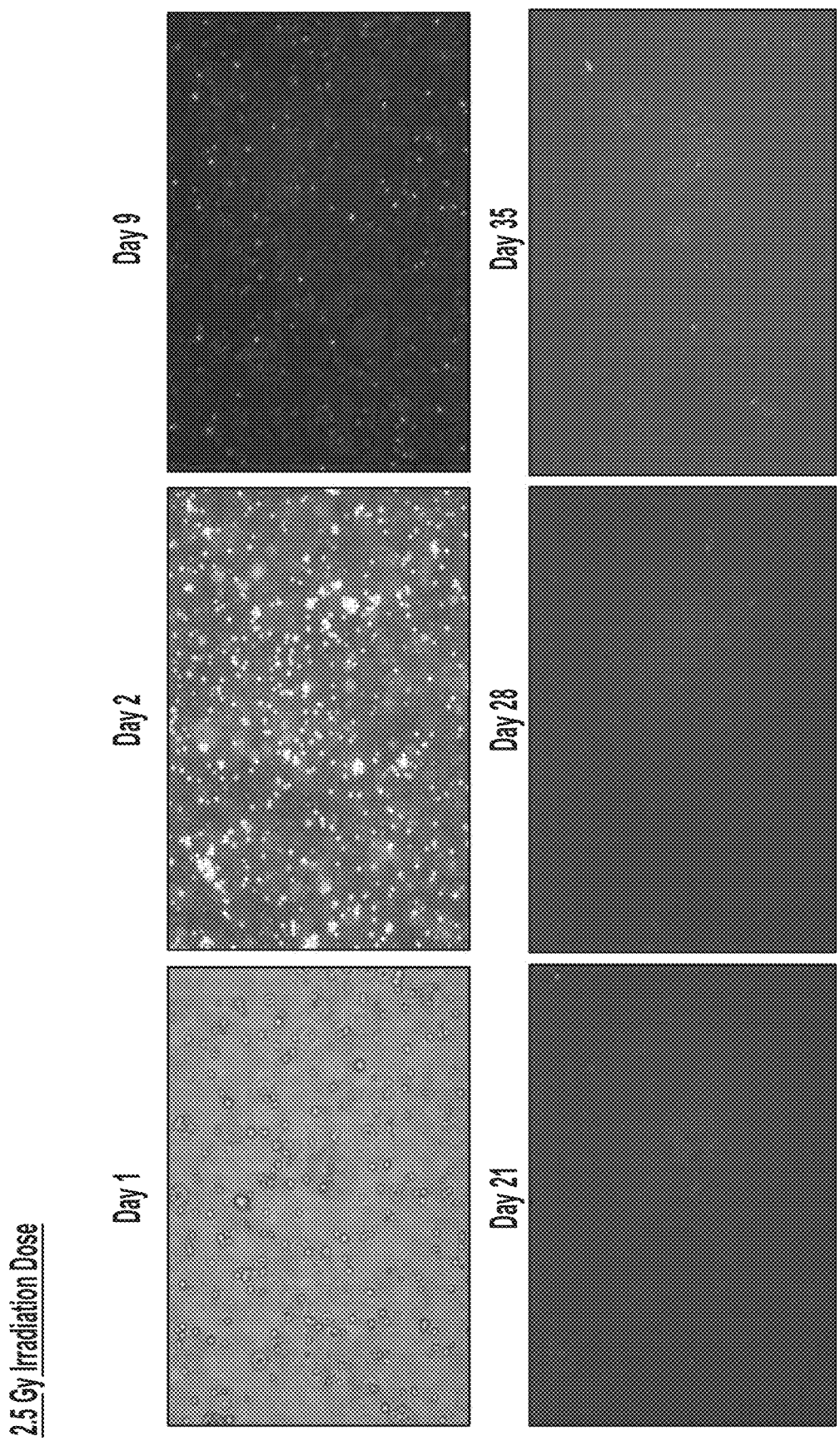

SEQUENCE LISTING

<160> NUMBER OF SEQ ID NOS: 69

<210> SEQ ID NO 1
<211> LENGTH: 1119

<212> TYPE: DNA
<213> ORGANISM: Artificial Sequence
<220> FEATURE:
<223> OTHER INFORMATION: Laboratory made

<400> SEQUENCE: 1

| | | | | | |
|---|---|---|---|---|---|
| atgaaaagcg | tgctggtggt | ggctctcctt | gtcattttcc | aggtatgcct | gtgtcaagat | 60 |
| gaggtcacgg | acgattacat | cggagacaac | accacagtgg | actacacttt | gttcgagtct | 120 |
| ttgtgctcca | agaaggacgt | gcggaacttt | aaagcctggt | tcctccctat | catgtactcc | 180 |
| atcatttgtt | tcgtgggcct | actgggcaat | gggctggtcg | tgttgaccta | tatctatttc | 240 |
| aagaggctca | agaccatgac | cgatacctac | ctgctcaacc | tggcggtggc | agacatcctc | 300 |
| ttcctcctga | cccttccctt | ctgggcctac | agcgcggcca | agtcctgggt | cttcggtgtc | 360 |
| cacttttgca | agctcatctt | tgccatctac | aagatgagct | tcttcagtgg | catgctccta | 420 |
| cttctttgca | tcagcattga | ccgctacgtg | gccatcgtcc | aggctgtctc | agctcaccgc | 480 |
| caccgtgccc | gcgtccttct | catcagcaag | ctgtcctgtg | tgggcatctg | gatactagcc | 540 |
| acagtgctct | ccatcccaga | gctcctgtac | agtgacctcc | agaggagcag | cagtgagcaa | 600 |
| gcgatgcgat | gctctctcat | cacagagcat | gtggaggcct | ttatcaccat | ccaggtggcc | 660 |
| cagatggtga | tcggctttct | ggtccccctg | ctggccatga | gcttctgtta | ccttgtcatc | 720 |
| atccgcaccc | tgctccaggc | acgcaacttt | gagcgcaaca | aggccatcaa | ggtgatcatc | 780 |
| gctgtggtcg | tggtcttcat | agtcttccag | ctgcccctaca | atggggtggt | cctggcccag | 840 |
| acggtggcca | acttcaacat | caccagtagc | acctgtgagc | tcagtaagca | actcaacatc | 900 |
| gcctacgacg | tcacctacag | cctggcctgc | gtccgctgct | gcgtcaaccc | tttcttgtac | 960 |
| gccttcatcg | gcgtcaagtt | ccgcaacgat | ctcttcaagc | tcttcaagga | cctgggctgc | 1020 |
| ctcagccagg | agcagctccg | gcagtggtct | tcctgtcggc | acatccggcg | ctcctccatg | 1080 |
| agtgtggagg | ccgagaccac | caccaccttc | tccccatag | | | 1119 |

<210> SEQ ID NO 2
<211> LENGTH: 405
<212> TYPE: DNA
<213> ORGANISM: Artificial Sequence
<220> FEATURE:
<223> OTHER INFORMATION: Laboratory made

<400> SEQUENCE: 2

| | | | | | |
|---|---|---|---|---|---|
| atggctcagt | cactggctct | gagcctcctt | atcctggttc | tggcctttgg | catccccagg | 60 |
| acccaaggca | gtgatggagg | ggctcaggac | tgttgcctca | agtacagcca | aaggaagatt | 120 |
| cccgccaagg | ttgtccgcag | ctaccggaag | caggaaccaa | gcttaggctg | ctccatccca | 180 |
| gctatcctgt | tcttgccccg | caagcgctct | caggcagagc | tatgtgcaga | cccaaaggag | 240 |
| ctctgggtgc | agcagctgat | gcagcatctg | gacaagacac | catccccaca | gaaaccagcc | 300 |
| cagggctgca | ggaaggacag | gggggcctcc | aagactggca | gaaaggaaa | gggctccaaa | 360 |
| ggctgcaaga | ggactgagcg | gtcacagacc | cctaaagggc | catag | | 405 |

<210> SEQ ID NO 3
<211> LENGTH: 1178
<212> TYPE: DNA
<213> ORGANISM: Artificial Sequence
<220> FEATURE:
<223> OTHER INFORMATION: laboratory made

<400> SEQUENCE: 3

| | | | | | |
|---|---|---|---|---|---|
| gctccggtgc | ccgtcagtgg | gcagagcgca | catcgcccac | agtccccgag | aagttggggg | 60 |
| gaggggtcgg | caattgaacc | ggtgcctaga | gaaggtggcg | cggggtaaac | tgggaaagtg | 120 |
| atgtcgtgta | ctggctccgc | cttttcccg | agggtggggg | agaaccgtat | ataagtgcag | 180 |
| tagtcgccgt | gaacgttctt | tttcgcaacg | ggtttgccgc | cagaacacag | gtaagtgccg | 240 |
| tgtgtggttc | ccgcgggcct | ggcctcttta | cgggttatgg | cccttgcgtg | ccttgaatta | 300 |
| cttccacctg | gctgcagtac | gtgattcttg | atcccgagct | tcgggttgga | agtgggtggg | 360 |
| agagttcgag | gccttgcgct | taaggagccc | cttcgcctcg | tgcttgagtt | gaggcctggc | 420 |
| ctgggcgctg | gggccgccgc | gtgcgaatct | ggtggcacct | tcgcgcctgt | ctcgctgctt | 480 |
| tcgataagtc | tctagccatt | taaaatttt | gatgacctgc | tgcgacgctt | ttttctggc | 540 |
| aagatagtct | tgtaaatgcg | ggccaagatc | tgcacactgg | tatttcggtt | tttggggccg | 600 |
| cgggcggcga | cggggcccgt | gcgtcccagc | gcacatgttc | ggcgaggcgg | ggcctgcgag | 660 |
| cgcggccacc | gagaatcgga | cggggtagt | ctcaagctgg | ccggcctgct | ctggtgcctg | 720 |
| gcctcgcgcc | gccgtgtatc | gccccgccct | gggcggcaag | gctggcccgg | tcggcaccag | 780 |
| ttgcgtgagc | ggaaagatgg | ccgcttcccg | gccctgctgc | agggagctca | aaatggagga | 840 |
| cgcggcgctc | gggagagcgg | gcgggtgagt | cacccacaca | aaggaaaagg | gcctttccgt | 900 |
| cctcagccgt | cgcttcatgt | gactccacgg | agtaccgggc | gccgtccagg | cacctcgatt | 960 |
| agttctcgag | cttttggagt | acgtcgtctt | taggttgggg | ggaggggttt | tatgcgatgg | 1020 |
| agtttccccca | cactgagtgg | gtggagactg | aagttaggcc | agcttggcac | ttgatgtaat | 1080 |
| tctccttgga | atttgccctt | tttgagtttg | gatcttggtt | cattctcaag | cctcagacag | 1140 |
| tggttcaaag | ttttttcctt | ccatttcagg | tgtcgtga | | | 1178 |

```
<210> SEQ ID NO 4
<211> LENGTH: 30
<212> TYPE: DNA
<213> ORGANISM: Artificial Sequence
<220> FEATURE:
<223> OTHER INFORMATION: laboratory made

<400> SEQUENCE: 4
```

| | |
|---|---|
| ggaggaaaaa ctgtttcata cagaaggcgt | 30 |

```
<210> SEQ ID NO 5
<211> LENGTH: 32
<212> TYPE: DNA
<213> ORGANISM: Artificial Sequence
<220> FEATURE:
<223> OTHER INFORMATION: laboratory made

<400> SEQUENCE: 5
```

| | |
|---|---|
| tagagggtat ataatggaag ctcgaattcc ag | 32 |

```
<210> SEQ ID NO 6
<211> LENGTH: 320
<212> TYPE: DNA
<213> ORGANISM: Artificial Sequence
<220> FEATURE:
<223> OTHER INFORMATION: laboratory made

<400> SEQUENCE: 6
```

| | | | | | |
|---|---|---|---|---|---|
| aataaaatat | ctttattttc | attacatctg | tgtgttggtt | ttttgtgtga | atcgatagta | 60 |
| ctaacatacg | ctctccatca | aaacaaaacg | aaacaaaaca | aactagcaaa | ataggctgtc | 120 |
| cccagtgcaa | gtgcaggtgc | cagaacattt | ctctggccta | actggccggt | acctgagctc | 180 |

```
gctagcggag gaaaaactgt tcatacaga aggcgtggag gaaaaactgt tcatacaga      240 aggcgtggag gaaaaactgt tcatacaga aggcgtagat ctagactcta gagggtatat      300
aatggaagct cgaattccag                                                 320
```

<210> SEQ ID NO 7
<211> LENGTH: 6887
<212> TYPE: DNA
<213> ORGANISM: Artificial Sequence
<220> FEATURE:
<223> OTHER INFORMATION: laboratory made

<400> SEQUENCE: 7

```
aggtcctgct ttctctgacc tgcattctct cccctgggcc tgtgccgctt tctgtctgca       60
gcttgtggcc tgggtcacct ctacggctgg cccagatcct tccctgccgc ctccttcagg      120
ttccgtcttc ctccactccc tcttcccctt gctctctgct gtgttgctgc caaggatgc       180 tctttccgga gcacttcctt ctcggcgctg caccacgtga tgtcctctga gcggatcctc      240
cccgtgtctg gtcctctcc gggcatctct cctccctcac ccaaccccat gccgtcttca      300
ctcgctgggt ccctttttcc ttctccttct ggggcctgtg ccatctctcg tttcttagga      360
tggccttctc cgacggatgt ctcccttgcg tcccgcctcc ccttcttgta ggcctgcatc      420
atcaccgttt tctggacaa ccccaaagta ccccgtctcc ctggctttag ccacctctcc      480
atcctcttgc tttctttgcc tggacacccc gttctcctgt ggattcgggt cacctctcac      540
tcctttcatt tgggcagctc ccctaccccc cttacctctc tagtctgtgc tagctcttcc      600 agcccctgt catggcatct tccaggggtc cgagagctca gctagtcttc ttcctccaac      660 ccgggccct atgtccactt caggacagca tgtttgctgc ctccagggat cctgtgtccc      720
cgagctggga ccaccttata ttcccagggc cggttaatgt ggctctggtt ctgggtactt      780
ttatctgtcc cctccacccc acagtggggt acctctagag ctgaccaaaa gagcaccaaa      840
ggcgccctga ccttcagccc ctacctgcgc tccggtgccc gtcagtgggc agagcgcaca      900
tcgcccacag tccccgagaa gttgggggga gggtcggca attgaaccgg tgcctagaga      960
aggtggcgcg gggtaaactg ggaaagtgat gtcgtgtact ggctccgcct ttttcccgag     1020
ggtgggggag aaccgtatat aagtgcagta gtcgccgtga acgttctttt tcgcaacggg     1080
tttgccgcca gaacacaggt aagtgccgtg tgtggttccc gcgggcctgg cctctttacg     1140
ggttatggcc cttgcgtgcc ttgaattact tccacctggc tgcagtacgt gattcttgat     1200
cccgagcttc gggttggaag tgggtgggag agttcgaggc cttgcgctta aggagcccct     1260
tcgcctcgtg cttgagttga ggcctggcct gggcgctggg ccgccgcgt gcgaatctgg     1320 tggcaccttc gcgcctgtct cgctgctttc gataagtctc tagccattta aaattttga     1380 tgacctgctg cgacgctttt tttctggcaa gatagtcttg taaatgcggg ccaagatctg     1440
cacactggta tttcggtttt tgggccgcg ggcggcgacg gggcccgtgc gtcccagcgc     1500
acatgttcgg cgaggcgggg cctgcgagcg cggccaccga gaatcggacg ggggtagtct     1560
caagctggcc ggcctgctct ggtgcctggc ctcgcgccgc cgtgtatcgc cccgccctgg     1620
gcggcaaggc tggcccggtc ggcaccagtt gcgtgagcgg aaagatggcc gcttcccggc     1680
cctgctgcag ggagctcaaa atggaggacg cggcgctcgg gagagcgggc gggtgagtca     1740
cccacacaaa ggaaaagggc cttccgtcc tcagccgtcg cttcatgtga ctccacggag     1800
taccgggcgc cgtccaggca cctcgattag ttctcgagct tttggagtac gtcgtcttta     1860
```

-continued

```
ggttgggggg aggggttttta tgcgatggag tttccccaca ctgagtgggt ggagactgaa    1920
gttaggccag cttggcactt gatgtaattc tccttggaat ttgccctttt tgagtttgga    1980
tcttggttca ttctcaagcc tcagacagtg gttcaaagtt ttttcttcc atttcaggtg     2040
tcgtgataat acgactcact atagggagac ccaagctgga attcggcggc cgccaccatg    2100
aaaagcgtgc tggtggtggc tctccttgtc attttccagg tatgcctgtg tcaagatgag    2160
gtcacggacg attacatcgg agacaacacc acagtggact acactttgtt cgagtctttg    2220
tgctccaaga aggacgtgcg gaactttaaa gcctggttcc tccctatcat gtactccatc    2280
atttgtttcg tgggcctact gggcaatggg ctggtcgtgt tgacctatat ctatttcaag    2340
aggctcaaga ccatgaccga tacctacctg ctcaacctgg cggtggcaga catcctcttc    2400
ctcctgaccc ttcccttctg ggcctacagc gcggccaagt cctgggtctt cggtgtccac    2460
ttttgcaagc tcatctttgc catctacaag atgagcttct tcagtggcat gctcctactt    2520
ctttgcatca gcattgaccg ctacgtggcc atcgtccagg ctgtctcagc tcaccgccac    2580
cgtgcccgcg tccttctcat cagcaagctg tcctgtgtgg gcatctggat actagccaca    2640
gtgctctcca tcccagagct cctgtacagt gacctccaga ggagcagcag tgagcaagcg    2700
atgcgatgct ctctcatcac agagcatgtg gaggccttta tcaccatcca ggtggcccag    2760
atggtgatcg gctttctggt cccccctgctg ccatgagct tctgttacct tgtcatcatc    2820
cgcacctgc tccaggcacg caactttgag cgcaacaagg ccatcaaggt gatcatcgct    2880
gtggtcgtgg tcttcatagt cttccagctg ccctacaatg gggtggtcct ggcccagacg    2940
gtggccaact tcaacatcac cagtagcacc tgtgagctca gtaagcaact caacatcgcc    3000
tacgacgtca cctacagcct ggcctgcgtc cgctgctgcg tcaacccttt cttgtacgcc    3060
ttcatcggcg tcaagttccg caacgatctc ttcaagctct tcaaggacct gggctgcctc    3120
agccaggagc agctccggca gtggtcttcc tgtcggcaca tccggcgctc ctccatgagt    3180
gtggaggcca agaccaccac caccttctcc ccataggcgg ccgcggtcat agctgtttcc    3240
tgaacagatc ccgggtggca tccctgtgac ccctccccag tgcctctcct ggccctggaa    3300
gttgccactc cagtgcccac cagccttgtc ctaataaaat taagttgcat cattttgtct    3360
gactaggtgt ccttctataa tattatgggg tggagggggg tggtatggag caaggggcaa    3420
gttgggaaga caacctgtag ggcctgcggg gtctattggg aaccaagctg gagtgcagtg    3480
gcacaatctt ggctcactgc aatctccgcc tcctgggttc aagcgattct cctgcctcag    3540
cctcccgagt tgttgggatt ccaggcatgc atgaccaggc tcagctaatt tttgttttt    3600
tggtagagac ggggtttcac catattggcc aggctggtct ccaactccta atctcaggtg    3660
atctacccac cttggcctcc caaattgctg ggattacagg cgtgaaccac tgctcccttc    3720
cctgtccttc tgattttaaa ataactatac cagcaggagg acgtccagac acagcatagg    3780
ctacctggcc atgcccaacc ggtgggacat ttgagttgct tgcttggcac tgtcctctca    3840
tgcgttgggt ccactcagta gatgcctgtt gaattgggta cgcggccagc ttaatgcata    3900
acttcgtata atgtatgcta tacgaagtta tgttaattaa gggtgcagcg gcctccgcgc    3960
cgggttttgg cgcctcccgc gggcgccccc tcctcacgg cgagcgctgc cacgtcagac    4020
gaagggcgca ggagcgttcc tgatccttcc gcccggacgc tcaggacagc ggcccgctgc    4080
tcataagact cggccttaga accccagtat cagcagaagg acattttagg acgggacttg    4140
ggtgactcta gggcactggt tttctttcca gagagcggaa caggcgagga aaagtagtcc    4200
cttctcggcg attctgcgga gggatctccg tggggcggtg aacgccgatg attatataag    4260
```

```
gacgcgccgg gtgtggcaca gctagttccg tcgcagccgg gatttgggtc gcggttcttg   4320
tttgtggatc gctgtgatcg tcacttggtg agttgcgggc tgctgggctg ccgggggctt   4380
tcgtggccgc cgggccgctc ggtgggacgg aagcgtgtgg agagaccgcc aagggctgta   4440
gtctgggtcc gcgagcaagg ttgccctgaa ctggggggttg gggggagcgc acaaaatggc   4500
ggctgttccc gagtcttgaa tggaagacgc ttgtaaggcg ggctgtgagg tcgttgaaac   4560
aaggtggggg gcatggtggg cggcaagaac ccaaggtctt gaggccttcg ctaatgcggg   4620
aaagctctta ttcgggtgag atgggctggg gcaccatctg ggaccctga cgtgaagttt   4680 gtcactgact ggagaactcg ggtttgtcgt ctggttgcgg gggcggcagt tatgcggtgc   4740
cgttgggcag tgcacccgta cctttgggag cgcgcgcctc gtcgtgtcgt gacgtcaccc   4800
gttctgttgg cttataatgc agggtggggc cacctgccgg taggtgtgcg gtaggctttt   4860
ctccgtcgca ggacgcaggg ttcgggccta gggtaggctc tcctgaatcg acaggcgccg   4920
gacctctggt gaggggaggg ataagtgagg cgtcagtttc tttggtcggt tttatgtacc   4980
tatcttctta agtagctgaa gctccggttt tgaactatgc gctcggggtt ggcgagtgtg   5040
ttttgtgaag ttttttaggc accttttgaa atgtaatcat ttgggtcaat atgtaatttt   5100
cagtgttaga ctagtaaatt gtccgctaaa ttctggccgt ttttggctttt tttgttagac   5160 gaagcttggg ctgcaggtcg actctagtgt aacgccacca tgaccgagta caagcctacc   5220
gtgaggctgg ccacccggga cgacgtgccc agagccgtga ggacactggc cgccgccttc   5280
gccgactacc ccgccacccg gcacaccgtg gaccccgacc ggcacatcga gcgggtgacc   5340
gagctgcagg aactgttcct gaccagagtg ggcctggata tcgcaaagt gtgggtggcc   5400 gacgacggag ccgccgtggc cgtgtggacc accccgagt ccgtggaggc cggagccgtg   5460
tttgccgaga tcggccccag gatggccgag ctgtccggca gcaggctggc cgcccagcag   5520
cagatggaag gcctgctggc ccctcaccgg cccaaagagc ccgcctggtt cctggccacc   5580
gtgggcgtga gccccgacca ccagggcaag ggcctgggca gcgccgtggt gctgccaggc   5640
gtggaagccg ccgagagggc cggagtgccc gccttcctgg aaaccagcgc ccccaggaac   5700
ctgcccttct acgagcggct gggctttacc gtgaccgccg acgtggaggt gccagagggc   5760
cccaggacct ggtgcatgac ccggaagcca ggcgcctgag aaaagcttat aacttcgtat   5820
aatgtatgct atacgaagtt ataacttgtt tattgcagct tataatggtt acaaataaag   5880
caatagcatc acaaatttca caaataaagc attttttttca ctgcattcta gttgtggttt   5940
gtccaaactc atcaatgtat cttatcatgt ctgtgcggtg ggctctatgg cttctgaggc   6000
ggaaagaacc agctggggct ctaggggta tcccctctag agtactaggg acaggattgg   6060
tgacagaaaa gccccatcct taggcctcct ccttcctagt ctcctgatat tgggtctaac   6120
ccccacctcc tgttaggcag attccttatc tggtgacaca ccccatttc ctggagccat   6180 ctctctcctt gccagaacct ctaaggtttg cttacgatgg agccagagag gatcctggga   6240
gggagagctt ggcagggggt gggagggaag gggggatgc gtgacctgcc cggttctcag   6300
tggccaccct cgctaccct ctcccagaac ctgagctgct ctgacgcggc tgtctggtgc   6360
gtttcactga tcctggtgct gcagcttcct tacacttccc aagaggagaa gcagtttgga   6420
aaaacaaaat cagaataagt tggtcctgag ttctaacttt ggctcttcac ctttctagtc   6480
cccaatttat attgttcctc cgtgcgtcag ttttacctgt gagataaggc cagtagccaa   6540
ccccgtcctg gcagggctgt ggtgaggagg ggggtgtccg tgtggaaaac tccctttgtg   6600
```

| | |
|---|---:|
| agaatggtgc gtcctaggtg ttcaccaggt cgtggccgcc tctactccct ttctctttct | 6660 |
| ccatccttct ttccttaaag agtccccagt gctatctggg acatattcct ccgcccagag | 6720 |
| cagggtcccg cttccctaag gccctgctct gggcttctgg gtttgagtcc ttggcaagcc | 6780 |
| caggagaggc gctcaggctt ccctgtcccc cttcctcgtc caccatctca tgcccctggc | 6840 |
| tctcctgccc cttccctaca ggggttcctg gctctgctct tcagact | 6887 |

```
<210> SEQ ID NO 8
<211> LENGTH: 2497
<212> TYPE: DNA
<213> ORGANISM: Artificial Sequence
<220> FEATURE:
<223> OTHER INFORMATION: laboratory made

<400> SEQUENCE: 8
```

| | |
|---|---:|
| ataacttcgt ataatgtatg ctatacgaag ttatggcgcg ccgaagttcc tattcttcta | 60 |
| gaagaatagg aacttccgaa taggaacttc ctgcacgtga acttgtttat tgcagcttat | 120 |
| aatggttaca aataaagcaa tagcatcaca aatttcacaa ataaagcatt ttttcactg | 180 |
| cattctagtt gtggtttgtc caaactcatc aatgtatctt atcatgtctg tgagctgaag | 240 |
| gtacgctgta tctcagtcag tcaagctagc tcaggtttag ttcctggtgt acttgagggg | 300 |
| gatgagttcc tcaatggtgg ttttgaccag cttgccattc atctcaatga gcacaaagca | 360 |
| gtcaggagca tagtcagaga tcagctctct acacatgcca caggggctga ccaccctgat | 420 |
| ggatctgtcc acctcatcag gtaggggtg cctgacagcc acaatggtgt caaagtcctt | 480 |
| ctgcccgttg ctcacagcag acccaatggc aatggcttca gcacagacag tgaccctgcc | 540 |
| aatgtaggct tcaatgtgga cagcagagat gatctcccca gtcttggtcc tgatggccgc | 600 |
| cccgacatgt tgcttgttgt cctcatagag catggtgatc ttctcagtgg cgacctccac | 660 |
| cagctccaga tcctgctgag agatgttgaa ggttttcatg ttgggatcca cgtggagctc | 720 |
| tgcttatata gacctcccac cgtacacgcc taccgcccat ttgcgtcaac ggggcggggt | 780 |
| tattacgaca ttttggaaag tcccgttgat tttggtgcca aaacaaactc ccattgacgt | 840 |
| caatggggtg gagacttgga aatccccgtg agtcaaaccg ctatccacgc ccattggtgt | 900 |
| actgccaaaa ccgcatcacc atggtgaagt tcctattctc tagaaagaat aggaacttcc | 960 |
| gaataggaac ttcggtacgg gaggtattgg acaggccgca ataaaatatc tttatttca | 1020 |
| ttacatctgt gtgttggttt tttgtgtgaa tcgatagtac taacatacgc tctccatcaa | 1080 |
| aacaaaacga aacaaaacaa actagcaaaa taggctgtcc ccagtgcaag tgcaggtgcc | 1140 |
| agaacatttc tctggcctaa ctggccggta cctgagctcg ctagcggagg aaaaactgtt | 1200 |
| tcatacagaa ggcgtggagg aaaaactgtt tcatacagaa ggcgtggagg aaaaactgtt | 1260 |
| tcatacagaa ggcgtagatc tagactctag agggtatata atggaagctc gaattccagc | 1320 |
| ttggcattcc ggtactgttg gtaaaaagct tggcaatccg gtactgcctg caggaccgcc | 1380 |
| atggctcagt cactggctct gagcctcctt atcctggttc tggcctttgg catccccagg | 1440 |
| acccaaggca gtgatggagg ggctcaggac tgttgcctca agtacagcca aggaagatt | 1500 |
| cccgccaagg ttgtccgcag ctaccggaag caggaaccaa gcttaggctg ctccatccca | 1560 |
| gctatcctgt tcttgccccg caagcgctct caggcagagc tatgtgcaga cccaaaggag | 1620 |
| ctctgggtgc agcagctgat gcagcatctg gacaagacac catccccaca gaaaccagcc | 1680 |
| cagggctgca ggaaggacag gggggcctcc aagactggca gaaaggaaa gggctccaaa | 1740 |
| ggctgcaaga ggactgagcg gtcacagacc ccttaagaat tcgcggccgc ggtcatagct | 1800 |

```
gtttcctgaa cagatcccgg gtggcatccc tgtgacccct ccccagtgcc tctcctggcc    1860
ctggaagttg ccactccagt gcccaccagc cttgtcctaa taaaattaag ttgcatcatt    1920
ttgtctgact aggtgtcctt ctataatatt atggggtgga ggggggtggt atggagcaag    1980
gggcaagttg ggaagacaac ctgtagggcc tgcggggtct attgggaacc aagctggagt    2040
gcagtggcac aatcttggct cactgcaatc tccgcctcct gggttcaagc gattctcctg    2100
cctcagcctc ccgagttgtt gggattccag gcatgcatga ccaggctcag ctaattttttg   2160 ttttttttggt agagacgggg tttcaccata ttggccaggc tggtctccaa ctcctaatct    2220
caggtgatct acccaccttg gcctcccaaa ttgctgggat tacaggcgtg aaccactgct    2280
cccttccctg tccttctgat tttaaaataa ctataccagc aggaggacgt ccagacacag    2340
cataggctac ctggccatgc caaccggtgg gacatttga gttgcttgct tggcactgtc      2400
ctctcatgcg ttgggtccac tcagtagatg cctgttgaat tgggtacgcg ccagcttaa     2460 tgcataactt cgtataatgt atgctatacg aagttat                             2497

<210> SEQ ID NO 9
<211> LENGTH: 1211
<212> TYPE: DNA
<213> ORGANISM: Artificial Sequence
<220> FEATURE:
<223> OTHER INFORMATION: laboratory made

<400> SEQUENCE: 9
ggcctccgcg ccgggttttg gcgcctcccg cgggcgcccc cctcctcacg gcgagcgctg      60
ccacgtcaga cgaagggcgc aggagcgttc ctgatccttc cgcccggacg ctcaggacag     120
cggcccgctg ctcataagac tcggccttag aaccccagta tcagcagaag gacattttag     180
gacgggactt gggtgactct agggcactgg ttttctttcc agagagcgga acaggcgagg     240
aaaagtagtc ccttctcggc gattctgcgg agggatctcc gtgggcggt gaacgccgat      300 gattatataa ggacgcgccg ggtgtggcac agctagttcc gtcgcagccg ggatttgggt     360
cgcggttctt gtttgtggat cgctgtgatc gtcacttggt gagttgcggg ctgctgggct     420
ggccggggct ttcgtggccg ccgggccgct cggtgggacg gaagcgtgtg gagagaccgc    480
caagggctgt agtctgggtc cgcgagcaag gttgccctga actgggggtt gggggggagcg   540 cacaaaatgg cggctgttcc cgagtcttga atggaagacg cttgtaaggc gggctgtgag   600
gtcgttgaaa caaggtgggg ggcatggtgg gcggcaagaa cccaaggtct tgaggccttc    660
gctaatgcgg gaaagctctt attcgggtga gatgggctgg ggcaccatct ggggaccctg    720
acgtgaagtt tgtcactgac tggagaactc gggtttgtcg tctggttgcg ggggcggcag    780
ttatgcggtg ccgttgggca gtgcacccgt acctttggga gcgcgcgcct cgtcgtgtcg    840
tgacgtcacc cgttctgttg gcttataatg cagggtgggg ccacctgccg gtaggtgtgc    900
ggtaggcttt tctccgtcgc aggacgcagg gttcgggcct agggtaggct ctcctgaatc    960
gacaggcgcc ggacctctgg tgaggggagg gataagtgag gcgtcagttt ctttggtcgg   1020
ttttatgtac ctatcttctt aagtagctga agctccggtt ttgaactatg cgctcggggt   1080
tggcgagtgt gttttgtgaa gttttttagg cacctttttga aatgtaatca tttgggtcaa   1140
tatgtaattt tcagtgttag actagtaaat tgtccgctaa attctggccg ttttttggctt   1200 ttttgttaga c                                                         1211

<210> SEQ ID NO 10
```

<210> SEQ ID NO 10
<211> LENGTH: 500
<212> TYPE: DNA
<213> ORGANISM: Artificial Sequence
<220> FEATURE:
<223> OTHER INFORMATION: laboratory made

<400> SEQUENCE: 10

```
gggtagggga ggcgcttttc ccaaggcagt ctggagcatg cgctttagca gccccgctgg      60
gcacttggcg ctacacaagt ggcctctggc ctcgcacaca ttccacatcc accggtaggc     120
gccaaccggc tccgttcttt ggtggcccct tcgcgccacc ttctacccct ccctagtca     180
ggaagttccc ccccgccccg cagctcgcgt catgcaggac gtgacaaatg aagtagcac     240
gtctcactag tctcgtgcaa atggacagca ccgctgagca atggaagcgg gtaggccctt     300
ggggcagcgg ccaatagcag ctttgctcct tcgctttctg ggctcagagg ctgggaaggg     360
gtgggtccgg gggcgggctc aggggcgggc tcaggggcgg ggcgggcgcc cgaaggtcct     420
ccggaggccc ggcattccgc acgcttcaaa agcgcacgtc tgccgcgctg ttctcttctt     480
cctcatctcc gggcctttcg                                                 500
```

<210> SEQ ID NO 11
<211> LENGTH: 508
<212> TYPE: DNA
<213> ORGANISM: Artificial Sequence
<220> FEATURE:
<223> OTHER INFORMATION: laboratory made

<400> SEQUENCE: 11

```
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta     240
catgacctta tgggactttc ctacttggca gtacatctac gtattagtca tcgctattac     300
catgctgatg cggttttggc agtacatcaa tgggcgtgga tagcggtttg actcacgggg     360
atttccaagt ctccaccccca ttgacgtcaa tgggagtttg ttttggcacc aaaatcaacg     420
ggactttcca aaatgtcgta acaactccgc cccattgacg caaatgggcg gtaggcgtgt     480
acggtgggag gtctatataa gcagagct                                        508
```

<210> SEQ ID NO 12
<211> LENGTH: 254
<212> TYPE: PRT
<213> ORGANISM: Artificial Sequence
<220> FEATURE:
<223> OTHER INFORMATION: laboratory made

<400> SEQUENCE: 12

```
Met Trp Gln Leu Leu Pro Thr Ala Leu Leu Leu Val Ser Ala
1               5                   10                  15

Gly Met Arg Thr Glu Asp Leu Pro Lys Ala Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80
```

Val Asp Asp Ser Gly Glu Tyr Arg Cys Gln Thr Asn Leu Ser Thr Leu
            85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
            130                 135             140

Gly Lys Gly Arg Lys Tyr Phe His His Asn Ser Asp Phe Tyr Ile Pro
145             150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 13
<211> LENGTH: 765
<212> TYPE: DNA
<213> ORGANISM: Artificial Sequence
<220> FEATURE:
<223> OTHER INFORMATION: laboratory made

<400> SEQUENCE: 13

```
atgtggcagc tgctgctgcc tacagctctc ctgctgctgg tgtccgccgg catgagaacc      60
gaggatctgc ctaaggccgt ggtgttcctg aaccccagt ggtacagagt gctggaaaag     120
gacagcgtga ccctgaagtg ccagggcgcc tacagccccg aggacaatag cacccagtgg    180
ttccacaacg agagcctgat cagcagccag gccagcagct acttcatcga cgccgccacc    240
gtggacgaca cggcgagta tagatgccag accaacctga gcaccctgag cgaccccgtg    300
cagctggaag tgcacatcgg atggctgctg ctgcaggccc ccagatgggt gttcaaagaa    360
gaggacccca tccacctgag atgccactct tggaagaaca ccgccctgca caaagtgacc    420
tacctgcaga acggcaaggg cagaaagtac ttccaccaca cagcgacttc ctacatcccc    480
aaggccaccc tgaaggactc cggctcctac ttctgcagag gcctcgtggg cagcaagaac    540
gtgtccagcg agacagtgaa catcaccatc acccagggcc tggccgtgtc taccatcagc    600
agctttttcc cacccggcta ccaggtgtcc ttctgcctcg tgatggtgct gctgttcgcc    660
gtggacaccg gcctgtactt cagcgtgaaa acaaacatca gaagcagcac ccgggactgg    720
aaggaccaca gttcaagtg cggaaggac ccccaggaca gtga                       765
```

<210> SEQ ID NO 14
<211> LENGTH: 483
<212> TYPE: DNA
<213> ORGANISM: Artificial Sequence
<220> FEATURE:
<223> OTHER INFORMATION: laboratory made

<400> SEQUENCE: 14

```
atgtaccgga tgcagctgct gagctgtatc gccctgtctc tggccctcgt gaccaacagc    60
gcccctacca gcagcagcac caagaaaacc cagctgcagc tggaacatct gctgctggac   120
ctgcagatga tcctgaacgg catcaacaac tacaagaacc ccaagctgac ccggatgctg   180
accttcaagt tctacatgcc caagaaggcc accgaactga acatctgca gtgcctggaa   240 gaggaactga agcccctgga agaagtgctg aacctggccc agagcaagaa cttccacctg   300
aggcccaggg acctgatcag caacatcaac gtgatcgtgc tggaactgaa aggcagcgag   360
acaaccttca gtgcgagta cgccgacgag acagctacca tcgtggaatt tctgaaccgg   420
tggatcacct tctgccagag catcatcagc accctgaccg gctccgagaa ggacgagctg   480
tga                                                                 483
```

<210> SEQ ID NO 15
<211> LENGTH: 164
<212> TYPE: PRT
<213> ORGANISM: Artificial Sequence
<220> FEATURE:
<223> OTHER INFORMATION: laboratory made

<400> SEQUENCE: 15

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Ser Glu Lys Asp Glu Leu
145                 150                 155                 160

Lys Asp Glu Leu
```

<210> SEQ ID NO 16
<211> LENGTH: 297
<212> TYPE: DNA
<213> ORGANISM: Artificial Sequence
<220> FEATURE:
<223> OTHER INFORMATION: laboratory made

<400> SEQUENCE: 16

```
atggccctgc tactgccct cagcctgctg gttctctgga cttccccagc cccaactctg    60
agtggcacca atgatgctga agactgctgc ctgtctgtga cccagaaacc catccctggg   120
tacatcgtga ggaacttcca ctaccttctc atcaaggatg gctgcagggt gcctgctgta   180
gtgttcacca cactgagggg ccgccagctc tgtgcacccc cagaccagcc ctgggtagaa   240
cgcatcatcc agagactgca gaggacctca gccaagatga gcgccgcag cagttaa      297
```

```
<210> SEQ ID NO 17
<211> LENGTH: 60
<212> TYPE: DNA
<213> ORGANISM: Artificial Sequence
<220> FEATURE:
<223> OTHER INFORMATION: laboratory made

<400> SEQUENCE: 17
cagtgcacca actacgccct gctgaagctg gccggcgacg tggagagcaa ccctggccct    60

<210> SEQ ID NO 18
<211> LENGTH: 54
<212> TYPE: DNA
<213> ORGANISM: Artificial Sequence
<220> FEATURE:
<223> OTHER INFORMATION: laboratory made

<400> SEQUENCE: 18
gagggcagag gcagcctgct gacctgcggc gatgtggagg aaaacccagg ccca          54

<210> SEQ ID NO 19
<211> LENGTH: 806
<212> TYPE: DNA
<213> ORGANISM: Artificial Sequence
<220> FEATURE:
<223> OTHER INFORMATION: laboratory made

<400> SEQUENCE: 19
tgctttctct gacctgcatt ctctcccctg ggcctgtgcc gctttctgtc tgcagcttgt    60
ggcctgggtc acctctacgg ctggcccaga tccttccctg ccgcctcctt caggttccgt   120
cttcctccac tccctcttcc ccttgctctc tgctgtgttg ctgcccaagg atgtctttc    180 cggagcactt ccttctcggc gctgcaccac gtgatgtcct ctgagcggat cctccccgtg   240
tctgggtcct ctccgggcat ctctcctccc tcacccaacc ccatgccgtc ttcactcgct   300
gggttccctt ttccttctcc ttctggggcc tgtgccatct ctcgtttctt aggatggcct   360
tctccgacgg atgtctccct tgcgtcccgc ctccccttct tgtaggcctg catcatcacc   420 gttttttctgg acaaccccaa agtacccgt ctccctggct ttagccacct ctccatcctc    480
ttgctttctt tgcctggaca ccccgttctc ctgtggattc gggtcacctc tcactccttt   540
catttgggca gctcccctac ccccttacc tctctagtct gtgctagctc ttccagcccc    600
ctgtcatggc atcttccagg ggtccgagag ctcagctagt cttcttcctc caacccgggc   660
ccctatgtcc acttcaggac agcatgtttg ctgcctccag ggatcctgtg tccccgagct   720
gggaccacct tatattccca gggccggtta atgtggctct ggttctgggt acttttatct   780
gtcccctcca ccccacagtg gggtac                                        806

<210> SEQ ID NO 20
<211> LENGTH: 1178
<212> TYPE: DNA
<213> ORGANISM: Artificial Sequence
<220> FEATURE:
<223> OTHER INFORMATION: Laboratory made

<400> SEQUENCE: 20
gctccggtgc ccgtcagtgg gcagagcgca catcgcccac agtccccgag aagttggggg    60 gagggggtcgg caattgaacc ggtgcctaga gaaggtggcg cggggtaaac tgggaaagtg   120
atgtcgtgta ctggctccgc cttttccccg agggtgggggg agaaccgtat ataagtgcag   180
```

| | |
|---|---|
| tagtcgccgt gaacgttctt tttcgcaacg ggtttgccgc cagaacacag gtaagtgccg | 240 |
| tgtgtggttc ccgcgggcct ggcctcttta cgggttatgg cccttgcgtg ccttgaatta | 300 |
| cttccacctg gctgcagtac gtgattcttg atcccgagct tcgggttgga agtgggtggg | 360 |
| agagttcgag gccttgcgct taaggagccc cttcgcctcg tgcttgagtt gaggcctggc | 420 |
| ctgggcgctg gggccgccgc gtgcgaatct ggtggcacct tcgcgcctgt ctcgctgctt | 480 |
| tcgataagtc tctagccatt taaaattttt gatgacctgc tgcgacgctt ttttctggc | 540 |
| aagatagtct tgtaaatgcg ggccaagatc tgcacactgg tatttcggtt tttggggccg | 600 |
| cgggcggcga cggggcccgt gcgtcccagc gcacatgttc ggcgaggcgg ggcctgcgag | 660 |
| cgcggccacc gagaatcgga cggggtagt ctcaagctgg ccggcctgct ctggtgcctg | 720 |
| gcctcgcgcc gccgtgtatc gccccgcccct gggcggcaag gctggcccgg tcggcaccag | 780 |
| ttgcgtgagc ggaaagatgg ccgcttcccg gccctgctgc agggagctca aaatggagga | 840 |
| cgcggcgctc gggagagcgg gcgggtgagt cacccacaca aaggaaaagg gcctttccgt | 900 |
| cctcagccgt cgcttcatgt gactccacgg agtaccgggc gccgtccagg cacctcgatt | 960 |
| agttctcgag cttttggagt acgtcgtctt taggttgggg ggaggggttt tatgcgatgg | 1020 |
| agtttcccca cactgagtgg gtggagactg aagttaggcc agcttggcac ttgatgtaat | 1080 |
| tctccttgga atttgcccctt tttgagtttg gatcttggtt cattctcaag cctcagacag | 1140 |
| tggttcaaag ttttttctt ccatttcagg tgtcgtga | 1178 |

<210> SEQ ID NO 21
<211> LENGTH: 19
<212> TYPE: DNA
<213> ORGANISM: Artificial Sequence
<220> FEATURE:
<223> OTHER INFORMATION: laboratory made

<400> SEQUENCE: 21

| | |
|---|---|
| taatacgact cactatagg | 19 |

<210> SEQ ID NO 22
<211> LENGTH: 1116
<212> TYPE: DNA
<213> ORGANISM: Artificial Sequence
<220> FEATURE:
<223> OTHER INFORMATION: laboratory made

<400> SEQUENCE: 22

| | |
|---|---|
| atgaaaagcg tgctggtggt ggctctcctt gtcatttcc aggtatgcct gtgtcaagat | 60 |
| gaggtcacgg acgattacat cggagacaac accacagtgg actacacttt gttcgagtct | 120 |
| ttgtgctcca agaaggacgt gcggaacttt aaagcctggt tcctccctat catgtactcc | 180 |
| atcatttgtt tcgtgggcct actgggcaat gggctggtcg tgttgaccta tatctatttc | 240 |
| aagaggctca agaccatgac cgatacctac ctgctcaacc tggcggtggc agacatcctc | 300 |
| ttcctcctga cccttccctt ctgggcctac agcgcggcca gtcctgggt cttcggtgtc | 360 |
| cacttttgca agctcatctt tgccatctac aagatgagct tcttcagtgg catgctccta | 420 |
| cttctttgca tcagcattga ccgctacgtg gccatcgtcc aggctgtctc agctcaccgc | 480 |
| caccgtgccc gcgtccttct catcagcaag ctgtcctgtg tgggcatctg gatactagcc | 540 |
| acagtgctct ccatcccaga gctcctgtac agtgacctcc agaggagcag cagtgagcaa | 600 |
| gcgatgcgat gctctctcat cacagagcat gtggaggcct ttatcaccat ccaggtggcc | 660 |
| cagatggtga tcggctttct ggtccccctg ctggccatga gcttctgtta ccttgtcatc | 720 |

```
atccgcaccc tgctccaggc acgcaacttt gagcgcaaca aggccatcaa ggtgatcatc     780
gctgtggtcg tggtcttcat agtcttccag ctgcccctaca atggggtggt cctggcccag    840
acggtggcca acttcaacat caccagtagc acctgtgagc tcagtaagca actcaacatc    900
gcctacgacg tcacctacag cctggcctgc gtccgctgct gcgtcaaccc tttcttgtac    960
gccttcatcg gcgtcaagtt ccgcaacgat ctcttcaagc tcttcaagga cctgggctgc    1020
ctcagccagg agcagctccg gcagtggtct tcctgtcggc acatccggcg ctcctccatg    1080
agtgtggagg ccgagaccac caccaccttc tcccca                              1116
```

<210> SEQ ID NO 23
<211> LENGTH: 66
<212> TYPE: DNA
<213> ORGANISM: Artificial Sequence
<220> FEATURE:
<223> OTHER INFORMATION: laboratory made

<400> SEQUENCE: 23

```
ggatctggag ctactaactt cagcctgctg aagcaggctg agacgtgga ggagaaccct    60 ggacct                                                               66
```

<210> SEQ ID NO 24
<211> LENGTH: 69
<212> TYPE: DNA
<213> ORGANISM: Artificial Sequence
<220> FEATURE:
<223> OTHER INFORMATION: laboratory made

<400> SEQUENCE: 24

```
atggactgga tctggcggat tctgtttctc gtgggagctg ccacaggcgc tcattctgct    60
cagcctgcc                                                            69
```

<210> SEQ ID NO 25
<211> LENGTH: 1152
<212> TYPE: DNA
<213> ORGANISM: Artificial Sequence
<220> FEATURE:
<223> OTHER INFORMATION: laboratory made

<400> SEQUENCE: 25

```
gatatccaga tgacccagac aacaagcagc ctgagcgcct ctctgggcga tagagtgaca    60
atcagctgca gagccagcca ggacatcagc aagtacctga actggtatca gcagaaaccc    120
gacggcaccg tgaagctgct gatctaccac acaagcagac tgcacagcgg cgtgccaagc    180
agattttctg gcagcggcag cggcaccgat tacagcctga ccatcagcaa cctggaacag    240
gaagatatcg ctacctactt ctgtcagcag gcaacaccc tgccttacac ctttggcggc    300
ggaacaaagc tggaactgaa agaggcggc ggaggaagcg gaggcggagg atctggggc    360 ggaggctctg gcgaggggg atctgaagtg cagctgcagc agtctggacc tggactggtg    420
gctccttctc agtccctgtc tgtgacctgt acagtgtctg gcgtgtccct gcctgattac    480
ggcgtgtcct ggatcagaca gcctcccaga aaaggcctgg aatggctggg agtgatctgg    540
ggcagcgaga caacctacta caacagcgcc ctgaagtccc ggctgaccat catcaaggac    600
aacagcaaga gccaggtgtt cctgaagatg aacagcctgc agaccgacga caccgccatc    660
tactactgcg ccaagcacta ctactacggc ggcagctacg ccatggatta ttggggccag    720
ggcaccaccg tgacagtgtc atctgcggcc gcgctgagca acagcatcat gtacttcagc    780
```

| | |
|---|---|
| cacttcgtgc ctgtgttcct gcctgccaag cctacaacaa caccagcccc tagacctcca | 840 |
| acccctgccc ctacaattgc ctctcagcct ctgtctctga ggcccgaagc ttgtagacct | 900 |
| gctgctggcg gagctgtgca caccagagga ctggatttcg cctgcttttg ggtgctggtg | 960 |
| gtcgtgggcg gagtgctggc ttgttattct ctgctggtca ccgtggcctt catcatcttt | 1020 |
| tgggtccgac tgaagatcca ggtccgaaag gccgccatca ccagctacga aagtctgat | 1080 |
| ggcgtgtaca ccggcctgag caccagaaac caggaaacct acgagacact gaagcacgag | 1140 |
| aagcccccc ag | 1152 |

<210> SEQ ID NO 26
<211> LENGTH: 765
<212> TYPE: DNA
<213> ORGANISM: Artificial Sequence
<220> FEATURE:
<223> OTHER INFORMATION: laboratory made

<400> SEQUENCE: 26

| | |
|---|---|
| atgtggcagc tgctgctgcc tacagctctc ctgctgctgg tgtccgccgg catgagaacc | 60 |
| gaggatctgc ctaaggccgt ggtgttcctg aaccccagt ggtacagagt gctggaaaag | 120 |
| gacagcgtga ccctgaagtg ccagggcgcc tacagcccccg aggacaatag cacccagtgg | 180 |
| ttccacaacg agagcctgat cagcagccag gccagcagct acttcatcga cgccgccacc | 240 |
| gtggacgaca gcgcgagta tagatgccag accaacctga gcaccctgag cgaccccgtg | 300 |
| cagctggaag tgcacatcgg atggctgctg ctgcaggccc ccagatgggt gttcaaagaa | 360 |
| gaggaccccca tccacctgag atgccactct tggaagaaca ccgccctgca caaagtgacc | 420 |
| tacctgcaga acggcaaggg cagaaagtac ttccaccaca cagcgactt ctacatcccc | 480 |
| aaggccaccc tgaaggactc cggctcctac ttctgcagag gctcgtggg cagcaagaac | 540 |
| gtgtccagcg agacagtgaa catcaccatc acccagggcc tggccgtgtc taccatcagc | 600 |
| agcttttttcc cacccggcta ccaggtgtcc ttctgcctcg tgatggtgct gctgttcgcc | 660 |
| gtggacaccg gcctgtactt cagcgtgaaa acaaacatca gaagcagcac ccgggactgg | 720 |
| aaggaccaca gttcaagtg gcggaaggac ccccaggaca agtga | 765 |

<210> SEQ ID NO 27
<211> LENGTH: 597
<212> TYPE: DNA
<213> ORGANISM: Artificial Sequence
<220> FEATURE:
<223> OTHER INFORMATION: laboratory made

<400> SEQUENCE: 27

| | |
|---|---|
| aattccgccc ctctccccccc ccccctctc cctccccccc ccctaacgtt actggccgaa | 60 |
| gccgcttgga ataaggccgg tgtgcgtttg tctatatgtt attttccacc atattgccgt | 120 |
| cttttggcaa tgtgagggcc cggaaacctg gccctgtctt cttgacgagc attcctaggg | 180 |
| gtctttcccc tctcgccaaa ggaatgcaag gtctgttgaa tgtcgtgaag gaagcagttc | 240 |
| ctctggaagc ttcttgaaga caaacaacgt ctgtagcgac cctttgcagg cagcggaacc | 300 |
| ccccacctgg cgacaggtgc ctctgcggcc aaaagccacg tgtataagat acacctgcaa | 360 |
| aggcggcaca accccagtgc cacgttgtga gttggatagt tgtggaaaga gtcaaatggc | 420 |
| tctcctcaag cgtattcaac aaggggctga aggatgccca gaaggtaccc cattgtatgg | 480 |
| gatctgatct ggggcctcgg tgcacatgct ttacatgtgt ttagtcgagg ttaaaaaaac | 540 |
| gtctaggccc cccgaaccac ggggacgtgg ttttcctttg aaaaacacga taaccgc | 597 |

<210> SEQ ID NO 28
<211> LENGTH: 483
<212> TYPE: DNA
<213> ORGANISM: Artificial Sequence
<220> FEATURE:
<223> OTHER INFORMATION: laboratory made

<400> SEQUENCE: 28

```
atgtaccgga tgcagctgct gagctgtatc gccctgtctc tggccctcgt gaccaacagc      60
gcccctacca gcagcagcac caagaaaacc cagctgcagc tggaacatct gctgctggac     120
ctgcagatga tcctgaacgg catcaacaac tacaagaacc ccaagctgac ccggatgctg     180
accttcaagt tctacatgcc caagaaggcc accgaactga acatctgca gtgcctggaa      240 gaggaactga agcccctgga agaagtgctg aacctggccc agagcaagaa cttccacctg     300
aggcccaggg acctgatcag caacatcaac gtgatcgtgc tggaactgaa aggcagcgag     360
acaaccttca tgtgcgagta cgccgacgag acagctacca tcgtggaatt tctgaaccgg     420
tggatcacct tctgccagag catcatcagc accctgaccg gctccgagaa ggacgagctg     480
tga                                                                   483
```

<210> SEQ ID NO 29
<211> LENGTH: 252
<212> TYPE: DNA
<213> ORGANISM: Artificial Sequence
<220> FEATURE:
<223> OTHER INFORMATION: laboratory made

<400> SEQUENCE: 29

```
acgagatttc gattccaccg ccgccttcta tgaaaggttg ggcttcggaa tcgtttttccg      60 ggacgccggc tggatgatcc tccagcgcgg ggatctcatg ctggagttct tcgcccaccc     120
caacttgttt attgcagctt ataatggtta caaataaagc aatagcatca caaatttcac     180
aaataaagca ttttttttcac tgcattctag ttgtggtttg tccaaactca tcaatgtatc     240
ttatcatgtc tg                                                         252
```

<210> SEQ ID NO 30
<211> LENGTH: 844
<212> TYPE: DNA
<213> ORGANISM: Artificial Sequence
<220> FEATURE:
<223> OTHER INFORMATION: laboratory made

<400> SEQUENCE: 30

```
ctagggacag gattggtgac agaaaagccc catccttagg cctcctcctt cctagtctcc      60
tgatattggg tctaaccccc acctcctgtt aggcagattc cttatctggt gacacacccc     120
catttcctgg agccatctct ctccttgcca gaacctctaa ggtttgctta cgatggagcc     180
agagaggatc ctgggaggga gagcttggca gggggtggga gggaagggggg ggatgcgtga    240 cctgcccggt tctcagtggc caccctgcgc taccctctcc cagaacctga gctgctctga    300
cgcggctgtc tggtgcgttt cactgatcct ggtgctgcag cttccttaca cttcccaaga    360
ggagaagcag tttggaaaaa caaaatcaga ataagttggt cctgagttct aactttggct    420
cttcaccttt ctagtcccca atttatattg ttcctccgtg cgtcagtttt acctgtgaga    480
taaggccagt agccagcccc gtcctggcag ggctgtggtg aggagggggg tgtccgtgtg    540
gaaaactccc tttgtgagaa tggtgcgtcc taggtgttca ccaggtcgtg gccgcctcta    600
```

```
ctcccttcct ctttctccat ccttctttcc ttaaagagtc cccagtgcta tctgggacat    660
attcctccgc ccagagcagg gtcccgcttc cctaaggccc tgctctgggc ttctgggttt    720
gagtccttgg caagcccagg agaggcgctc aggcttccct gtccccttc ctcgtccacc     780 atctcatgcc cctggctctc ctgccccttc cctacagggg ttcctggctc tgctcttcag    840
actg                                                                 844
```

<210> SEQ ID NO 31
<211> LENGTH: 41
<212> TYPE: PRT
<213> ORGANISM: Artificial Sequence
<220> FEATURE:
<223> OTHER INFORMATION: laboratory made

<400> SEQUENCE: 31

```
Leu Lys Ile Gln Val Arg Lys Ala Ala Ile Thr Ser Tyr Glu Lys Ser
1               5                   10                  15

Asp Gly Val Tyr Thr Gly Leu Ser Thr Arg Asn Gln Glu Thr Tyr Glu
            20                  25                  30

Thr Leu Lys His Glu Lys Pro Pro Gln
        35                  40
```

<210> SEQ ID NO 32
<211> LENGTH: 123
<212> TYPE: DNA
<213> ORGANISM: Artificial Sequence
<220> FEATURE:
<223> OTHER INFORMATION: laboratory made

<400> SEQUENCE: 32

```
ctgaagatcc aggtccgaaa ggccgccatc accagctacg agaagtctga tggcgtgtac    60
accggcctga gcaccagaaa ccaggaaacc tacgagacac tgaagcacga aagcccccc     120 cag                                                                  123
```

<210> SEQ ID NO 33
<211> LENGTH: 64
<212> TYPE: PRT
<213> ORGANISM: Artificial Sequence
<220> FEATURE:
<223> OTHER INFORMATION: laboratory made

<400> SEQUENCE: 33

```
Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp Phe Ala Cys
    50                  55                  60
```

<210> SEQ ID NO 34
<211> LENGTH: 192
<212> TYPE: DNA
<213> ORGANISM: Artificial Sequence
<220> FEATURE:
<223> OTHER INFORMATION: laboratory made

<400> SEQUENCE: 34

```
ctgagcaaca gcatcatgta cttcagccac ttcgtgcctg tgttcctgcc tgccaagcct    60
```

```
acaacaacac cagcccctag acctccaacc cctgcccta caattgcctc tcagcctctg    120
tctctgaggc ccgaagcttg tagacctgct gctggcggag ctgtgcacac cagaggactg    180
gatttcgcct gc                                                        192
```

```
<210> SEQ ID NO 35
<211> LENGTH: 28
<212> TYPE: PRT
<213> ORGANISM: Artificial Sequence
<220> FEATURE:
<223> OTHER INFORMATION: laboratory made

<400> SEQUENCE: 35
```

Phe Trp Val Leu Val Val Val Gly Gly Val Leu Ala Cys Tyr Ser Leu
1               5                   10                  15

Leu Val Thr Val Ala Phe Ile Ile Phe Trp Val Arg
            20                  25

```
<210> SEQ ID NO 36
<211> LENGTH: 84
<212> TYPE: DNA
<213> ORGANISM: Artificial Sequence
<220> FEATURE:
<223> OTHER INFORMATION: laboratory made

<400> SEQUENCE: 36
```

```
ttttgggtgc tggtggtcgt gggcggagtg ctggcttgtt attctctgct ggtcaccgtg     60
gccttcatca tcttttgggt ccga                                            84
```

```
<210> SEQ ID NO 37
<211> LENGTH: 133
<212> TYPE: PRT
<213> ORGANISM: Artificial Sequence
<220> FEATURE:
<223> OTHER INFORMATION: laboratory made

<400> SEQUENCE: 37
```

Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp Phe Ala Cys
    50                  55                  60

Phe Trp Val Leu Val Val Val Gly Gly Val Leu Ala Cys Tyr Ser Leu
65                  70                  75                  80

Leu Val Thr Val Ala Phe Ile Ile Phe Trp Val Arg Leu Lys Ile Gln
                85                  90                  95

Val Arg Lys Ala Ala Ile Thr Ser Tyr Glu Lys Ser Asp Gly Val Tyr
            100                 105                 110

Thr Gly Leu Ser Thr Arg Asn Gln Glu Thr Tyr Glu Thr Leu Lys His
        115                 120                 125

Glu Lys Pro Pro Gln
    130

```
<210> SEQ ID NO 38
<211> LENGTH: 399
<212> TYPE: DNA
<213> ORGANISM: Artificial Sequence
<220> FEATURE:
```

-continued

<223> OTHER INFORMATION: laboratory made

<400> SEQUENCE: 38

```
ctgagcaaca gcatcatgta cttcagccac ttcgtgcctg tgttcctgcc tgccaagcct      60
acaacaacac cagcccctag acctccaacc cctgccccta caattgcctc tcagcctctg     120
tctctgaggc ccgaagcttg tagacctgct gctggcggag ctgtgcacac cagaggactg     180
gatttcgcct gcttttgggt gctggtggtc gtgggcggag tgctggcttg ttattctctg     240
ctggtcaccg tggccttcat catctttttgg gtccgactga agatccaggt ccgaaaggcc     300
gccatcacca gctacgagaa gtctgatggc gtgtacaccg gcctgagcac cagaaaccag     360
gaaacctacg agacactgaa gcacgagaag ccccccccag                            399
```

<210> SEQ ID NO 39
<211> LENGTH: 252
<212> TYPE: PRT
<213> ORGANISM: Artificial Sequence
<220> FEATURE:
<223> OTHER INFORMATION: laboratory made

<400> SEQUENCE: 39

```
Ala Gln Pro Ala Asp Ile Gln Met Thr Gln Thr Thr Ser Ser Leu Ser
 1               5                  10                  15
Ala Ser Leu Gly Asp Arg Val Thr Ile Ser Cys Arg Ala Ser Gln Asp
            20                  25                  30
Ile Ser Lys Tyr Leu Asn Trp Tyr Gln Gln Lys Pro Asp Gly Thr Val
        35                  40                  45
Lys Leu Leu Ile Tyr His Thr Ser Arg Leu His Ser Gly Val Pro Ser
    50                  55                  60
Arg Phe Ser Gly Ser Gly Ser Gly Thr Asp Tyr Ser Leu Thr Ile Ser
65                  70                  75                  80
Asn Leu Glu Gln Glu Asp Ile Ala Thr Tyr Phe Cys Gln Gln Gly Asn
                85                  90                  95
Thr Leu Pro Tyr Thr Phe Gly Gly Gly Thr Lys Leu Glu Leu Lys Arg
            100                 105                 110
Gly Gly Gly Gly Ser Gly Gly Gly Ser Gly Gly Gly Gly Ser Gly
        115                 120                 125
Gly Gly Gly Ser Glu Val Gln Leu Gln Gln Ser Gly Pro Gly Leu Val
    130                 135                 140
Ala Pro Ser Gln Ser Leu Ser Val Thr Cys Thr Val Ser Gly Val Ser
145                 150                 155                 160
Leu Pro Asp Tyr Gly Val Ser Trp Ile Arg Gln Pro Pro Arg Lys Gly
                165                 170                 175
Leu Glu Trp Leu Gly Val Ile Trp Gly Ser Glu Thr Thr Tyr Tyr Asn
            180                 185                 190
Ser Ala Leu Lys Ser Arg Leu Thr Ile Ile Lys Asp Asn Ser Lys Ser
        195                 200                 205
Gln Val Phe Leu Lys Met Asn Ser Leu Gln Thr Asp Asp Thr Ala Ile
    210                 215                 220
Tyr Tyr Cys Ala Lys His Tyr Tyr Gly Gly Ser Tyr Ala Met Asp
225                 230                 235                 240
Tyr Trp Gly Gln Gly Thr Thr Val Thr Val Ser Ser
                245                 250
```

<210> SEQ ID NO 40
<211> LENGTH: 113

```
<212> TYPE: PRT
<213> ORGANISM: Artificial Sequence
<220> FEATURE:
<223> OTHER INFORMATION: laboratory made

<400> SEQUENCE: 40

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 41
<211> LENGTH: 1410
<212> TYPE: DNA
<213> ORGANISM: Artificial Sequence
<220> FEATURE:
<223> OTHER INFORMATION: laboratory made

<400> SEQUENCE: 41
```

| | | | | | |
|---|---|---|---|---|---|
| atggactgga | tctggcggat | cctgtttctc | gtgggagctg | ccacaggcgc | tcattctgct | 60 |
| cagcctgccg | atatccagat | gacccagaca | caagcagcc | tgagcgcctc | tctgggcgat | 120 |
| agagtgacaa | tcagctgcag | agccagccag | gacatcagca | agtacctgaa | ctggtatcag | 180 |
| cagaaacccg | acggcaccgt | gaagctgctg | atctaccaca | caagcagact | gcacagcggc | 240 |
| gtgccaagca | gattttctgg | cagcggcagc | ggcaccgatt | acagcctgac | catcagcaac | 300 |
| ctggaacagg | aagatatcgc | tacctacttc | tgtcagcaag | gcaacaccct | gccttacacc | 360 |
| tttggcggcg | gaacaaagct | ggaactgaaa | agaggcggcg | gaggaagcgg | aggcggagga | 420 |
| tctggggggcg | gaggctctgg | cggaggggga | tctgaagtgc | agctgcagca | gtctggacct | 480 |
| ggactggtgg | ctccttctca | gtccctgtct | gtgacctgta | cagtgtctgg | cgtgtccctg | 540 |
| cctgattacg | gcgtgtcctg | gatcagacag | cctcccagaa | aaggcctgga | atggctggga | 600 |
| gtgatctggg | gcagcgagac | aacctactac | aacagcgccc | tgaagtcccg | gctgaccatc | 660 |
| atcaaggaca | acagcaagag | ccaggtgttc | ctgaagatga | acagcctgca | gaccgacgac | 720 |
| accgccatct | actactgcgc | caagcactac | tactacggcg | gcagctacgc | catggattat | 780 |
| tggggccagg | gcaccaccgt | gacagtgtca | tctgctgctg | ctctgttcgt | gcctgtgttc | 840 |
| ctgcctgcca | gcctacaac | aacaccagcc | ctagacctc | aaccccctgc | cctacaatt | 900 |
| gcctctcagc | tctgtctct | gaggcccgaa | gcttgtagac | tgctgctgg | cggagctgtg | 960 |
| cacaccagag | gactggattt | cgcctgcttt | tgggtgctgg | tggtcgtggg | cggagtgctg | 1020 |
| gcttgttatt | ctctgctggt | caccgtggcc | ttcatcatct | tttggtccg | agtgaagttc | 1080 |
| agcagatccg | ccgatgcccc | tgcttaccag | cagggccaga | atcagctgta | caacgagctg | 1140 |
| aacctgggca | gacgggaaga | gtacgacgtg | ctggataaga | gaagaggcag | agatcccgag | 1200 |

```
atgggcggca agccccagag aagaaagaat ccccaggaag gcctgtataa cgaactgcag    1260
aaagacaaga tggccgaggc ctacagcgag atcggcatga agggcgagag aagaagaggc    1320
aagggccacg atggactgta ccagggactg agcacagcca ccaaggatac ctacgatgcc    1380
ctgcacatgc aggccctgcc tccaagataa                                     1410
```

<210> SEQ ID NO 42
<211> LENGTH: 153
<212> TYPE: PRT
<213> ORGANISM: Artificial Sequence
<220> FEATURE:
<223> OTHER INFORMATION: laboratory made

<400> SEQUENCE: 42

```
Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 43
<211> LENGTH: 160
<212> TYPE: PRT
<213> ORGANISM: Artificial Sequence
<220> FEATURE:
<223> OTHER INFORMATION: laboratory made

<400> SEQUENCE: 43

```
Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110
```

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Gly Ser Glu Lys Asp Glu Leu
145                 150                 155                 160

<210> SEQ ID NO 44
<211> LENGTH: 372
<212> TYPE: PRT
<213> ORGANISM: Artificial Sequence
<220> FEATURE:
<223> OTHER INFORMATION: laboratory made

<400> SEQUENCE: 44

Met Lys Ser Val Leu Val Val Ala Leu Leu Val Ile Phe Gln Val Cys
1               5                   10                  15

Leu Cys Gln Asp Glu Val Thr Asp Asp Tyr Ile Gly Asp Asn Thr Thr
            20                  25                  30

Val Asp Tyr Thr Leu Phe Glu Ser Leu Cys Ser Lys Lys Asp Val Arg
        35                  40                  45

Asn Phe Lys Ala Trp Phe Leu Pro Ile Met Tyr Ser Ile Ile Cys Phe
50                  55                  60

Val Gly Leu Leu Gly Asn Gly Leu Val Val Leu Thr Tyr Ile Tyr Phe
65                  70                  75                  80

Lys Arg Leu Lys Thr Met Thr Asp Thr Tyr Leu Leu Asn Leu Ala Val
                85                  90                  95

Ala Asp Ile Leu Phe Leu Leu Thr Leu Pro Phe Trp Ala Tyr Ser Ala
            100                 105                 110

Ala Lys Ser Trp Val Phe Gly Val His Phe Cys Lys Leu Ile Phe Ala
        115                 120                 125

Ile Tyr Lys Met Ser Phe Phe Ser Gly Met Leu Leu Leu Leu Cys Ile
130                 135                 140

Ser Ile Asp Arg Tyr Val Ala Ile Val Gln Ala Val Ser Ala His Arg
145                 150                 155                 160

His Arg Ala Arg Val Leu Leu Ile Ser Lys Leu Ser Cys Val Gly Ile
                165                 170                 175

Trp Ile Leu Ala Thr Val Leu Ser Ile Pro Glu Leu Leu Tyr Ser Asp
            180                 185                 190

Leu Gln Arg Ser Ser Ser Glu Gln Ala Met Arg Cys Ser Leu Ile Thr
        195                 200                 205

Glu His Val Glu Ala Phe Ile Thr Ile Gln Val Ala Gln Met Val Ile
210                 215                 220

Gly Phe Leu Val Pro Leu Leu Ala Met Ser Phe Cys Tyr Leu Val Ile
225                 230                 235                 240

Ile Arg Thr Leu Leu Gln Ala Arg Asn Phe Glu Arg Asn Lys Ala Ile
                245                 250                 255

Lys Val Ile Ile Ala Val Val Val Phe Ile Val Phe Gln Leu Pro
            260                 265                 270

Tyr Asn Gly Val Val Leu Ala Gln Thr Val Ala Asn Phe Asn Ile Thr
        275                 280                 285

Ser Ser Thr Cys Glu Leu Ser Lys Gln Leu Asn Ile Ala Tyr Asp Val
290                 295                 300

Thr Tyr Ser Leu Ala Cys Val Arg Cys Cys Val Asn Pro Phe Leu Tyr
305                 310                 315                 320

```
Ala Phe Ile Gly Val Lys Phe Arg Asn Asp Leu Phe Lys Leu Phe Lys
                325                 330                 335

Asp Leu Gly Cys Leu Ser Gln Glu Gln Leu Arg Gln Trp Ser Ser Cys
            340                 345                 350

Arg His Ile Arg Arg Ser Ser Met Ser Val Glu Ala Glu Thr Thr Thr
        355                 360                 365

Thr Phe Ser Pro
    370

<210> SEQ ID NO 45
<211> LENGTH: 98
<212> TYPE: PRT
<213> ORGANISM: Artificial Sequence
<220> FEATURE:
<223> OTHER INFORMATION: laboratory made

<400> SEQUENCE: 45

Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser

<210> SEQ ID NO 46
<211> LENGTH: 134
<212> TYPE: PRT
<213> ORGANISM: Artificial Sequence
<220> FEATURE:
<223> OTHER INFORMATION: laboratory made

<400> SEQUENCE: 46

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130
```

<210> SEQ ID NO 47
<211> LENGTH: 1083
<212> TYPE: DNA
<213> ORGANISM: Artificial Sequence
<220> FEATURE:
<223> OTHER INFORMATION: laboratory made

<400> SEQUENCE: 47

| | |
|---|---|
| atggaagatt ttaacatgga gagtgacagc tttgaagatt tctggaaagg tgaagatctt | 60 |
| agtaattaca gttacagctc taccctgccc cctttctac tagatgccgc cccatgtgaa | 120 |
| ccagaatccc tggaaatcaa caagtatttt gtggtcatta tctatgccct ggtattcctg | 180 |
| ctgagcctgc tgggaaactc cctcgtgatg ctggtcatct atacagcag gtcggccgc | 240 |
| tccgtcactg atgtctacct gctgaaccta gccttggccg acctactctt tgccctgacc | 300 |
| ttgcccatct gggccgcctc caaggtgaat ggctggattt ttggcacatt cctgtgcaag | 360 |
| gtggtctcac tcctgaagga agtcaacttc tatagtggca tcctgctact ggcctgcatc | 420 |
| agtgtggacc gttacctggc cattgtccat gccacacgca cactgaccca gaagcgctac | 480 |
| ttggtcaaat tcatatgtct cagcatctgg ggtctgtcct gctcctggc cctgcctgtc | 540 |
| ttacttttcc gaaggaccgt ctactcatcc aatgttagcc cagcctgcta tgaggacatg | 600 |
| ggcaacaata tcagcaaactg gcggatgctg ttacggatcc tgcccagtc ctttggcttc | 660 |
| atcgtgccac tgctgatcat gctgttctgc tacggattca ccctgcgtac gctgtttaag | 720 |
| gcccacatgg ggcagaagca ccgggccatg cgggtcatct ttgctgtcgt cctcatcttc | 780 |
| ctgctctgct ggctgcccta aacctggtc ctgctggcag acaccctcat gaggacccag | 840 |
| gtgatccagg agacctgtga gcgccgcaat cacatcgacc gggctctgga tgccaccgag | 900 |
| attctgggca tccttcacag ctgcctcaac cccctcatct acgccttcat ggccagaag | 960 |
| tttcgccatg gactcctcaa gattctagct atacatggct tgatcagcaa ggactccctg | 1020 |
| cccaaagaca gcaggccttc ctttgttggc tcttcttcag ggcacacttc cactactctc | 1080 |
| taa | 1083 |

<210> SEQ ID NO 48
<211> LENGTH: 360
<212> TYPE: PRT
<213> ORGANISM: Artificial Sequence
<220> FEATURE:
<223> OTHER INFORMATION: laboratory made

<400> SEQUENCE: 48

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
            115                 120                 125

Asn Phe Tyr Ser Gly Ile Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
            195                 200                 205

Met Leu Leu Arg Ile Leu Pro Gln Ser Phe Gly Phe Ile Val Pro Leu
            210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
            275                 280                 285

Arg Asn His Ile Asp Arg Ala Leu Asp Ala Thr Glu Ile Leu Gly Ile
            290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
            355                 360

<210> SEQ ID NO 49
<211> LENGTH: 336
<212> TYPE: DNA
<213> ORGANISM: Artificial Sequence
<220> FEATURE:
<223> OTHER INFORMATION: laboratory made

<400> SEQUENCE: 49
atgtccctgc tcccacgccg cgcccctccg gtcagcatga ggctcctggc ggccgcgctg      60
ctcctgctgc tgctggcgct gtacaccgcg cgtgtggacg gtccaaatg caagtgctcc     120 cggaagggac ccaagatccg ctacagcgac gtgaagaagc tggaaatgaa gccaaagtac     180
ccgcactgcg aggagaagat ggttatcatc accaccaaga gcgtgtccag gtaccgaggt     240
caggagcact gcctgcaccc caagctgcag agcaccaagc gcttcatcaa gtggtacaac     300
gcctggaacg agaagcgcag ggtctacgaa gaatag                              336

<210> SEQ ID NO 50
<211> LENGTH: 111
<212> TYPE: PRT
<213> ORGANISM: Artificial Sequence
<220> FEATURE:
<223> OTHER INFORMATION: laboratory made -continued

<400> SEQUENCE: 50

```
Met Ser Leu Leu Pro Arg Arg Ala Pro Pro Val Ser Met Arg Leu Leu
1               5                  10                  15
Ala Ala Ala Leu Leu Leu Leu Leu Ala Leu Tyr Thr Ala Arg Val
            20                  25                  30
Asp Gly Ser Lys Cys Lys Cys Ser Arg Lys Gly Pro Lys Ile Arg Tyr
        35                  40                  45
Ser Asp Val Lys Lys Leu Glu Met Lys Pro Lys Tyr Pro His Cys Glu
    50                  55                  60
Glu Lys Met Val Ile Ile Thr Thr Lys Ser Val Ser Arg Tyr Arg Gly
65                  70                  75                  80
Gln Glu His Cys Leu His Pro Lys Leu Gln Ser Thr Lys Arg Phe Ile
                85                  90                  95
Lys Trp Tyr Asn Ala Trp Asn Glu Lys Arg Arg Val Tyr Glu Glu
            100                 105                 110
```

<210> SEQ ID NO 51
<211> LENGTH: 1119
<212> TYPE: DNA
<213> ORGANISM: Artificial Sequence
<220> FEATURE:
<223> OTHER INFORMATION: laboratory made

<400> SEQUENCE: 51

```
atgatatttc catggaaatg tcagagcacc cagagggact tatggaacat cttcaagttg    60
tggggggtgga caatgctctg ttgtgatttc ctggcacatc atggaaccga ctgctggact   120
taccattatt ctgaaaaacc catgaactgg caaagggcta agagattctg ccgagacaat   180
tacacagatt tagttgccat acaaaacaag gcggaaattg agtatctgga gaagactctg   240
cctttcagtc gttcttacta ctggatagga tccggaaga taggaggaat atggacgtgg    300
gtgggaacca acaaatctct tactgaagaa gcagagaact ggggagatgg tgagcccaac   360
aacaagaaga acaaggagga ctgcgtggag atctatatca agagaaacaa agatgcaggc   420
aaatggaacg atgacgcctg ccacaaacta aaggcagccc tctgttcac agcttcttgc    480
cagccctggt catgcagtgg ccatggagaa tgtgtagaaa tcatcaataa ttacacctgc   540
aactgtgatg tggggtacta tgggccccag tgtcagtttg tgattcagtg tgagcctttg   600
gaggccccag agctgggtac catggactgt actcaccctt tggaaacttt cagcttcagc   660
tcacagtgtg ccttcagctg ctctgaagga acaaacttaa ctgggattga gaaaccacc    720
tgtggaccat ttggaaactg gtcatctcca gaaccaacct gtcaagtgat tcagtgtgag   780
cctctatcag caccagattt ggggatcatg aactgtagcc atcccctggc cagcttcagc   840
tttacctctg catgtacctt catctgctca gaaggaactg agttaattgg gaagaagaaa   900
accatttgtg aatcatctgg aatctggtca atcctagtc caatatgtca aaaattggac    960
aaaagtttct caatgattaa ggagggtgat tataacccc tcttcattcc agtggcagtc   1020
atggttactg cattctctgg gttggcattt atcatttggc tggcaaggag attaaaaaaa   1080
ggcaagaaat ccaagagaag tatgaatgac ccatattaa                          1119
```

<210> SEQ ID NO 52
<211> LENGTH: 372
<212> TYPE: PRT
<213> ORGANISM: Artificial Sequence
<220> FEATURE:
<223> OTHER INFORMATION: laboratory made

<400> SEQUENCE: 52

```
Met Ile Phe Pro Trp Lys Cys Gln Ser Thr Gln Arg Asp Leu Trp Asn
1               5                   10                  15

Ile Phe Lys Leu Trp Gly Trp Thr Met Leu Cys Cys Asp Phe Leu Ala
            20                  25                  30

His His Gly Thr Asp Cys Trp Thr Tyr His Tyr Ser Glu Lys Pro Met
        35                  40                  45

Asn Trp Gln Arg Ala Arg Arg Phe Cys Arg Asp Asn Tyr Thr Asp Leu
    50                  55                  60

Val Ala Ile Gln Asn Lys Ala Glu Ile Glu Tyr Leu Glu Lys Thr Leu
65                  70                  75                  80

Pro Phe Ser Arg Ser Tyr Tyr Trp Ile Gly Ile Arg Lys Ile Gly Gly
                85                  90                  95

Ile Trp Thr Trp Val Gly Thr Asn Lys Ser Leu Thr Glu Glu Ala Glu
            100                 105                 110

Asn Trp Gly Asp Gly Glu Pro Asn Asn Lys Asn Lys Glu Asp Cys
        115                 120                 125

Val Glu Ile Tyr Ile Lys Arg Asn Lys Asp Ala Gly Lys Trp Asn Asp
    130                 135                 140

Asp Ala Cys His Lys Leu Lys Ala Ala Leu Cys Tyr Thr Ala Ser Cys
145                 150                 155                 160

Gln Pro Trp Ser Cys Ser Gly His Gly Glu Cys Val Glu Ile Ile Asn
                165                 170                 175

Asn Tyr Thr Cys Asn Cys Asp Val Gly Tyr Tyr Gly Pro Gln Cys Gln
            180                 185                 190

Phe Val Ile Gln Cys Glu Pro Leu Glu Ala Pro Glu Leu Gly Thr Met
        195                 200                 205

Asp Cys Thr His Pro Leu Gly Asn Phe Ser Phe Ser Ser Gln Cys Ala
    210                 215                 220

Phe Ser Cys Ser Glu Gly Thr Asn Leu Thr Gly Ile Glu Glu Thr Thr
225                 230                 235                 240

Cys Gly Pro Phe Gly Asn Trp Ser Ser Pro Glu Pro Thr Cys Gln Val
                245                 250                 255

Ile Gln Cys Glu Pro Leu Ser Ala Pro Asp Leu Gly Ile Met Asn Cys
            260                 265                 270

Ser His Pro Leu Ala Ser Phe Ser Phe Thr Ser Ala Cys Thr Phe Ile
        275                 280                 285

Cys Ser Glu Gly Thr Glu Leu Ile Gly Lys Lys Thr Ile Cys Glu
    290                 295                 300

Ser Ser Gly Ile Trp Ser Asn Pro Ser Pro Ile Cys Gln Lys Leu Asp
305                 310                 315                 320

Lys Ser Phe Ser Met Ile Lys Glu Gly Asp Tyr Asn Pro Leu Phe Ile
                325                 330                 335

Pro Val Ala Val Met Val Thr Ala Phe Ser Gly Leu Ala Phe Ile Ile
            340                 345                 350

Trp Leu Ala Arg Arg Leu Lys Lys Gly Lys Lys Ser Lys Arg Ser Met
        355                 360                 365

Asn Asp Pro Tyr
    370
```

<210> SEQ ID NO 53
<211> LENGTH: 300
<212> TYPE: DNA
<213> ORGANISM: Artificial Sequence
<220> FEATURE:
<223> OTHER INFORMATION: laboratory made

<400> SEQUENCE: 53

```
atgacttcca agctggccgt ggctctcttg gcagccttcc tgatttctgc agctctgtgt    60
gaaggtgcag ttttgccaag gagtgctaaa gaacttagat gtcagtgcat aaagacatac   120
tccaaacctt tccacccaa atttatcaaa gaactgagag tgattgagag tggaccacac    180
tgcgccaaca cagaaattat tgtaaagctt tctgatggaa gagagctctg tctggacccc   240
aaggaaaact gggtgcagag ggttgtggag aagtttttga gagggctga gaattcataa   300
```

<210> SEQ ID NO 54
<211> LENGTH: 99
<212> TYPE: PRT
<213> ORGANISM: Artificial Sequence
<220> FEATURE:
<223> OTHER INFORMATION: laboratory made

<400> SEQUENCE: 54

```
Met Thr Ser Lys Leu Ala Val Ala Leu Leu Ala Ala Phe Leu Ile Ser
 1               5                  10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

<210> SEQ ID NO 55
<211> LENGTH: 324
<212> TYPE: DNA
<213> ORGANISM: Artificial Sequence
<220> FEATURE:
<223> OTHER INFORMATION: laboratory made

<400> SEQUENCE: 55

```
atggcccgcg ctgctctctc cgccgccccc agcaatcccc ggctcctgcg agtggcactg    60
ctgctcctgc tcctggtagc cgctggccgg cgcgcagcag gagcgtccgt ggccactgaa   120
ctgcgctgcc agtgcttgca gaccctgcag ggaattcacc ccaagaacat ccaaagtgtg   180
aacgtgaagt cccccggacc ccactgcgcc caaaccgaag tcatagccac actcaagaat   240
gggcggaaag cttgcctcaa tcctgcatcc cccatagtta agaaaatcat cgaaaagatg   300
ctgaacagtg acaaatccaa ctga                                          324
```

<210> SEQ ID NO 56
<211> LENGTH: 107
<212> TYPE: PRT
<213> ORGANISM: Artificial Sequence
<220> FEATURE:
<223> OTHER INFORMATION: laboratory made

<400> SEQUENCE: 56

```
Met Ala Arg Ala Ala Leu Ser Ala Ala Pro Ser Asn Pro Arg Leu Leu
 1               5                  10                  15
```

```
Arg Val Ala Leu Leu Leu Leu Val Ala Ala Gly Arg Arg Ala
         20                  25                  30

Ala Gly Ala Ser Val Ala Thr Glu Leu Arg Cys Gln Cys Leu Gln Thr
             35                  40                  45

Leu Gln Gly Ile His Pro Lys Asn Ile Gln Ser Val Asn Val Lys Ser
 50                  55                  60

Pro Gly Pro His Cys Ala Gln Thr Glu Val Ile Ala Thr Leu Lys Asn
 65                  70                  75                  80

Gly Arg Lys Ala Cys Leu Asn Pro Ala Ser Pro Ile Val Lys Lys Ile
                 85                  90                  95

Ile Glu Lys Met Leu Asn Ser Asp Lys Ser Asn
                100                 105

<210> SEQ ID NO 57
<211> LENGTH: 762
<212> TYPE: DNA
<213> ORGANISM: Artificial Sequence
<220> FEATURE:
<223> OTHER INFORMATION: laboratory made

<400> SEQUENCE: 57
atgtggcccc ctgggtcagc ctcccagcca ccgccctcac ctgccgcggc cacaggtctg      60
catccagcgg ctcgccctgt gtccctgcag tgccggctca gcatgtgtcc agcgcgcagc     120
ctcctccttg tggctaccct ggtcctcctg gaccacctca gtttggccag aaacctcccc     180
gtggccactc cagacccagg aatgttccca tgccttcacc actcccaaaa cctgctgagg     240
gccgtcagca acatgctcca gaaggccaga caaactctag aattttaccc ttgcactttt     300
gaagagattg atcatgaaga tatcacaaaa gataaaacca gcacagtgga ggcctgttta     360
ccattggaat taaccaagaa tgagagttgc ctaaattcca gagagacctc tttcataact     420
aatgggagtt gcctggcctc cagaaagacc tcttttatga tggccctgtg ccttagtagt     480
atttatgaag acttgaagat gtaccaggtg gagttcaaga ccatgaatgc aaagcttctg     540
atggatccta gaggcagat ctttctagat caaaacatgc tggcagttat tgatgagctg     600
atgcaggccc tgaatttcaa cagtgagact gtgccacaaa atcctccct tgaagaaccg     660 gatttttata aaactaaaat caagctctgc atacttcttc atgctttcag aattcgggca     720
gtgactattg atagagtgat gagctatctg aatgcttcct aa                       762

<210> SEQ ID NO 58
<211> LENGTH: 253
<212> TYPE: PRT
<213> ORGANISM: Artificial Sequence
<220> FEATURE:
<223> OTHER INFORMATION: laboratory made

<400> SEQUENCE: 58

Met Trp Pro Pro Gly Ser Ala Ser Gln Pro Pro Ser Pro Ala Ala
 1               5                  10                  15

Ala Thr Gly Leu His Pro Ala Ala Arg Pro Val Ser Leu Gln Cys Arg
             20                  25                  30

Leu Ser Met Cys Pro Ala Arg Ser Leu Leu Leu Val Ala Thr Leu Val
         35                  40                  45

Leu Leu Asp His Leu Ser Leu Ala Arg Asn Leu Pro Val Ala Thr Pro
     50                  55                  60

Asp Pro Gly Met Phe Pro Cys Leu His His Ser Gln Asn Leu Leu Arg
 65                  70                  75                  80
```

```
Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250

<210> SEQ ID NO 59
<211> LENGTH: 987
<212> TYPE: DNA
<213> ORGANISM: Artificial Sequence
<220> FEATURE:
<223> OTHER INFORMATION: laboratory made

<400> SEQUENCE: 59
atgtgtcacc agcagttggt catctcttgg ttttccctgg tttttctggc atctcccctc      60
gtggccatat gggaactgaa gaaagatgtt tatgtcgtag aattggattg gtatccggat     120 gccoctggag aaatggtggt cctcacctgt gacaccoctg aagaagatgg tatcacctgg     180
accttggacc agagcagtga ggtcttaggc tctggcaaaa ccctgaccat ccaagtcaaa     240
gagtttggag atgctggcca gtacacctgt cacaaaggag cgaggttct aagccattcg      300 ctcctgctgc ttcacaaaaa ggaagatgga atttggtcca ctgatatttt aaaggaccag     360
aaagaaccca aaataagac ctttctaaga tgcgaggcca gaattattc tggacgtttc       420 acctgctggt ggctgacgac aatcagtact gatttgacat tcagtgtcaa aagcagcaga    480
ggctcttctg accccaagg ggtgacgtgc ggagctgcta cactctctgc agagagagtc     540 agagggggaca acaaggagta tgagtactca gtggagtgcc aggaggacag tgcctgccca    600
gctgctgagg agagtctgcc cattgaggtc atggtggatg ccgttcacaa gctcaagtat     660
gaaaactaca ccagcagctt cttcatcagg gacatcatca aacctgaccc acccaagaac    720
ttgcagctga agccattaaa gaattctcgg caggtggagg tcagctggga gtaccctgac    780
acctggagta ctccacattc ctacttctcc ctgacattct gcgttcaggt ccagggcaag    840
agcaagagag aaaagaaaga tagagtcttc acggacaaga cctcagccac ggtcatctgc    900
cgcaaaaatg ccagcattag cgtgcgggcc caggaccgct actatagctc atcttggagc    960
gaatgggcat ctgtgccctg cagttag                                         987
```

<210> SEQ ID NO 60
<211> LENGTH: 328
<212> TYPE: PRT
<213> ORGANISM: Artificial Sequence
<220> FEATURE:
<223> OTHER INFORMATION: laboratory made

<400> SEQUENCE: 60

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325
```

<210> SEQ ID NO 61
<211> LENGTH: 536
<212> TYPE: PRT
<213> ORGANISM: Artificial Sequence
<220> FEATURE:
<223> OTHER INFORMATION: laboratory made

<400> SEQUENCE: 61

Met Gly His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
            85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
            165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
    195                 200                 205

Glu Val Met Val Asp Ala Val His Lys Leu Lys Tyr Glu Asn Tyr Thr
            210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
    275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Val Pro Gly Val Gly Val Pro Gly
            325                 330                 335

Val Gly Ala Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
    355                 360                 365

Leu Gln Lys Ala Arg Gln Thr Leu Glu Phe Tyr Pro Cys Thr Ser Glu
            370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser

```
                    405                 410                 415
Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Ser
            435                 440                 445

Lys Met Tyr Gln Val Glu Phe Lys Thr Met Asn Ala Lys Leu Leu Met
            450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
            515                 520                 525

Val Met Ser Tyr Leu Asn Ala Ser
            530                 535

<210> SEQ ID NO 62
<211> LENGTH: 1611
<212> TYPE: DNA
<213> ORGANISM: Artificial Sequence
<220> FEATURE:
<223> OTHER INFORMATION: laboratory made

<400> SEQUENCE: 62
atgggtcacc agcagttggt catctcttgg tttccctgg ttttctggc atctcccctc      60 gtggccatat gggaactgaa gaaagatgtt tatgtcgtag aattggattg gtatccggat     120
gcccctggag aaatggtggt cctcacctgt gacaccctg aagaagatgg tatcacctgg     180
accttggacc agagcagtga ggtcttaggc tctggcaaaa ccctgaccat ccaagtcaaa     240
gagtttggaa tgctggcca gtacacctgt cacaaaggag cgaggttct aagccattcg      300 ctcctgctgc ttcacaaaaa ggaagatgga atttggtcca ctgatatttt aaaggaccag    360
aaagaaccca aaaataagac ctttctaaga tgcgaggcca agaattattc tggacgtttc    420
acctgctggt ggctgacgac aatcagtact gatttgacat tcagtgtcaa aagcagcaga    480
ggctcttctg acccccaagg ggtgacgtgc ggagctgcta cactctctgc agagagagtc    540
agaggggaca caaggagta tgagtactca gtggagtgcc aggaggacag tgcctgccca    600
gctgctgagg agagtctgcc cattgaggtc atggtggatg ccgttcacaa gctcaagtat   660
gaaaactaca ccagcagctt cttcatcagg gacatcatca aacctgaccc acccaagaac   720
ttgcagctga agccattaaa gaattctcgg caggtggagg tcagctggga gtaccctgac    780
acctggagta ctccacattc ctacttctcc ctgacattct gcgttcaggt ccagggcaag    840
agcaagagag aaaagaaaga tagagtcttc acggacaaga cctcagccac ggtcatctgc   900
cgcaaaaatg ccagcattag cgtgcgggcc caggaccgct actatagctc atcttggagc    960
gaatgggcat ctgtgccctg cagtgttcct ggagtagggg tacctggggt gggcgccaga   1020
aacctccccg tggccactcc agacccagga atgttcccat gccttcacca ctcccaaaac   1080
ctgctgaggg ccgtcagcaa catgctccag aaggccagac aaactctaga attttaccct    1140
tgcacttctg aagagattga tcatgaagat atcacaaaag ataaaaccag cacagtggag    1200
gcctgtttac cattggaatt aaccaagaat gagagttgcc taaattccag agagacctct    1260
ttcataacta tgggagttg cctggcctcc agaaagacct cttttatgat ggccctgtgc    1320
```

```
cttagtagta tttatgaaga ctcgaagatg taccaggtgg agttcaagac catgaatgca    1380
aagcttctga tggatcctaa gaggcagatc tttctagatc aaaacatgct ggcagttatt    1440
gatgagctga tgcaggccct gaatttcaac agtgagactg tgccacaaaa atcctccctt    1500
gaagaaccgg attttataaa aactaaaatc aagctctgca tacttcttca tgctttcaga    1560
attcgggcag tgactattga tagagtgatg agctatctga atgcttccta a              1611

<210> SEQ ID NO 63
<211> LENGTH: 477
<212> TYPE: DNA
<213> ORGANISM: Artificial Sequence
<220> FEATURE:
<223> OTHER INFORMATION: laboratory made

<400> SEQUENCE: 63
atgggtcggg ggctgctcag gggcctgtgg ccgctgcaca tcgtcctgtg gacgcgtatc      60
gccagcacga tcccaccgca cgttcagaag tcggttaata cgacatgat agtcactgac      120 aacaacggtg cagtcaagtt tccacaactg tgtaaatttt gtgatgtgag attttccacc     180
tgtgacaacc agaaatcctg catgagcaac tgcagcatca cctccatctg tgagaagcca     240
caggaagtct gtgtggctgt atggagaaag aatgacgaga acataacact agagacagtt     300
tgccatgacc ccaagctccc ctaccatgac tttattctgg aagatgctgc ttctccaaag     360
tgcattatga aggaaaaaaa aaagcctggt gagactttct tcatgtgttc ctgtagctct     420
gatgagtgca atgacaacat catcttctca gaagaatata acaccagcaa tcctgac        477

<210> SEQ ID NO 64
<211> LENGTH: 159
<212> TYPE: PRT
<213> ORGANISM: Artificial Sequence
<220> FEATURE:
<223> OTHER INFORMATION: laboratory made

<400> SEQUENCE: 64

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp
145                 150                 155

<210> SEQ ID NO 65
```

-continued

<211> LENGTH: 933
<212> TYPE: DNA
<213> ORGANISM: Artificial Sequence
<220> FEATURE:
<223> OTHER INFORMATION: laboratory made

<400> SEQUENCE: 65

```
atgggtcggg ggctgctcag gggcctgtgg ccgctgcaca tcgtcctgtg gacgcgtatc    60
gccagcacga tcccaccgca cgttcagaag tcggttaata cgacatgat agtcactgac   120
aacaacggtg cagtcaagtt tccacaactg tgtaaatttt gtgatgtgag attttccacc   180
tgtgacaacc agaaatcctg catgagcaac tgcagcatca cctccatctg tgagaagcca   240
caggaagtct gtgtggctgt atggagaaag aatgacgaga cataacact agagacagtt   300
tgccatgacc ccaagctccc ctaccatgac tttattctgg aagatgctgc ttctccaaag   360
tgcattatga aggaaaaaaa aaagcctggt gagactttct tcatgtgttc ctgtagctct   420
gatgagtgca atgacaacat catcttctca gaagaatata acaccagcaa tcctgacgga   480
ggtggaggaa gtggaggagg tggaagtggt ggtggaggta gtacgatccc accgcacgtt   540
cagaagtcgg ttaataacga catgatagtc actgacaaca acggtgcagt caagtttcca   600
caactgtgta aattttgtga tgtgagattt tccacctgtg acaaccagaa atcctgcatg   660
agcaactgca gcatcacctc catctgtgag aagccacagg aagtctgtgt ggctgtatgg   720
agaaagaatg acgagaacat aacactagag acagtttgcc atgaccccaa gctccctac   780
catgactta ttctggaaga tgctgcttct ccaaagtgca ttatgaagga aaaaaaaag   840
cctggtgaga ctttcttcat gtgttcctgt agctctgatg agtgcaatga caacatcatc   900
ttctcagaag aatataacac cagcaatcct gac                                933
```

<210> SEQ ID NO 66
<211> LENGTH: 311
<212> TYPE: PRT
<213> ORGANISM: Artificial Sequence
<220> FEATURE:
<223> OTHER INFORMATION: laboratory made

<400> SEQUENCE: 66

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Gly
145                 150                 155                 160
```

```
Gly Gly Gly Ser Gly Gly Gly Ser Gly Gly Gly Ser Thr Ile
            165                 170                 175
Pro Pro His Val Gln Lys Ser Val Asn Asn Asp Met Ile Val Thr Asp
        180                 185                 190
Asn Asn Gly Ala Val Lys Phe Pro Gln Leu Cys Lys Phe Cys Asp Val
            195                 200                 205
Arg Phe Ser Thr Cys Asp Asn Gln Lys Ser Cys Met Ser Asn Cys Ser
210                 215                 220
Ile Thr Ser Ile Cys Glu Lys Pro Gln Glu Val Cys Val Ala Val Trp
225                 230                 235                 240
Arg Lys Asn Asp Glu Asn Ile Thr Leu Glu Thr Val Cys His Asp Pro
                245                 250                 255
Lys Leu Pro Tyr His Asp Phe Ile Leu Glu Asp Ala Ala Ser Pro Lys
                260                 265                 270
Cys Ile Met Lys Glu Lys Lys Lys Pro Gly Glu Thr Phe Phe Met Cys
                275                 280                 285
Ser Cys Ser Ser Asp Glu Cys Asn Asp Asn Ile Ile Phe Ser Glu Glu
            290                 295                 300
Tyr Asn Thr Ser Asn Pro Asp
305                 310

<210> SEQ ID NO 67
<211> LENGTH: 510
<212> TYPE: DNA
<213> ORGANISM: Artificial Sequence
<220> FEATURE:
<223> OTHER INFORMATION: Laboratory made

<400> SEQUENCE: 67
atgcgcatca gcaagcccca cctgcgcagc atcagcatcc agtgctacct gtgcctgctg      60
ctgaacagcc acttcctgac cgaggccggc atccacgtgt tcatcctggg ctgcttcagc     120
gccggcctgc ccaagaccga ggccaactgg gtgaacgtga tcagcgacct gaagaagatc     180
gaggacctga tccagagcat gcacatcgac gccacccctgt acaccgagag cgacgtgcac     240
cccagctgca aggtgaccgc catgaagtgc ttcctgctgg agctgcaggt gatcagcctg     300
gagagcggcg acgccagcat ccacgacacc gtggagaacc tgatcatcct ggccaacaac     360
agcctgagca gcaacggcaa cgtgaccgag agcggctgca aggagtgcga ggagctggag     420
gagaagaaca tcaaggagtt cctgcagagc ttcgtgcaca tcgtgcagat gttcatcaac     480
accagcggct ccgagaagga cgagctgtaa                                     510

<210> SEQ ID NO 68
<211> LENGTH: 1215
<212> TYPE: DNA
<213> ORGANISM: Artificial Sequence
<220> FEATURE:
<223> OTHER INFORMATION: Laboratory made

<400> SEQUENCE: 68
atggactgga tctggcggat tctgtttctc gtgggagctg ccacaggcgc tcattctgct      60
cagcctgcca acatccagat gacccagtct ccatcttctg tgtctgcatc tgtaggagac     120
agagtcacca tcacttgtcg ggcgagtcag gatattagcc gctggttagc ctggtatcag     180
cagaaaccag ggaaagcccc taaactcctg atctatgctg catccagttt gcaaagtggg     240
gtcccatcga ggttcagcgg cagtggatct gggacagatt tcgctctcac tatcagcagc     300
```

```
ctgcagcctg aagattttgc aacttactat tgtcaacagg ctgacagtcg tttctcgatc    360
accttcggcc aagggacacg actggagatt aaaggcggcg gaggaagcgg aggcggagga    420
tctgggggcg gaggctctgg cggagggggga tctgaggtgc agctggtgca gtctggggga   480
ggcttggtac agcctggggg gtccctgaga ctctcctgtg cagcctctgg attcaccttc    540
agtagctata gcatgaactg ggtccgccag gctccaggga aggggctgga gtgggtttca   600
tacattagta gtagtagtag taccatacag tacgcagact ctgtgaaggg ccgattcacc    660
atctccagag acaatgccaa gaactcactg tatctgcaaa tgaacagcct gagagacgag    720
gacacggctg tgtattactg tgcgagaggg gactactact acggtatgga cgtctggggc    780
caagggacca cggtcaccgt gagctcagcg gccgcgctga gcaacagcat catgtacttc    840
agccacttcg tgcctgtgtt cctgcctgcc aagcctacaa caacaccagc ccctagacct    900 ccaaccctg cccctacaat tgcctctcag cctctgtctc tgaggcccga agcttgtaga    960
cctgctgctg gcggagctgt gcacaccaga ggactggatt tcgcctgctt tgggtgctg    1020 gtggtcgtgg gcggagtgct ggcttgttat tctctgctgg tcaccgtggc cttcatcatc    1080
ttttgggtcc gactgaagat ccaggtccga aaggccgcca tcaccagcta cgagaagtct   1140
gatggcgtgt acaccggcct gagcaccaga accaggaaa cctacgagac actgaagcac     1200
gagaagcccc cccag                                                      1215

<210> SEQ ID NO 69
<211> LENGTH: 405
<212> TYPE: PRT
<213> ORGANISM: Artificial Sequence
<220> FEATURE:
<223> OTHER INFORMATION: Laboratory made

<400> SEQUENCE: 69

Met Asp Trp Ile Trp Arg Ile Leu Phe Leu Val Gly Ala Ala Thr Gly
1               5                   10                  15

Ala His Ser Ala Gln Pro Ala Asn Ile Gln Met Thr Gln Ser Pro Ser
            20                  25                  30

Ser Val Ser Ala Ser Val Gly Asp Arg Val Thr Ile Thr Cys Arg Ala
        35                  40                  45

Ser Gln Asp Ile Ser Arg Trp Leu Ala Trp Tyr Gln Gln Lys Pro Gly
    50                  55                  60

Lys Ala Pro Lys Leu Leu Ile Tyr Ala Ala Ser Ser Leu Gln Ser Gly
65                  70                  75                  80

Val Pro Ser Arg Phe Ser Gly Ser Gly Ser Gly Thr Asp Phe Ala Leu
                85                  90                  95

Thr Ile Ser Ser Leu Gln Pro Glu Asp Phe Ala Thr Tyr Tyr Cys Gln
            100                 105                 110

Gln Ala Asp Ser Arg Phe Ser Ile Thr Phe Gly Gln Gly Thr Arg Leu
        115                 120                 125

Glu Ile Lys Gly Gly Gly Gly Ser Gly Gly Gly Gly Ser Gly Gly Gly
    130                 135                 140

Gly Ser Gly Gly Gly Gly Ser Glu Val Gln Leu Val Gln Ser Gly Gly
145                 150                 155                 160

Gly Leu Val Gln Pro Gly Gly Ser Leu Arg Leu Ser Cys Ala Ala Ser
                165                 170                 175

Gly Phe Thr Phe Ser Ser Tyr Ser Met Asn Trp Val Arg Gln Ala Pro
            180                 185                 190

Gly Lys Gly Leu Glu Trp Val Ser Tyr Ile Ser Ser Ser Ser Ser Thr
```

-continued

```
                195                 200                 205
Ile Gln Tyr Ala Asp Ser Val Lys Gly Arg Phe Thr Ile Ser Arg Asp
        210                 215                 220

Asn Ala Lys Asn Ser Leu Tyr Leu Gln Met Asn Ser Leu Arg Asp Glu
225                 230                 235                 240

Asp Thr Ala Val Tyr Tyr Cys Ala Arg Gly Asp Tyr Tyr Tyr Gly Met
                245                 250                 255

Asp Val Trp Gly Gln Gly Thr Thr Val Thr Val Ser Ser Ala Ala Ala
                260                 265                 270

Leu Ser Asn Ser Ile Met Tyr Phe Ser His Phe Val Pro Val Phe Leu
            275                 280                 285

Pro Ala Lys Pro Thr Thr Thr Pro Ala Pro Arg Pro Pro Thr Pro Ala
        290                 295                 300

Pro Thr Ile Ala Ser Gln Pro Leu Ser Leu Arg Pro Glu Ala Cys Arg
305                 310                 315                 320

Pro Ala Ala Gly Gly Ala Val His Thr Arg Gly Leu Asp Phe Ala Cys
                325                 330                 335

Phe Trp Val Leu Val Val Gly Gly Val Leu Ala Cys Tyr Ser Leu
                340                 345                 350

Leu Val Thr Val Ala Phe Ile Ile Phe Trp Val Arg Leu Lys Ile Gln
            355                 360                 365

Val Arg Lys Ala Ala Ile Thr Ser Tyr Glu Lys Ser Asp Gly Val Tyr
        370                 375                 380

Thr Gly Leu Ser Thr Arg Asn Gln Glu Thr Tyr Glu Thr Leu Lys His
385                 390                 395                 400

Glu Lys Pro Pro Gln
                405
```

CELL-MEDIATED TRANSIENT DELIVERY OF IMMUNE-ENHANCING MOLECULES INTO THE TUMOR MICROENVIRONMENT

This application claims priority to and the benefit of U.S. Provisional Application No. 62/938,201 filed on Nov. 20, 2019, the entire content of which is incorporated herein by reference.

INCORPORATION BY REFERENCE

The instant application contains a Sequence Listing which has been submitted in ASCII format via EFS-Web and is hereby incorporated by reference in its entirety. Said ASCII copy was created on Nov. 2, 2020, is named 104077_0017PCT_Seq_listing_ST25, and is 98,502 bytes in size.

FIELD OF THE INVENTION

The field of the invention is the targeting of engineered cells using the cytotoxic activated Natural Killer cell line (NK-92) as the basis to improve immunotherapies to cancer and tumors, and in particular irradiated cells for transient presence of immune-enhancing therapy.

BACKGROUND

The following description includes information that may be useful in understanding the present invention. It is not an admission that any of the information provided herein is prior art or relevant to the presently claimed invention, or that any publication specifically or implicitly referenced is prior art.

Systemic delivery of tumor microenvironment modulators, such as cytokines (IL-2, IL-12, IL-15), chemokines, or antibodies (anti-PD1, anti-CTLA4, TGFbeta blocking Abs) can cause significant side effects due to having to infuse very large doses in order to achieve meaningful local effect, or significant pleiotropic activities, which can also be compounded by a sometimes very long persistence of the infused drug in vivo.

Delivering these modulators in a more targeted way can be achieved through the engineering of cells to either constitutively or inducibly secrete them and providing these cells to the tumor microenvironment either through tumor homing or local injection. However, constitutive expression (e.g., using armored CAR-T cells) may lead to prolonged exposure (as long as the cells persist). Termination of expression may be achieved by killing the secreting cells using an inducible suicide mechanism (e.g. iCasp9). However, such mechanisms do not kill 100% of the cells reliably, and they depend on the systemic administration of an inducer molecule. While transient induction of expression can be achieved, it requires complicated engineering of cells with often proprietary inducible promoters, as well as systemic administration of an inducer molecule. Furthermore, transient expression through loading cells with mRNA ensures that secretion is limited in time, however, the carrier cells will potentially persist and the timing of mRNA translation and protein secretion may be variable for different molecules, and therefore, not suited to all situations.

In order to ensure that an active molecule is not administered at harmful doses or that it is present in meaningful amount at the site(s) where it is needed, local injection of the product can be administered (e.g., intratumor injection, injection in resection space, intradermal). However, the targeted site may be difficult to access (e.g., brain tumors) or it may not be accessible for injection, not defined enough (diffuse tumors), or too multiple (metastases). One way to overcome the localized injection issue is to link the active molecule to a targeting agent, such as an antibody. Antibody-drug conjugates (ADC) are not able to access all parts of the body (such as the brain) and may still display dose-related toxicities. Another approach to localized injection is to make the targeting agent a cell capable of homing to the right site and capable of secreting the active molecule. Immune cells, for example, are able to reach tumor sites in all places of the body. Accordingly, engineering T-cells or NK cells to express the active molecule can be an efficient way of ensuring local delivery in the tumor. T-cells expressing IL-12 (either constitutively or inducibly) have been generated, as well as IL-15 expressing NK-cells. However, since these cells currently are autologous (i.e. from the patient), they can expand in vivo making it difficult to control the amount of active molecule and duration of exposure to the active molecule. While the introduction of suicide systems into engineered cells has been shown to successfully limit expansion in the body, such systems do not achieve 100% complete removal of the engineered cells. Moreover, engineering of autologous T- or NK-cells is labor-intensive and expensive, and limited to a single patient. Efforts to engineer allogeneic T- or NK-cells are ongoing but these cells have a high likelihood of being rejected by the patient's immune system.

In view of the above, there are many existing problems and disadvantages with the therapeutic use of engineered T cells and NK cells in a patient. Thus, there is still a need to improve the function of engineered T-cells or NK cells in order to effectively target these cells and their immune active molecule therapy to the tumor microenvironment while limiting overexposure of the therapy in the patient.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

SUMMARY OF THE INVENTION

The inventive subject matter provides a composition and methods in which a recombinant natural killer (NK) cell or T-cell is irradiated to thereby confer transient anti-tumor treatment to a subject and limiting adverse effects in the treatment of a tumor in the subject.

For effective targeting to a tumor microenvironment, the recombinant NK cell or T-cell to be irradiated is transfected with one or more recombinant nucleic acids. Preferably, the NK cell or T-cell to be irradiated is transfected with one or more recombinant nucleic acids encoding i) a homing receptor and/or cytokine, ii) an antigen binding protein (ABP) or chimeric antigen receptor (CAR) that specifically binds to a target antigen, iii) an Fc Receptor, and/or iv) a secreted immune modulator, wherein the one or more nucleic acids are operably linked to a promoter. In more preferred embodiments, the recombinant NK cell or T-cell is a NK-92 cell and the transfected nucleic acid is a tricistronic or quadricistronic vector with expression controlled by single promoter. Most preferably, the recombinant NK-92 cells to be irradiated are transfected with a quadricistronic vector encoding i) a cytokine, ii) an antigen binding protein (ABP) or chimeric antigen receptor (CAR) that specifically binds to a target antigen, iii) an Fc Receptor, and iv) a secreted immune modulator selected from a TGFβ inhibitor and/or IL-12.

In typical embodiments, the TGF-beta inhibitor is a TGF-beta trap. Additionally, the TGF-beta trap may comprise an extracellular domain of a TGFβRII molecule. More specifically, the TGF-beta trap comprises a single chain dimer of the TGF-beta Receptor II ectodomain (TGFbetaRIIecd).

Additionally or alternatively, the cytokine transfected in the recombinant NK cell or T-cell cell to be irradiated is IL2, IL-15, er-IL2, or er-IL15.

Additionally or alternatively with the above, the antigen binding protein transfected in the recombinant NK cell or T-cell to be irradiated specifically binds a tumor associated antigen. Typically, the tumor associated antigen is selected from CD19, CD20, GD2, HER-2, CD30, EGFR, FAP, CD33, CD123, PD-L1, IGF1R, CSPG4, or B7-H4.

Additionally or alternatively with the above, the antigen binding protein transfected in the the recombinant NK cell or T-cell to be irradiated binds an immune modulator protein in a tumor. Examples of immune modulator proteins in a tumor include CTLA-4, PD-1, IDO-1, CD39, or CD73.

Additionally or alternatively with the above, the Fc Receptor transfected in the recombinant NK cell or T-cell to be irradiated is CD16 or a high affinity CD16.

Additionally or alternatively with the above, the antigen binding protein transfected in the recombinant NK cell or T-cell to be irradiated comprises the chimeric antigen receptor (CAR).

Additionally or alternatively with the above, the promoter transfected in the recombinant NK cell or T-cell to be irradiated comprises at least one nuclear factor of activated T (NFAT) binding domain.

In some embodiments, the homing receptor is a G protein-coupled receptor (GPCR), a chemokine receptor, a cytokine receptor, a cell adhesion molecule, a selectin, or an integrin.

Aspects of the inventive subject matter also include a composition of the recombinant NK cell or T-cell irradiated as disclosed herein in combination with a pharmaceutically acceptable excipient.

Aspects of the inventive subject matter also include a method of treating a cancer or a tumor in a subject, the method including administering to the subject a therapeutically effective amount of the irradiated recombinant NK cell or T-cells and compositions as disclosed herein, wherein administration treats the cancer or reduces the size of the tumor in the subject. In typical embodiments, the irradiated recombinant NK cell or T-cells do not proliferate after exposure to irradiation and have transient activity. For example, the irradiated recombinant NK cell or T-cells transfected with one or more recombinant nucleic acids encoding i) a homing receptor and/or cytokine, ii) an antigen binding protein (ABP) or chimeric antigen receptor (CAR) that specifically binds to a target antigen, iii) an Fc Receptor, and/or iv) a secreted immune modulator confer anti-tumor activity for up to 72 hours, for example, up to 48 hours.

In preferred embodiments, methods of treating a cancer or a tumor in a subject include administering to the subject a therapeutically effective amount of the irradiated recombinant NK-92 cells as disclosed herein which are stably transfected with one or more recombinant nucleic acids encoding i) a homing receptor and/or a cytokine, ii) an antigen binding protein (ABP) or chimeric antigen receptor (CAR) that specifically binds to a target antigen, iii) an Fc Receptor, and/or iv) a secreted immune modulator, wherein the one or more nucleic acids are operably linked to a promoter. More preferably, the irradiated recombinant NK-92 cells are transfected with a quadricistronic vector encoding i) a cytokine, ii) an antigen binding protein (ABP) or chimeric antigen receptor (CAR) that specifically binds to a target antigen, iii) an Fc Receptor, and iv) a secreted TGFβ inhibitor and/or IL-12.

Similar aspects of the inventive subject matter also include a method of reducing cancer metastasis in a subject including administering a therapeutically effective amount of the irradiated modified NK-92 cells or compositions as disclosed herein to the subject, thereby reducing cancer metastasis in the subject.

In preferred embodiments, methods of administering of the irradiated modified NK-92 cells or compositions as disclosed herein wherein $1\times10^3$ to $1\times10^{10}$, per $m^2$ of the modified NK-92 cells are administered to the subject. Additionally, administration of the irradiated modified NK-92 cells and compositions include administration parenterally, intravenously, peritumorally, or by infusion.

In exemplary embodiments, a method of reducing cancer metastasis, tumor size, and/or decrease in cancer cells in a patient includes administering the irradiated recombinant NK-92 cell disclosed herein, wherein prior to irradiation, the NK-92 cell is transfected with a recombinant nucleic acid encoding a secreted immune modulator, a chemokine or a cytokine receptor, and/or an antigen binding protein or chimeric antigen receptor (CAR) that specifically binds to a target antigen, all of which are operably linked to a promoter. More specifically, the secreted immune modulator includes IL-12 and/or a TGF-beta inhibitor. Preferably the TGF-beta inhibitor is a TGF-beta trap. In preferred embodiments, the modified NK-92 cell to be irradiated is transfected with a quadricistronic vector encoding i) a cytokine comprising IL-2 or IL-15, ii) an antigen binding protein (ABP) or chimeric antigen receptor (CAR) that specifically binds to a target antigen, iii) an Fc Receptor, and iv) a secreted immune modulator selected from a TGFβ inhibitor and/or IL-12.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 5B is a table of the raw data collected for the PD-L1 t-haNK cells as graphed in FIG. 5A.

DETAILED DESCRIPTION

The inventors have surprisingly discovered that irradiation of recombinant (i.e., engineered or modified allogeneic) T- or NK-cells as disclosed herein can maintain therapeutic effectiveness of these immune therapy delivery cells for treatment of cancer tumors in a patient while also limiting overexposure and side effects in the patient. In particular, the inventors advantageously discovered that irradiated NK cells engineered to express a secreted immune modulator are effectively inhibited from replication (e.g., cell proliferation) while maintaining transient activity of the irradiated recombinant NK cell including transient activity of the secreted immune modulator(s). One should appreciate that limiting patient overexposure and/or side effects of an allogeneic cellular therapy is indeed desirable for engineered tumor-targeted cells.

Considering allogeneic cells such as a recombinant NK cell can induce harmful effects when infused in a subject (e.g., a cancer patient), it was surprisingly discovered that irradiating allogeneic cells transfected with a nucleic acid encoding a secreted immune modulator (e.g., a TGFβ inhibitor or IL-12) inhibits cell proliferation as expected, while maintaining activity and of the secreted immune modulator for a transient period after irradiation. Unlike cell surface expressed recombinant molecules, secreted cytokines are not membrane-bound and are dependent on the host cells nuclear machinery for expression. Gamma (γ)-irradiation destroys the host cell nuclear machinery, thereby arresting cell proliferation. Additionally, γ-irradiation inhibits expression of genes in pathways related to cell-type specific immunity, and in particular, NK cells. See, Paul et al., 2013, *Radiat. Res.*, 180:575-583. Remarkably, however, γ-irradiated NK cells are capable of expressing a secreted cytokine (e.g., a TGFβ inhibitor or IL-12). Accordingly, γ-irradiation of recombinant NK cells transfected with a quadricistronic vector encoding i) a homing receptor and/or a cytokine, ii) an antigen binding protein (ABP) or chimeric antigen receptor (CAR) that specifically binds to a target antigen, iii) an Fc Receptor, and iv) a secreted immune modulator inhibited the recombinant NK cells from replication while maintaining transient activity of the encoded recombinant molecules including the secreted immune modulators. For example, transient activity was maintained for up to 72 hours, including, for example, up to 48 hours.

Figure 1:
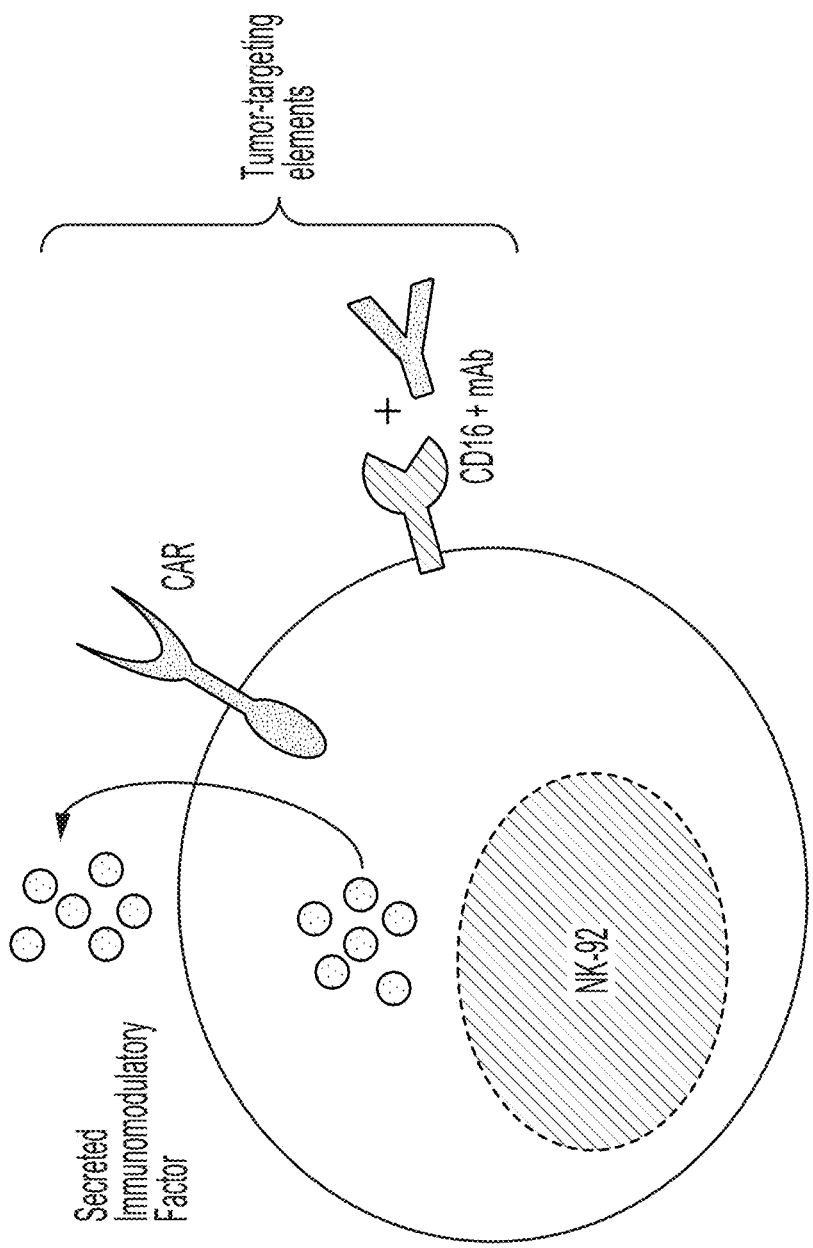
FIG. 1 is a schematic of a genetically modified natural killer (NK-92) cell with possible tumor-targeting elements as indicated.

Accordingly, the contemplated inventive subject matter includes the rendering of and treatment with irradiated tumor-targeted cells (e.g., T-cells or NK-cells) engineered to constitutively express secreted modulators, antigen binding proteins, an Fc Receptor, and a homing receptor or cytokine/chemokine to aide in targeting the tumor. The schematic in FIG. 1 depicts an exemplary tumor targeted cell, the NK-92 cell, having the tumor targeting elements of a chimeric antigen receptor (CAR) and CD16 receptor for targeting a tumor along with secreted immune-modulatory molecules (e.g., TGFβ inhibitor and/or IL-12). Examples of these engineered NK-92 cells capable of homing to a tumor are disclosed, for example, in WO2020/028656, the entire contents of which are herein incorporated by reference. As disclosed herein in more detail, controlled irradiation of allogeneic engineered T- or NK-cells maintains effective therapeutic function of these tumor-targeted cells, while limiting the proliferation of these cells for about 48 to 72 hours (e.g., 2 to 3 days).

Preferably, the engineered NK cells include a cytotoxic activated Natural Killer cell line (e.g., NK-92) as the basis to improve immunotherapies to cancer cells and tumors, and/or to increase homing (migration) towards a target of interest. In some embodiments, the NK-92 cells are engineered to express a homing receptor known to direct lymphocytes to lymph nodes when expressed. In some embodiments, the NK cells are transfected with a nucleic acid encoding a secreted cytokine that modulates the tumor microenvironment or an inhibitor that blocks a cytokine that modulates the tumor microenvironment.

More preferably, prior to irradiation, the NK cells are transfected with a nucleic acid to express a secreted immune modulator (e.g., a TGFβ inhibitor and/or IL-12), and an antigen binding protein (ABP) or chimeric antigen receptor (CAR) that specifically binds to a target antigen (e.g., an anti-PD-L1), and optionally one or both selected from a homing receptor and an Fc Receptor, wherein the nucleic acid is operably linked to a promoter in a tricistronic construct (vector). In an additional preferred embodiment, the NK cells are transfected with a nucleic acid to express a secreted immune modulator (e.g., a TGFβ inhibitor and/or IL-12), an antigen binding protein (ABP) or chimeric antigen receptor (CAR) that specifically binds to a target antigen (e.g., an anti-PD-L1), and an Fc Receptor (e.g., CD16 or CD16-158V), wherein the nucleic acid is operably linked to a promoter in a tricistronic construct (vector). In another preferred embodiment, the NK cells are transfected with a nucleic acid to express a secreted immune modulator (e.g., a TGFβ inhibitor and/or IL-12), an antigen binding protein (ABP) or chimeric antigen receptor (CAR) that specifically binds to a target antigen (e.g., an anti-PD-L1), and a homing receptor, wherein the nucleic acid is operably linked to a promoter in a tricistronic vector.

Most preferably, the NK cells are transfected with a nucleic acid to express a secreted immune modulator (e.g., a TGFβ inhibitor and/or IL-12), a homing receptor, an Fc Receptor (e.g., CD16 or CD16-158V), and an antigen binding protein (ABP) or chimeric antigen receptor (CAR) that specifically binds to a target antigen, wherein the nucleic acid is operably linked to a promoter in a quadricistronic vector.

As disclosed herein, therapeutic function may be determined by assaying the integrity of the cell and the recombinant molecules transfected therein as set forth in FIGS. 2A, 2B, 3, 4A, 4B, 4C, 5A, 5B, 6, 7A, and 7B. Cell integrity may be measured by assaying the presence and/or function of known cellular molecules including recombinant as well as endogenous molecules. For example, with reference to FIG. 7B, the vitality of the cell after irradiation is measured by the presence of intracellular reduced thiols (glutathione; GSH).

Specifically, the allogeneic modified T- or NK-cells may be irradiated with of between 5 to 30 gray (Gy). As understood by persons skilled in the art, the gray is a derived unit of ionizing radiation dose in the International System of Units. The gray (Gy) is defined as the absorption of one joule of radiation energy per kilogram of matter.

To maintain the function of expression of tumor targeting elements while limiting cellular proliferation, engineered allogeneic T- or NK-cells may be irradiated with 5, 6, 7, 8, 9, 10, 11, 12, 13, 14, 15, 16, 17, 18, 19, 20, 21, 22, 23, 24, 25, 26, 27, 28, 29, or 30 Gy. As can be determined by the skilled person, some engineered T- or NK-cells may require irradiation in the range of between 5 to 15 Gy (e.g., 5, 6, 7, 8, 9, 10, 11, 12, 13, 14, or 15 Gy) to maintain therapeutic effectiveness while limiting proliferation of the cells to no more than 72 hours. In still other embodiments, the range of irradiation may be of between 5 to 10 Gy (e.g., 5, 6, 7, 8, 9, or 10 Gy).

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this disclosure.

As used herein, the term "transfect" refers to the insertion of nucleic acid into a cell. Transfection may be performed using any means that allows the nucleic acid to enter the cell. DNA and/or mRNA may be transfected into a cell. Preferably, a transfected cell expresses the gene product (i.e., protein) encoded by the nucleic acid.

The term "homing receptor" refers to a receptor that activates a cellular pathway that results directly or indirectly in the cell migrating toward a target cell or tissue. For example, homing receptors expressed by leukocytes are used by leukocytes and lymphocytes to enter secondary lymphoid tissues via high endothelial venules. Homing receptors can also be used by cells to migrate toward the source of a chemical gradient, such as a chemokine gradient.

Non-limiting examples of homing receptors include G protein-coupled receptors such as chemokine receptors, including but not limited to CCR1, CCR2, CCR3, CCR4, CCR5, CCR6, CCR7, CCR8, CCR9, CCR10, CXCR1, CXCR2, CXCR3, CXCR4, CXCR5, CXCR6, CXCR7, CX3CR1, XCR1, CCXCKR, D6, DARC, or the receptor for CXCL14; cytokine receptors; cell adhesion molecules such as selectins, including L-selectin (CD62L); integrins such as α4β7 integrin, LPAM-1, and LFA-1. Homing receptors generally bind to cognate ligands on the target tissues or cell. In some embodiments, homing receptors bind to Addressins on the endothelium of venules, such as mucosal vascular addressin cell adhesion molecule 1 (MAdCAM-1). In some embodiments, the nucleic acid encoding CCR7 has at least 90%, 91%, 92%, 93%, 94%, 95%, 96%, 97%, 98% or 99% identity to SEQ ID NO:1. In some exemplary embodiments, the chemokines and homing receptors contemplated herein may may comprise a polypeptide sequence or a polynucleotide sequence having at least 80%, 85%, 90%, 91%, 92%, 93%, 94%, 95%, 96%, 97%, 98% or 99% identity to SEQ ID NO: 44 (CCR7 a.a. sequence), or SEQ ID NO: 45 (CCL19 a.a. sequence), or SEQ ID NO: 46 (CCL21 a.a. sequence), or SEQ ID NO: 47 (CXCR2 n.t. sequence), or SEQ ID NO: 48 (CXCR2 a.a. sequence), or SEQ ID NO: 49 (CXCL14 n.t. sequence), or SEQ ID NO: 50 (CXCL14 a.a. sequence), or SEQ ID NO: 51 (CD62L n.t. sequence), or SEQ ID NO: 52 (CD62L a.a. sequence), or SEQ ID NO: 53 (IL-8 n.t. sequence), or SEQ ID NO: 54 (IL-8 a.a. sequence), or SEQ ID NO: 55 (CXCL1 n.t. sequence), or SEQ ID NO: 56 (CXCL1 a.a. sequence).

As used herein, "immunotherapy" refers to the use of NK-92 cells, modified or unmodified, naturally occurring or modified NK cell or T-cell, whether alone or in combination, and which are capable of inducing cytotoxicity when contacting a target cell.

The term "tumor-specific antigen" as used herein refers to antigens that are present on a cancer or neoplastic cell but not detectable on a normal cell derived from the same tissue or lineage as the cancer cell. Tumor-specific antigens, as used herein, also refers to tumor-associated antigens, that is, antigens that are expressed at a higher level on a cancer cell as compared to a normal cell derived from the same tissue or lineage as the cancer cell.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule.

As used herein, "natural killer (NK) cells" are cells of the immune system that kill target cells in the absence of a specific antigenic stimulus, and without restriction according to major histocompatibility complex (MHC) class. NK cells are characterized by the presence of CD56 and the absence of CD3 surface markers.

Figure 2A:
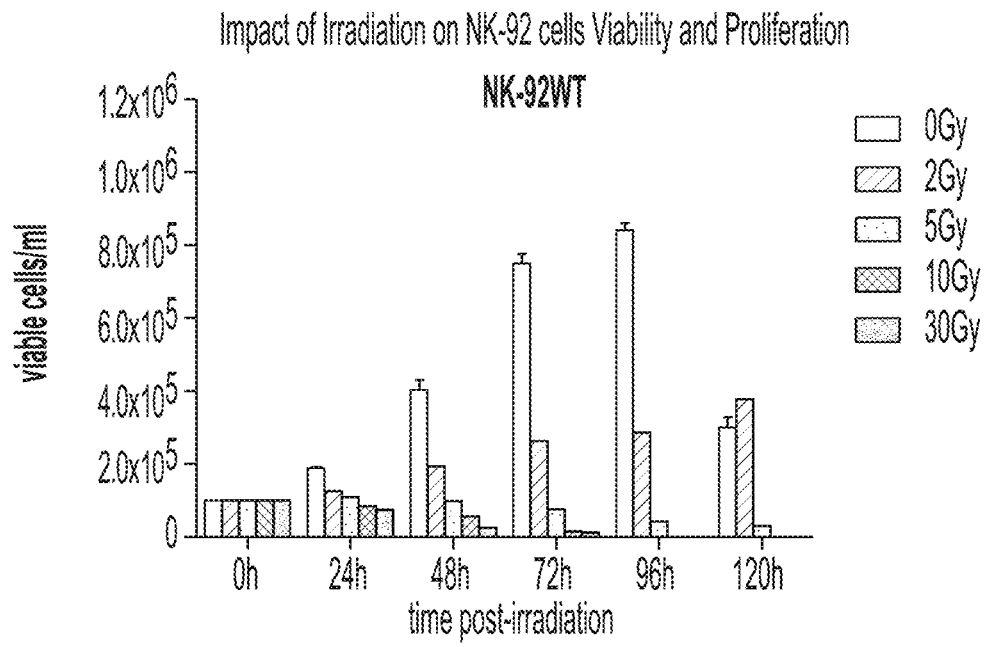
FIG. 2A is a graph of the number of viable wildtype (WT) NK-92 cells at 0, 24, 48, 72, 96, and 120 hours after irradiation at 0, 2, 5, 10, and 30 Gy as indicated.
Figure 2B:
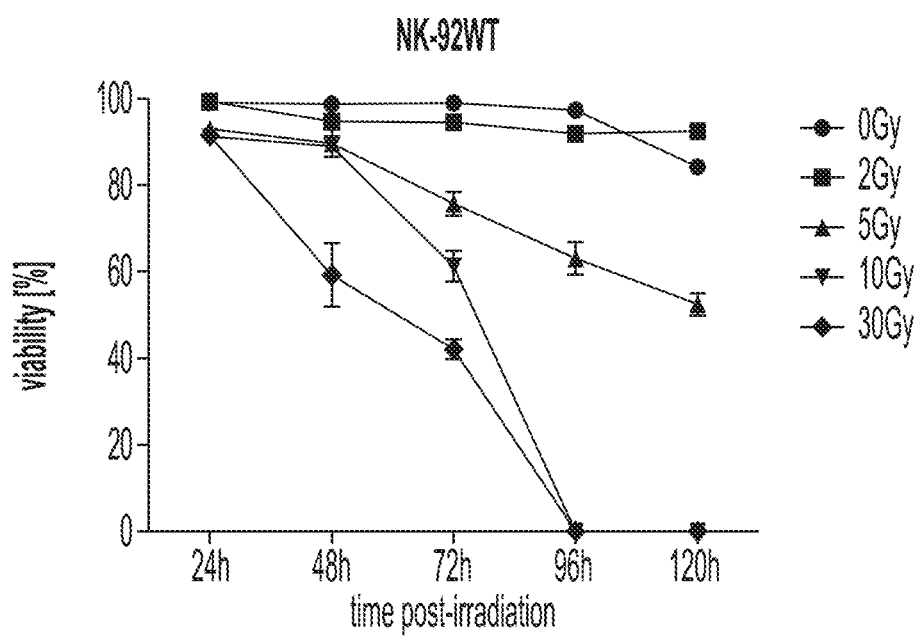
FIG. 2B is a graph of the percent cell viability of the wildtype (WT) NK-92 cells as in FIG. 2A at 0, 24, 48, 72, 96, and 120 hours after irradiation at 0, 2, 5, 10, and 30 Gy as indicated.

The contemplated subject matter includes irradiating recombinant allogeneic NK cells or T-cells with 5 to 30 Gy. Preferably, the recombinant allogeneic cells are NK-92 cells irradiated with 5 to 30 Gy. With reference to FIGS. 2A-2B, cell viability of wild type NK-92 cells was measured after irradiation as indicated. As disclosed and referenced herein, NK-92 cells may be engineered to create unique cell lines that can be grown in culture indefinitely. In clinical trials, they have been shown to be well tolerated by patients and to not induce harmful immune responses. They are available as an "off-the-shelf" product without patient restriction, and therefore more advantageous to use than autologous T- or NK-cells. They can be made to preferentially home to tumor sites, thereby enabling local delivery of secreted molecules. Advantageously, the recombinant NK cells disclosed herein maintain homing, cytotoxic, and secretory functions for 48 to 72 hours after exposure with lethal doses of gamma radiation, but subsequently die, thereby eliminating issues associated with cellular expansion and extended persistence. The recombinant NK cells as disclosed herein can be irradiated and infused repeatedly, which allows control over duration of exposure to the active molecules.

In exemplary embodiments, NK-92 cells to be irradiated may be genetically engineered by transfection or transduction with DNA constructs encoding one or multiple genes. In particular, the inventive subject matter comprises modified NK-92 cells to be irradiated that are capable of modulating the tumor microenvironment. These modified NK-92 cells preferably comprise a multi-cistronic vector comprising one or more nucleic acids encoding i) a homing receptor and/or cytokine, ii) an antigen binding protein (ABP) or chimeric antigen receptor (CAR) that specifically binds to a target antigen, iii) an Fc Receptor (e.g., CD16 or CD16-158V), and/or iv) a secreted immune modulator, wherein the one or more nucleic acids are operably linked to a promoter.

Figure 4A:
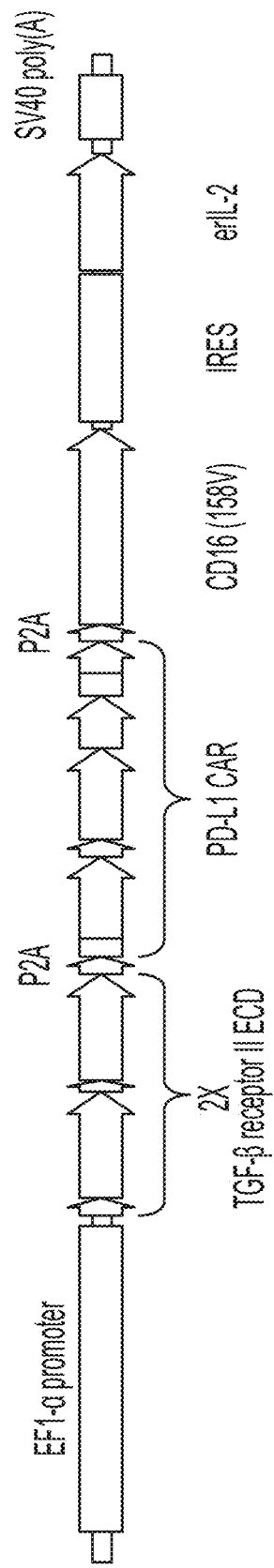
FIG. 4A illustrates one embodiment of a quadricistronic vector encoding a TGFβ-trap armored PD-L1 CAR nucleic acids.
Figure 4B:
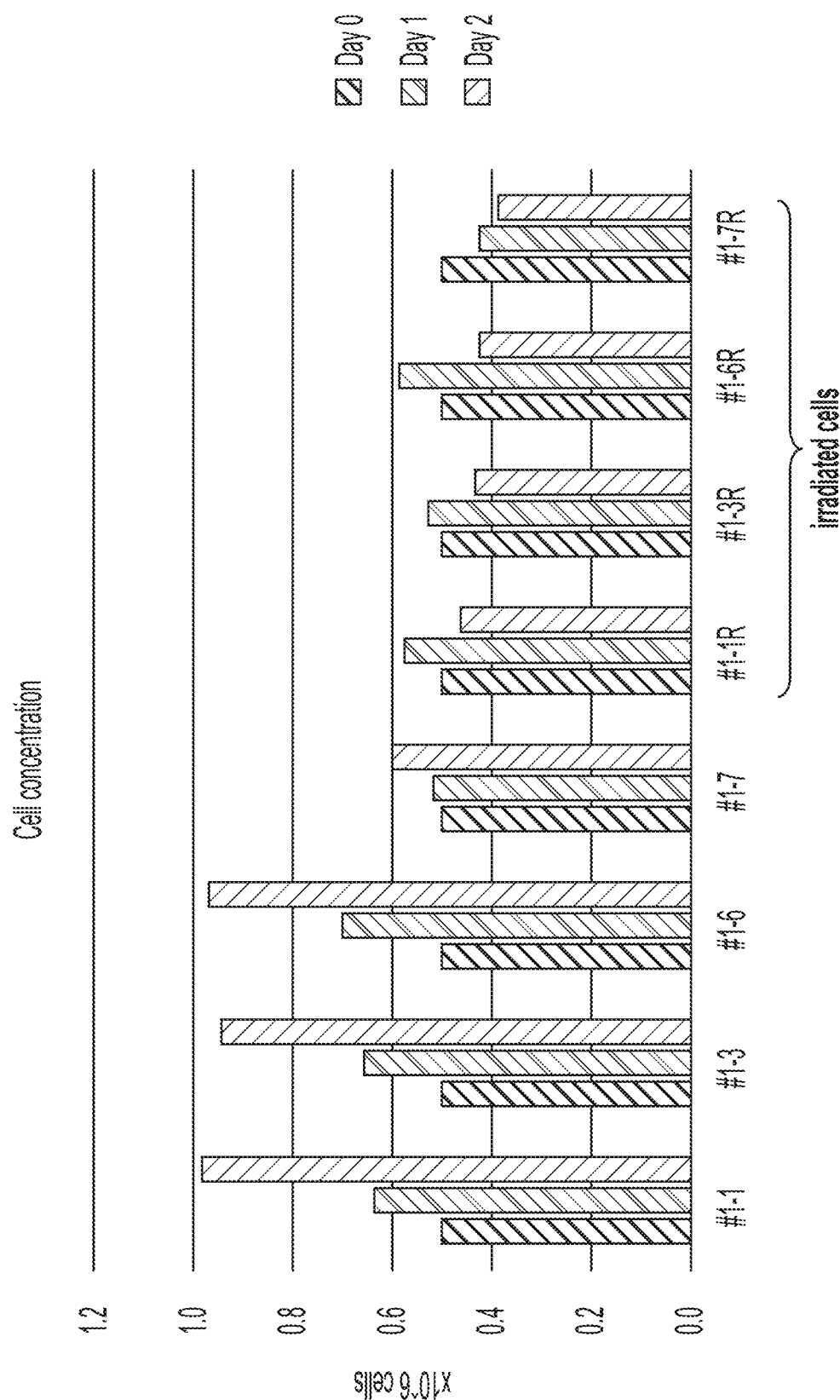
FIG. 4B is a graph of cell concentration of non-irradiated and irradiated t-haNK (NK-92) cells as indicated and further disclosed herein (transfected with the quadricistronic vector or FIG. 4A), with Day 0, Day 1, Day 2 cell counts for each indicated set of cells shown left to right.
Figure 4C:
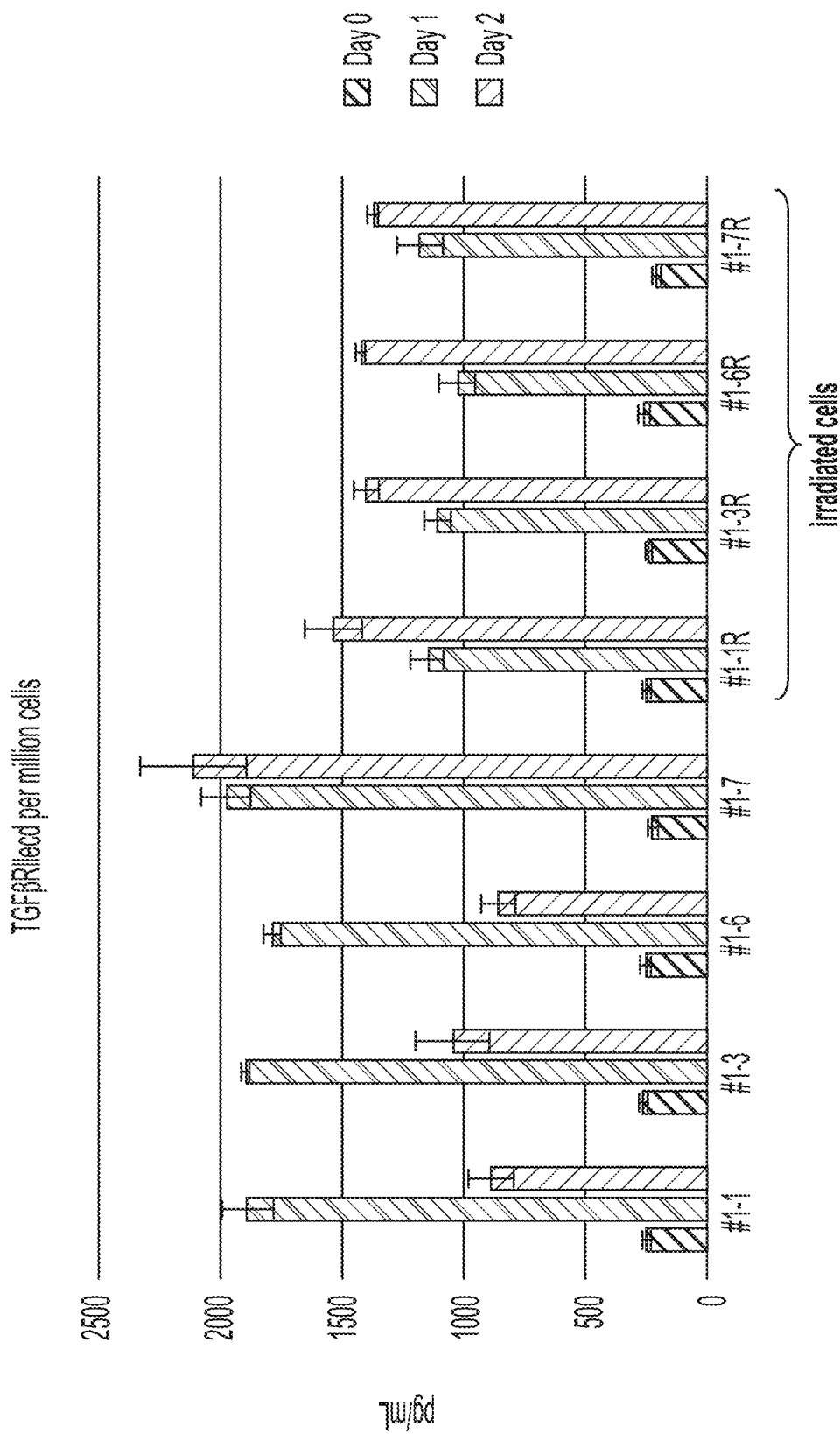
FIG. 4C is a graph of the concentration (pg/mL) of TGFBRIIecd measured per million cells for the non-irradiated and irradiated t-hank (NK-92) cells of FIG. 4B.

Notably, NK-92 cells engineered to constitutively express a secreted TGFbeta-trap molecule or a single chain IL-12 have been found to be able to secrete high quantities of active molecules (in the ng/ml range). Moreover, it has been observed that NK-92 cells have the ability to home to tumor sites, and that homing can be enhanced by expression of a tumor-specific CAR molecule (such as PD-L1 CAR) and/or a chemokine receptor. For example, NK-92 cells engineered to express the CCR7 chemokine receptor have also been shown to home to CCL19-producing tumors more efficiently than parental NK-92 cells. NK-92 cells irradiated with a clinically compatible dose of radiation (e.g., up to 10, 15, 20, or 30 Gy) survive up to 48 hours or up to 72 hours, while being able to maintain cytotoxic and secretory functions (FIG. 4B-4C). Infusion of irradiated engineered NK-92 cells therefore provides a way to control delivery of secreted molecules in space (tumor-homing) as well as in time (because of the limited lifespan of irradiated cells). In some embodiments, recombinant NK-92 cells as disclosed herein that have been irradiated with a clinically compatible dose of 10 or 15 Gy gamma (γ) irradiation survive up to 24, 30, 36, 42, 48, 54, 60, 66, or 72 hours while being able to maintain cytotoxic and secretory functions.

As used herein, the terms "cytotoxic" and "cytolytic," when used to describe the activity of effector cells such as NK-92 cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK-92 cells is due in part to cytolysis.

The term "kill" with respect to a cell/cell population is directed to include any type of manipulation that will lead to the death of that cell/cell population.

The term "NK-92" refers to natural killer cells derived from the highly potent unique cell line described in Gong et al. (1994), rights to which are owned by NantKwest® (hereafter, "NK-92 cells"). The immortal NK cell line was originally obtained from a patient having non-Hodgkin's lymphoma. Unless indicated otherwise, the term "NK-92" is intended to refer to the original NK-92 cell lines as well as NK-92 cell lines that have been modified (e.g., by introduction of exogenous genes). NK-92 cells and exemplary and non-limiting modifications thereof are described in U.S. Pat. Nos. 7,618,817; 8,034,332; 8,313,943; 9,181,322; 9,150,636; and published U.S. application Ser. No. 10/008,955, all of which are incorporated herein by reference in their entireties, and include wild type NK-92, NK-92-CD16, NK-92-CD16-γ, NK-92-CD16-ζ, NK-92-CD16(F176V), NK-92MI, and NK-92-CI. NK-92 cells are known to persons of ordinary skill in the art, to whom such cells are readily available from NantKwest, Inc.

The term "aNK" refers to an unmodified natural killer cells derived from the highly potent unique cell line described in Gong et al. (1994), rights to which are owned by NantKwest (hereafter, "aNK® cells"). The term "haNK" refers to natural killer cells derived from the highly potent unique cell line described in Gong et al. (1994), rights to which are owned by NantKwest, modified to express CD16 on the cell surface (hereafter, "CD16+NK-92 cells" or "haNK cells"). In some embodiments, the CD16+NK-92 cells comprise a high affinity CD16 receptor on the cell surface. An example of a high affinity CD16 includes CD16-F158V. The term "taNK" refers to natural killer cells derived from the highly potent unique cell line described in Gong et al. (1994), rights to which are owned by NantKwest, modified to express a chimeric antigen receptor (hereafter, "CAR-modified NK-92 cells" or "taNK® cells"). The term "t-haNK" refers to natural killer cells derived from the highly potent unique cell line described in Gong et al. (1994), rights to which are owned by NantWest, modified to express CD16 on the cell surface and to express a chimeric antigen receptor (hereafter, "CAR-modified CD16+NK-92 cells" or "t-haNK cells"). In some embodiments, the t-haNK cells express a high affinity CD16 receptor on the cell surface.

In addition, irradiated recombinant NK-92 cells as disclosed herein may also include a promoter having NFAT binding domains (sequence) introduced into the promoter for expression of a cytokine, chemokine, and/or antigen binding protein. NK-92 cells engineered to express a luciferase reporter gene under the control of a nuclear factor of activated T cells (NFAT) transcription factor promoter sequence have been shown to induce high luciferase expression in response to stimulation on activating receptors that signal through the NFAT pathway (such as receptors that recruit CD3ζ or FcθRIγ adaptor molecules). Accordingly, this inducible expression of a secreted molecule is dependent on the cells being activated by a suitable target and does not depend on an external inducer molecule. In one embodiment, the CD3ζ signaling domain contemplated herein may comprise a polypeptide sequence having at least 80%, 85%, 90%, 91%, 92%, 93%, 94%, 95%, 96%, 97%, 98% or 99% identity to SEQ ID NO: 40.

As disclosed in WO2020/028656 (the entire contents of which are herein incorporated by reference) target engagement of susceptible cell lines is shown to be recognized in NK-92 cells by activation of the NFAT transcription factor and its nuclear translocation. Target binding involving the FcεRIγ or CD3zeta pathway (including ADCC or CAR mediated target recognition) is sufficient to induce NFAT activation in NK-92 cells. This was demonstrated by inserting a reporter cassette containing 3 NFAT response elements and a minimal promoter driving firefly luciferase. NFAT activation by the CD3zeta pathway through electroporation of CD19 CAR mRNA into this reporter cell line, followed by co-culture with SUP-B15 (CD19+, but resistant to nonspecific cytotoxicity) resulted in luciferase expression.

In exemplary embodiments, the complete sequence for the NFAT response cassette driving CCL21+Poly-A, and a FRT-embedded blasticidin resistance gene driven by CMV, comprises a polynucleotide sequence having at least 80%, 85%, 90%, 91%, 92%, 93%, 94%, 95%, 96%, 97%, 98% or 99% identity to SEQ ID NO:8.

The term "Fc receptor" refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified based on the type of antibody they recognize. For example, Fc-gamma receptors (FCγR) bind to the IgG class of antibodies. FCγRIII-A (also called CD16) is a low affinity Fc receptor that binds to IgG antibodies and activates ADCC. FCγRIII-A are typically found on NK cells. NK-92 cells do not express FCγRIII-A. Fc-epsilon receptors (FcR) bind to the Fc region of IgE antibodies. In some embodiments, the CD16 receptor comprises a phenylalanine (F) to valine (V) substitution at amino acid position 158 (F158V) of the mature form of the polypeptide (SEQ ID NO: 12) (corresponding to position 176 of the full length form of the polypeptide comprising the signal sequence). In one embodiment, the Fc receptor comprises the nucleic acid sequence of SEQ ID NO:13 or the amino acid sequence of SEQ ID NO:12.

The term "chimeric antigen receptor" (CAR), as used herein, refers to an extracellular antigen-binding domain that is fused to an intracellular signaling domain. CARs can be expressed in T cells or NK cells to increase cytotoxicity. In general, the extracellular antigen-binding domain is a scFv that is specific for an antigen found on a cell of interest. For example, a CAR-expressing NK-92 cell as disclosed herein to be irradiated (e.g., and expressed together with a homing receptor, an Fc receptor, and a secreted cytokine) is targeted to cells expressing certain antigens on the cell surface, based on the specificity of the scFv domain. The scFv domain can be engineered to recognize any antigen, including tumor-specific antigens. For example, CD19-CAR recognizes CD19, a cell surface marker expressed by some cancers.

In additional embodiments, the recombinant CAR comprises a cytoplasmic domain of FcεRIγ. For example, the cytoplasmic domain of FcεRIγ may comprise an amino acid sequence having at least 95% sequence identity to SEQ ID NO: 31. Alternatively, the cytoplasmic domain of FcεRIγ is encoded by a nucleic acid having at least 95% sequence identity to SEQ ID NO:32. In other embodiments, the CAR comprises a hinge region from CD8. In some embodiments, the CAR comprises a transmembrane domain from CD28.

Accordingly, the recombinant NK-29 cells may be transfected with a nucleic acid construct (e.g., quadricistronic vector) that comprises SEQ ID NO:31 (FcεRIγ intracellular cytoplasmic domain), SEQ ID NO:32 (FcεRIγ intracellular signaling domain minus transmembrance domain), SEQ ID NO: 33 (CD8 hinge region), SEQ ID NO: 34 (CD8 hinge region DNA), SEQ ID NO:35 (CD28 transmembrane domain) and/or SEQ ID NO:36 (CD28 transmembrane domain, minus ITAM or intracellular sequence). In one embodiment, the CD8 hinge region, CD28 transmembrane, and FcεRIγ (FceRIgamma) signaling domain amino acid sequence comprises a polypeptide or a polynucleotide sequence having at least 80%, 85%, 90%, 91%, 92%, 93%, 94%, 95%, 96%, 97%, 98% or 99% identity to SEQ ID NO: 37 or SEQ ID NO: 38. In one embodiment, the CAR scFv may comprise a polypeptide sequence having at least 80%, 85%, 90%, 91%, 92%, 93%, 94%, 95%, 96%, 97%, 98% or 99% identity to SEQ ID NO: 39.

Notably, the inventive subject matter includes irradiated modified NK-92 cells that are capable of transiently modulating the tumor microenvironment. The irradiated modified NK-92 cell preferably includes a quadricistronic vector comprising one or more nucleic acids encoding i) IL-12 or a TGF-beta trap, ii) an Antigen Binding Protein (ABP) or Chimeric Antigen Receptor (CAR) that specifically binds to a target antigen, iii) an Fc Receptor such as CD16 or CD16-158V, and/or iv) a cytokine (e.g., erIL-2 or erIL-15), wherein the nucleic acid sequence is operably linked to a promoter.

In another aspect, the secreted cytokine that modulates the tumor microenvironment may be IL-12 or a TGF-beta inhibitor. Accordingly, the nucleic acid construct may encode for IL-12 and/or a TGF-beta inhibitor.

In exemplary embodiments, the IL-12 as contemplated herein may comprise a nucleic acid sequence with at least 80%, 85%, 90%, 91%, 92%, 93%, 94%, 95%, 96%, 97%, 98% or 99% identity to SEQ ID NO: 57 (p35 n.t. sequence), or SEQ ID NO: 59 (p40 n.t. sequence). The IL-12 contemplated herein may also comprise an amino acid sequence with at least 80%, 85%, 90%, 91%, 92%, 93%, 94%, 95%, 96%, 97%, 98% or 99% identity to SEQ ID NO: 58 (p35 a.a. sequence, isoform 1 precursor), or SEQ ID NO: 60 (p40 a.a. sequence, precursor).

In one exemplary embodiment, the IL-12 single chain p40_p35 sequence in IL-2/PD-L1 Quadricistronic vector may include a polypeptide sequence with at least 80%, 85%, 90%, 91%, 92%, 93%, 94%, 95%, 96%, 97%, 98% or 99% identity to SEQ ID NO: 61, or may comprise an polynucleotide sequence with at least 80%, 85%, 90%, 91%, 92%, 93%, 94%, 95%, 96%, 97%, 98% or 99% identity to SEQ ID NO: 62.

TGF-β expression within tumors is known to suppress the antitumor activity of leukocytes in the tumor microenvironment. Thus, in some embodiments, the modified NK-92 cell to be irradiated includes a recombinant nucleic acid construct that encodes a TGF-beta inhibitor, for example a peptide that inhibits TGF-β. In some embodiments, the nucleic acid construct encodes a TGF-beta trap. In some embodiments, the TGF-beta trap includes the extracellular domain of a TGFβ RII molecule. In some embodiments, the TGF-beta trap includes a single chain dimer of the extracellular domain of a TGFβ RII molecule, and most preferably includes a single chain dimer of the TGF-beta Receptor II ectodomain. In exemplary embodiments, the TGF-beta trap as contemplated herein may comprise a polynucleotide sequence with at least 80%, 85%, 90%, 91%, 92%, 93%, 94%, 95%, 96%, 97%, 98% or 99% identity to SEQ ID NO:

63 (TGFBRII extracellular domain), or SEQ ID NO: 65 (TGFb trap sequence). The TGF-beta trap contemplated herein may also comprise an amino acid sequence with at least 80%, 85%, 90%, 91%, 92%, 93%, 94%, 95%, 96%, 97%, 98% or 99% identity to SEQ ID NO: 64 (TGFBRII extracellular domain), or SEQ ID NO: 66 (TGFb trap sequence). Other suitable TGF-beta traps include those described in Mol. Canc. Ther. 2012, Vol 11(7), 1477-1487.

In some embodiments, the modified NK-92 cells to be irradiated as described herein are administered with a TGF-β inhibitor to block TGF-β and help remove immunosuppression. In some embodiments, the NK-92 cells described herein are administered with other immunotherapies to help decrease or eliminate a tumor. For example, TGF-β can be inhibited by intratumoral injection of inhibitory peptides in combination with intratumoral injections of poly(I:C) and an α-CD40 antibody. In some embodiments, the TGF-β inhibitor is combined with IL-2.

In additional embodiments, the irradiated recombinant NK-92 cells as described herein include a nucleic acid encoding a cytokine that provides selection for NK-92 cells that express the cytokine, such as IL-2, IL-12, IL-15, IL-18, or IL-21. In exemplary embodiments, the nucleic acid encodes a cytokine such as IL-2 or IL-15. In one embodiment, a cytokine, such as the IL-2 polypeptide may have a sequence with at least 80%, 85%, 90%, 91%, 92%, 93%, 94%, 95%, 96%, 97%, 98% or 99% identity to SEQ ID NO:42. In some embodiments, the IL-2 polypeptide may have a sequence with at least 80%, 85%, 90%, 91%, 92%, 93%, 94%, 95%, 96%, 97%, 98% or 99% identity to SEQ ID NO:43.

In one embodiment, the IL-2 is expressed with a signal sequence that directs the IL-2 to the endoplasmic reticulum IL-2 ("erIL-2"). In another embodiment, the IL-15 is expressed with a signal sequence that directs the IL-15 to the endoplasmic reticulum IL-15 ("erIL-15").

Accordingly, in some embodiments, the cytotoxicity of the irradiated NK-92cells disclosed herein is dependent on the presence of cytokines (e.g., interleukin-2 (IL-2)). Thus, optionally, modified NK-92 cells are further modified to express at least one cytokine. Optionally, the at least one cytokine is IL-2, IL-12, IL-15, IL-18, IL-21 or a variant thereof. Optionally, the at least one cytokine is IL-2, IL-15 or a combination thereof. Optionally, the IL-2 and/or IL-15 is expressed with a signal sequence that directs the cytokine to the endoplasmic reticulum. Directing the IL-2 to the endoplasmic reticulum permits expression of IL-2 at levels sufficient for autocrine activation and without releasing substantial amounts of IL-2 extracellularly. See Konstantinidis et al "Targeting IL-2 to the endoplasmic reticulum confines autocrine growth stimulation to NK-92® cells" Exp Hematol. 2005 February; 33(2):159-64. A representative nucleic acid encoding IL-2 is shown in SEQ ID NO:14 and a representative polypeptide of IL-2 is shown in SEQ ID NO:15.

The irradiated modified NK-92 cells may comprise a nucleic acid sequence encoding IL-2, with 70%, 80%, 90%, or 95% identity to SEQ ID NO:14. Optionally, the irradiated modified NK-92 cells may include a nucleic acid sequence with 90%, 91%, 92%, 93%, 94%, 95%, 96%, 97%, 98% or 99% identity to SEQ ID NO:14. Optionally, the irradiated modified NK-92® cells may include a IL-2 polypeptide with 70%, 80%, 90%, or 95% identity to SEQ ID NO:15. Optionally, the irradiated modified NK-92 cells may include a IL-2 polypeptide with 90%, 91%, 92%, 93%, 94%, 95%, 96%, 97%, 98% or 99% identity to SEQ ID NO:15. The disclosed irradiated modified NK-92 cells advantageously are capable of being maintained in the absence of IL-2 without secreting IL-2 in an amount to cause a clinical adverse effect.

Furthermore, the nucleic acid construct (e.g., the quadricistronic vector) may also include a sequence that encodes a 2A peptide, such as a T2A, P2A, E2A, or F2A peptide, in order to produce equimolar levels of polypeptides encoded by the same mRNA. The E2A peptide contemplated herein may comprise a polynucleotide sequence with at least 80%, 85%, 90%, 91%, 92%, 93%, 94%, 95%, 96%, 97%, 98% or 99% identity to SEQ ID NO: 17. The T2A peptide as contemplated herein may comprise a polynucleotide sequence with at least 80%, 85%, 90%, 91%, 92%, 93%, 94%, 95%, 96%, 97%, 98% or 99% identity to SEQ ID NO: 18.

In one exemplary, non-limiting example, the nucleic acid construct (e.g., the quadcistronic vector) disclosed herein may include a polynucleotide sequence having at least 80%, 85%, 90%, 91%, 92%, 93%, 94%, 95%, 96%, 97%, 98% or 99% identity to SEQ ID NO: 19 (5' Homology arm of AAVS1), SEQ ID NO:20 (EF1a Promoter), SEQ ID NO: 21(T7 Promoter), SEQ ID NO: 22 (CCR7 cDNA), SEQ ID NO: 23 (P2A element), SEQ ID NO: 24 (IgHC leader), SEQ ID NO: 25 (CD19 CAR minus signal peptide), SEQ ID NO: 26 (high affinity CD16), SEQ ID NO: 27 (IRES), SEQ ID NO: 28(SC40 Poly-A), SEQ ID NO: 29 (3' Homology arm of AAVS1), and/or SEQ ID NO: 30 (Homology arm of AAVS1) for targeting the AAVS1 locus (SEQ ID NO: 7).

In some embodiments, the modified NK-92 cells to be irradiated as described herein may include or also include a nucleic acid construct encoding an antigen binding protein ("ABP"). In some embodiments, the antigen binding protein specifically binds a tumor associated antigen. In some embodiments, the ABP includes a fragment of an antibody, such as an scFv. In some embodiments, the antigen binding protein includes or is part of a chimeric antigen receptor (CAR). In some embodiments, the nucleic acid encodes an ABP, a CAR, or an ABP that includes a CAR that specifically binds CD19, CD20, NKG2D ligands, CS1, GD2, CD138, EpCAM, HER-2, EBNA3C, GPA7, CD244, CA-125, MUC-1, ETA, MAGE, CEA, CD52, CD30, MUC5AC, c-Met, EGFR, FAP, WT-1, PSMA, NY-ESO1, CSPG-4, IGF1-R, Flt-3, CD276, CD123, PD-L1, BCMA, CD33, B7-H4, or 41BB.

Additionally or alternatively, the modified NK-92 cells to be irradiated as described herein encode for an antigen binding protein that binds an immune modulator protein in a tumor. Examples of immune modulator proteins found in tumors, include CTLA-4, PD-1, IDO-1, CD39, and CD73.

In exemplary embodiments, the modified NK-92 cells to be irradiated as described herein are transfected with a nucleic acid construct encoding one or more CAR molecules that specifically binds the programmed cell death ligand 1 (PD-L1) (e.g., an anti-PD-L1 CAR). For example, the nucleic acid construct encoding one or more CAR molecules that specifically binds PD-L1 has an amino acid sequence comprising at least 90%, 91%, 92%, 93%, 94%, 95%, 96%, 97%, 98% or 99% identical to SEQ ID NO:69 (which may be encoded by a nucleic acid sequence at least 90%, 91%, 92%, 93%, 94%, 95%, 96%, 97%, 98% or 99% identical to SEQ ID NO:68.

In specific embodiments, NK-92 cells are transfected with an expression vector (e.g., the quadricistronic vector) comprising: SEQ ID NO:1 or a nucleic acid with 90%, 91%, 92%, 93%, 94%, 95%, 96%, 97%, 98% or 99% identity to SEQ ID NO:1; SEQ IDNO: 25 (CD19 CAR) or a nucleic acid with 90%, 91%, 92%, 93%, 94%, 95%, 96%, 97%, 98% or 99% identity to SEQ ID NO:13 (CD16 F158V), or a nucleic acid or polypeptide sequence with 90%, 91%, 92%, 93%, 94%, 95%, 96%, 97%, 98% or 99% identity to SEQ ID NO:14 (erIL-2 n.t. sequence); and/or SEQ ID NO:15 (erIL-2 a.a. sequence), or a nucleic acid with 90%, 91%, 92%, 93%, 94%, 95%, 96%, 97%, 98% or 99% identity to SEQ ID NO:14.

In other specific embodiments, NK-92 cells are transfected with an expression vector (e.g., the quadricistronic vector) comprising: SEQ ID NO:47 (CXCR2) or a nucleic acid with 90%, 91%, 92%, 93%, 94%, 95%, 96%, 97%, 98% or 99% identity to SEQ ID NO:47; SEQ ID NO:25 (CD19 CAR) or a nucleic acid with 90%, 91%, 92%, 93%, 94%, 95%, 96%, 97%, 98% or 99% identity to SEQ ID NO:12; and SEQ ID NO:13 (CD16 158V), and/or a nucleic acid with 90%, 91%, 92%, 93%, 94%, 95%, 96%, 97%, 98% or 99% identity to SEQ ID NO:14; and/or SEQ ID NO:15 (erIL-2), or a nucleic acid with 90%, 91%, 92%, 93%, 94%, 95%, 96%, 97%, 98% or 99% identity to SEQ ID NO:14. Suitable expression vectors are known in the art and can be used. In further aspects, the recombinant nucleic acid comprises a segment encoding erIL-15, and the nucleic acid encoding erIL-15 has at least 90%, 91%, 92%, 93%, 94%, 95%, 96%, 97%, 98% or 99% identity to SEQ ID NO:67. Optionally, the expression vector is a plasmid.

In an optional embodiment, the CAR may comprise a CD19CAR_CD3a having a polynucleotide sequence having at least 80%, 85%, 90%, 91%, 92%, 93%, 94%, 95%, 96%, 97%, 98% or 99% identity to SEQ ID NO: 41.

Considered form a different perspective, the irradiated recombinant NK-92 cells having maintained activity can be administered to cancer patients for decreasing cancer cells or tumor size. Accordingly, methods for treating a cancer or a tumor in a subject include administering to the subject a therapeutically effective amount of an irradiated recombinant NK-92 cell. First the wherein the recombinant NK-92 cell is transfected with a nucleic acid as disclosed herein encoding i) a homing receptor; ii) an antigen binding protein (ABP) or a chimeric antigen receptor (CAR) that specifically binds a target antigen; iii) an Fc Receptor; and/or iv) a secreted immune modulator selected from a TGFβ inhibitor and/or IL-12, wherein the nucleic acid is operably linked to a promoter. The transfected recombinant NK-92 cell is subsequently irradiated with 2.5, 5, 10, or 15 Gray. The irradiated recombinant KN-92 cells are subsequently administered to the subject (e.g., cancer patient). In some embodiments, about $1\times10^3$ to $1\times10^{10}$, per $m^2$ of the irradiated recombinant NK-92 cells are administered to the subject. Administration of the irradiated recombinant NK-92 cells as disclosed herein, may be parenterally, intravenously, peritumorally, or infused into the subject.

According to the methods provided herein, the subject is administered an effective amount of the irradiated recombinant NK cells as disclosed herein. The terms effective amount and effective dosage are used interchangeably. The term effective amount is defined as any amount necessary to produce a desired physiologic response (e.g., reduction of inflammation). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 22nd Edition, Gennaro, Editor (2012), and Pickar, Dosage Calculations (1999)).

Pharmaceutically acceptable compositions can include a variety of carriers and excipients. A variety of aqueous carriers can be used, e.g., buffered saline and the like. These solutions are sterile and generally free of undesirable matter. Suitable carriers and their formulations are described in *Remington: The Science and Practice of Pharmacy, 22nd Edition*, Loyd V. Allen et al., editors, Pharmaceutical Press (2012). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. As used herein, the term pharmaceutically acceptable is used synonymously with physiologically acceptable and pharmacologically acceptable. A pharmaceutical composition will generally comprise agents for buffering and preservation in storage and can include buffers and carriers for appropriate delivery, depending on the route of administration.

The compositions may contain acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of cells in these formulations and/or other agents can vary and will be selected primarily based on fluid volumes, viscosities, body weight and the like in accordance with the particular mode of administration selected and the subject's needs.

Kits

Provided herein are kits comprising the recombinant NK-92 cells described herein. In some embodiments, the kit comprises recombinant NK-92 cells comprising one or more nucleic acid sequences encoding i) a homing receptor, ii) an ABP or CAR that specifically binds to a target antigen, iii) an Fc Receptor and/or iv) a secreted immune modulator selected from a TGFβ inhibitor and/or IL-12. Optionally, one or more proteins encoded by the nucleic acid sequences are expressed on the cell surface of the recombinant NK-92 cells cells. In some embodiments, kit comprises a recombinant NK-92 cell comprising a nucleic acid encoding C—C chemokine receptor type 7 (CCR7), CXCR2, or the receptor for CXCL14 operably linked to a promoter. Optionally, the nucleic acid encoding CCR7 has at least 90%, 91%, 92%, 93%, 94%, 95%, 96%, 97%, 98% or 99% identity to SEQ ID NO:1. Optionally, the homing receptor is expressed on the cell surface of the recombinant NK-92 cells. Optionally, the promoter comprises one or more NFAT binding elements and a minimal promoter. Optionally, the promoter has at least 90%, 91%, 92%, 93%, 94%, 95%, 96%, 97%, 98% or 99% identity to SEQ ID NO:6. Optionally, one or more proteins encoded by the nucleic acid sequences are expressed on the cell surface of the recombinant NK-92 cells.

Optionally, the recombinant NK-92 cells are provided in a composition comprising a pharmaceutically acceptable excipient. Optionally, a kit may contain additional compounds such as therapeutically active compounds or drugs that are to be administered before, at the same time or after administration of the recombinant NK-92 cells. Optionally, instructions for use of the kits will include directions to use the kit components in the treatment of a cancer. The instructions may further contain information regarding how to prepare (e.g., dilute or reconstitute, in the case of freeze-dried protein) the antibody and the recombinant NK-92 cells (e.g., thawing and/or culturing). The instructions may further include guidance regarding the dosage and frequency of administration.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

EXAMPLES

Figure 3:
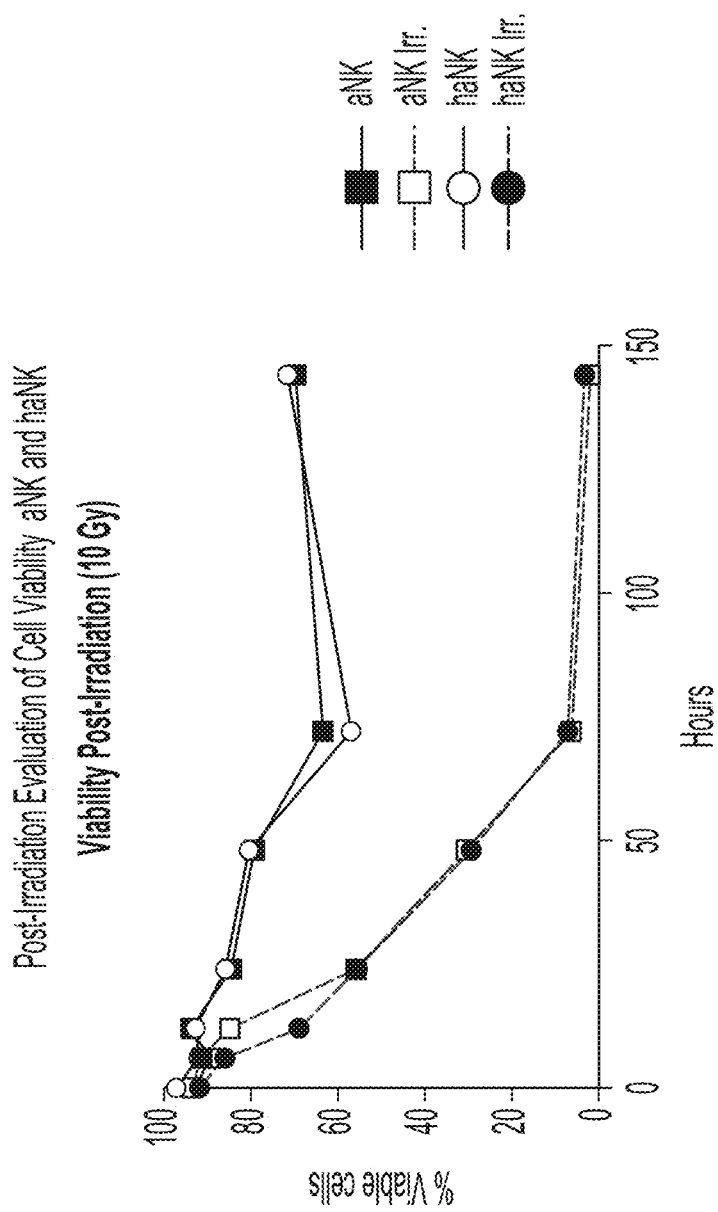
FIG. 3 is a graph showing the percentage of viable cells at the indicated time points (hours) up to approximately 144 hours (6 days) after irradiation with 10 Gy in aNK and haNK cells with non-irradiated aNK and haNK cells as a control.

With reference to FIGS. 2A-2B, wild type NK-92 cells were irradiated with radiation doses ranging from 0 to 30 Gy and the cell concentration and percent viability were measured accordingly over 5 days (120 hours). Cell concentration and percent viability in irradiated (10 Gy) and non-irradiated aNK and haNK cells are shown in FIG. 3.

The PD-L1 t-haNK cell line has been developed for administration to cancer patients with tumors that express the PD-L1 antigen and may also be used in combination regimens with antibodies that recognize tumor-specific antigens. A PD-L1 t-haNK cell line secreting a TGFβ antagonist (TGFbeta-trap/PD-L1 t-haNK) by transfection with a quadricistronic vector is schematically depicted in FIG. 4A was developed for blocking TGFbeta activity in the tumor. However, allogeneic cells can induce harmful effects when infused in cancer patients. Accordingly, to avoid these deleterious effects the TGFbeta-trap/PD-L1 t-haNK cells were irradiated prior to infusion. Considering a higher irradiation dose may also negatively influence the cell function and in particular the secretion of the TGFβ, an optimal irradiation dose is highly desired for inhibiting proliferative capacity without affecting cell function. Accordingly, the cell concentration of TGFbeta-trap/PD-L1 t-haNK cells after irradiation is shown in FIG. 4B, while secretion of the TGFbeta-trap molecule (assaying of TGFbeta-RII ectodomain) after irradiation is shown in FIG. 4C.

Figure 4D:
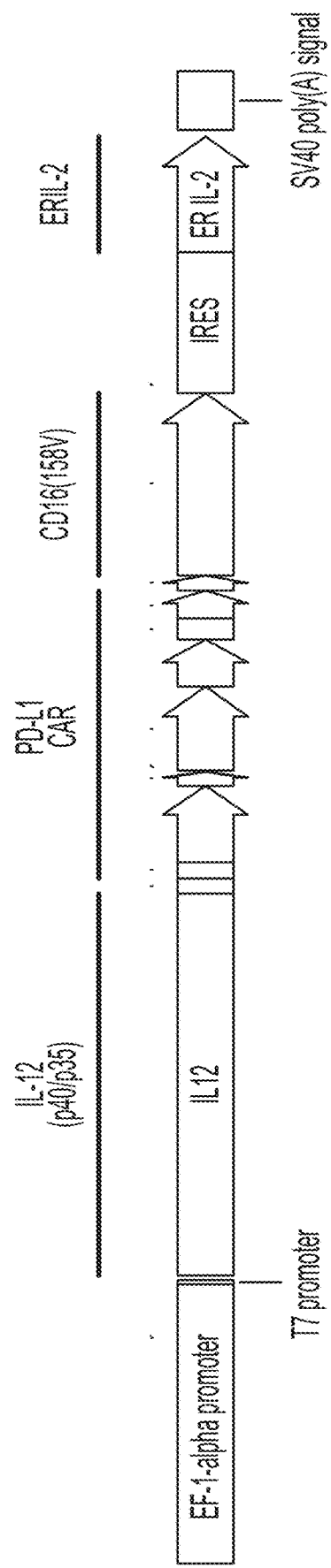
FIG. 4D illustrates one embodiment of a quadricistronic vector encoding an IL-12 armored PD-L1 CAR nucleic acids.

In another embodiment, a quadricistronic vector for expressing IL-12 in a PD-L1 t-haNK cell line (IL-12/PD-L1 t-haNK) is schematically depicted in FIG. 4D. In some embodiments, administration of irradiated PD-L1 t-haNK cells into a subject confer inhibition of IL-12 activity in cancer cells and/or tumor cells in the subject.

Figure 5A:
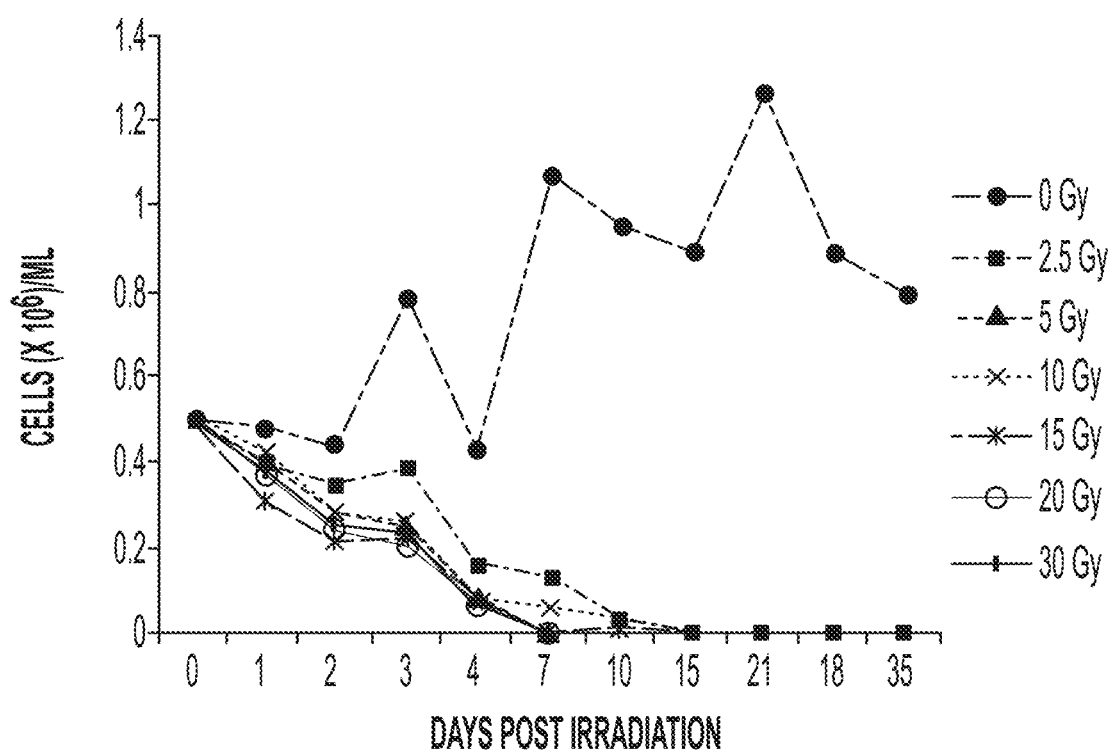
FIG. 5A is a graph showing the number of PD-L1 t-haNK cells per volume (cells×$10^6$/milliliter (mL)) at Day 1, 2, 3, 4, 7, 10, 15, 21, 28, and 35 after 0, 2.5, 5, 10, 15, 20, and 30 Gy irradiation as indicated.

With reference to FIGS. 5A-5B, PD-L1 t-haNK cells were subjected to increasing doses of X-ray irradiation using an RS-2000 Irradiator. After irradiation, cells were set for long-term culture under optimal growth conditions using complete growth media. Viable cells were assessed regularly using a variety of methods including cell density (FIGS. 5A and 5B), cell health assays (FIGS. 7A and 7B) and imaging cytometry methods (FIGS. 6, 7A, 7B) for a period of 35 days.

Study Design

PD-LI t-haNK Cells were formulated in 5% Albumin (Human) at $4.0 \times 10^7$ cells/mL and irradiated using a RS-2000 irradiator at levels of 0, 2.5, 5, 10, 15, 20 and 30 Gy. Immediately following irradiation, cells were diluted in complete growth media (cGM) and placed in an incubator maintained at 37° C. with 5% $CO_2$ atmosphere. Non-irradiated (0 Gy) cells were used as a control. Analytical testing was performed on alternate days during the first week of study followed by weekly testing throughout the remainder of the study. Cell cultures were replenished with fresh media (two-thirds volume) every week.

Pd-L1 t-Hank Cell Concentration and Irradiation

PD-L1 t-haNK cells were concentrated by centrifugation at 336×g for 5 minutes. Cell pellet was suspended in 5% Albumin (human) USP and the concentration was adjusted to $4.0 \times 10^7$ cells/mL. The concentrated cells in different T-25 flasks were irradiated at room temperature with different doses of X-ray irradiation using the RadSource RS-2000. The machine was programmed to irradiate the cells at specified doses and the irradiation time was automatically set by the machine (Table 1).

TABLE 1

IRRADIATION TIME VS DOSE

| SHELF | IRRADIATION DOSE (GY) | TIME TAKEN TO IRRADIATE |
|---|---|---|
| 3 | 0 | 0 |
|  | 2.5 | 1 MIN 39 SEC |
|  | 5 | 3 MIN 17 SEC |
|  | 10 | 3 MIN 31 SEC |
|  | 15 | 5 MIN 17 SEC |
|  | 20 | 7 MIN 22 SEC |
|  | 30 | 10 MIN 33 SEC |

Analytical Testing

Figure 6:
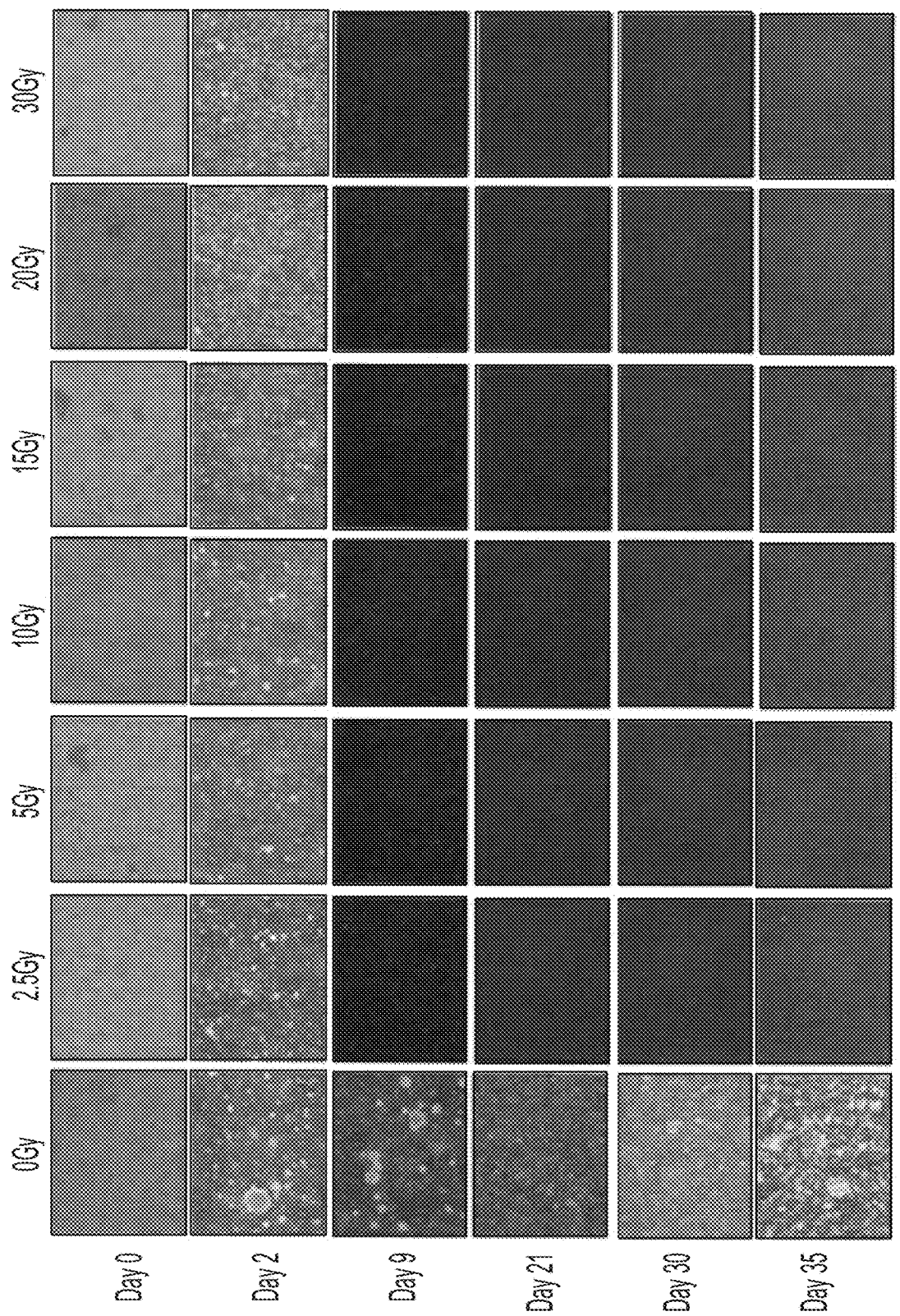
FIG. 6 shows brightfield images captured using an EVOS microscope to visualize cell morphology of the PD-L1 t-haNK cells at Day 0, 2, 9, 21, 30, and 35 after 0, 2.5, 5, 10, 15, 20, or 30 Gy radiation, as indicated.
Figure 6:
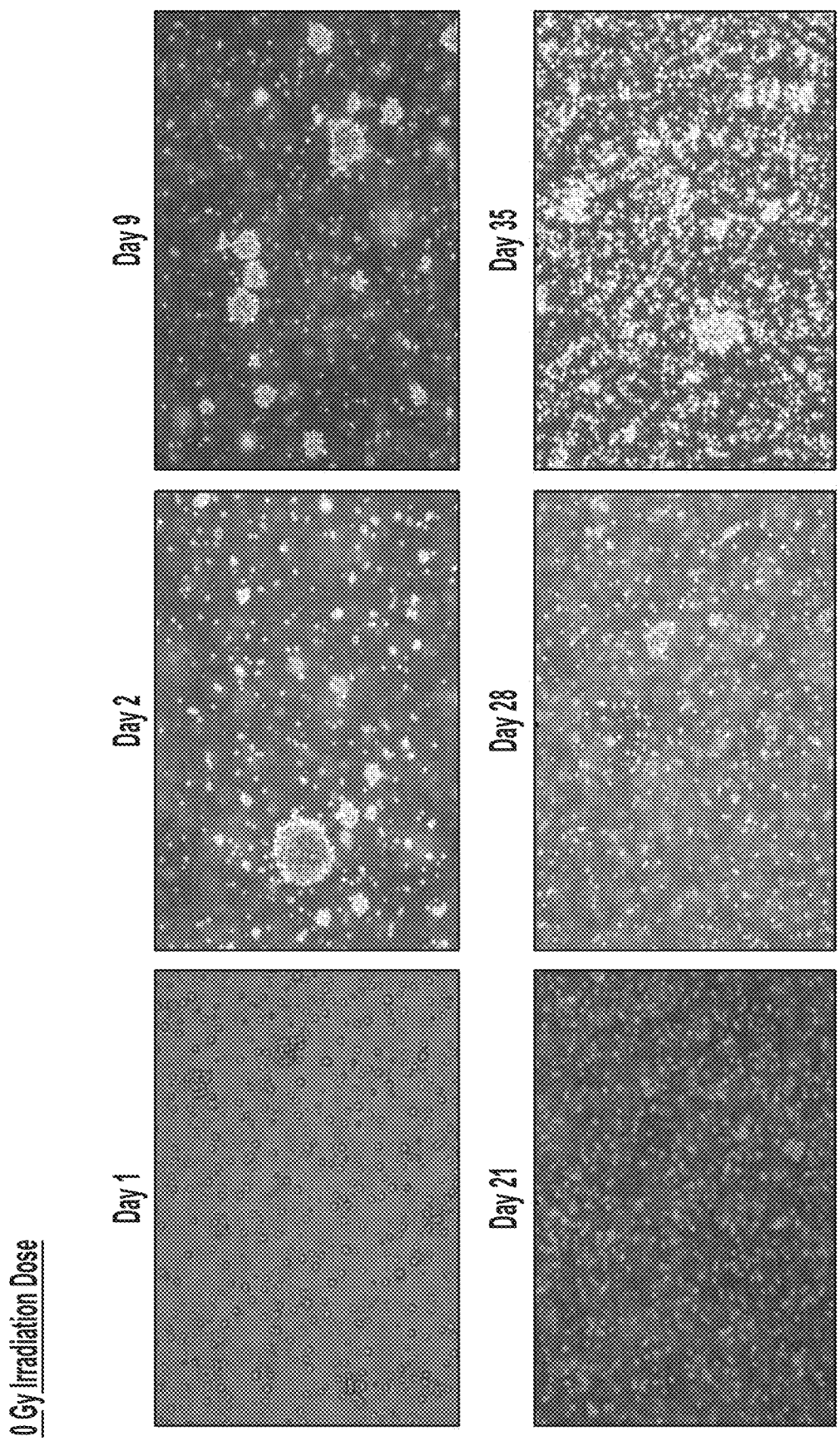
Figure 6:
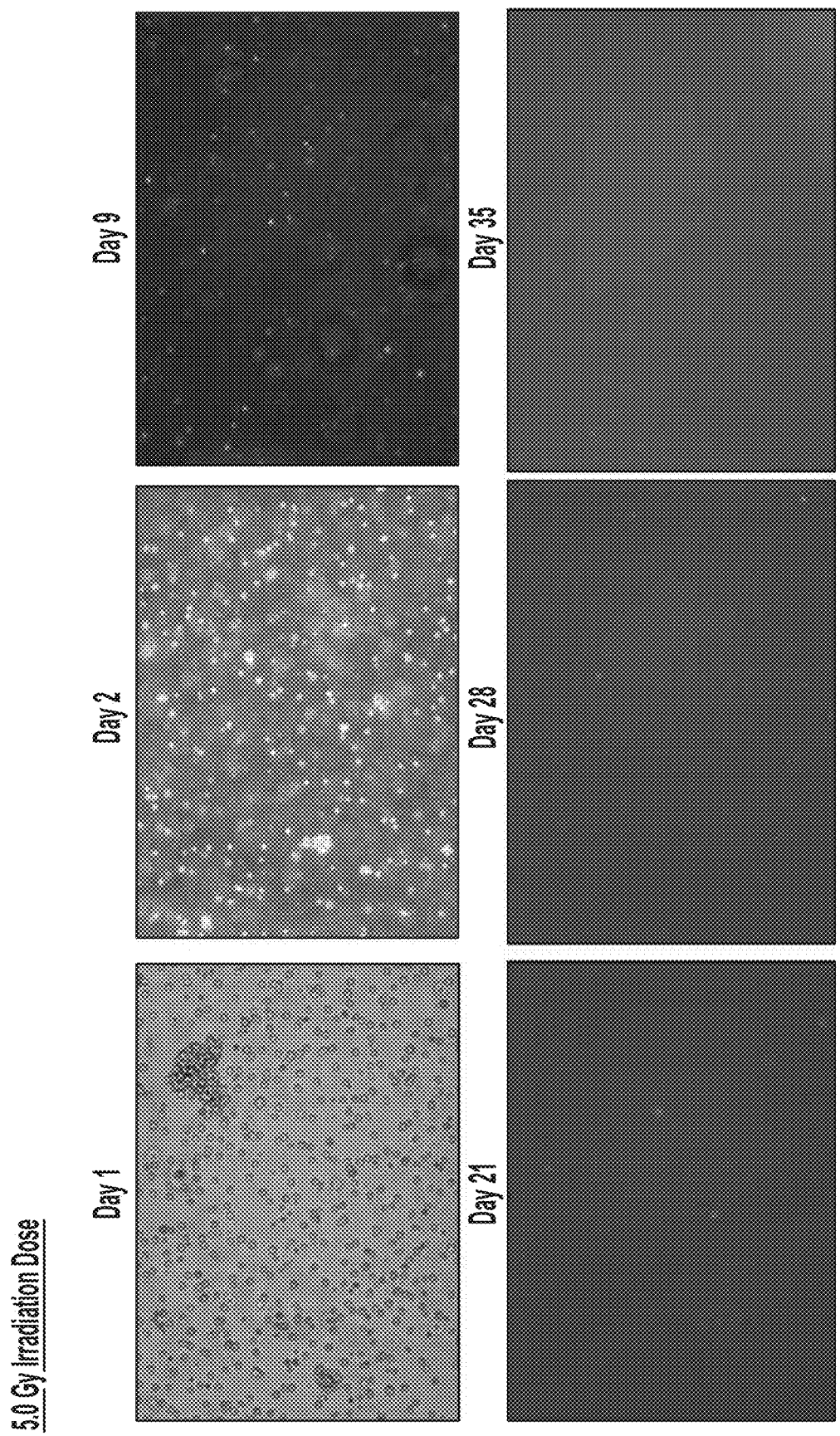
Figure 6:
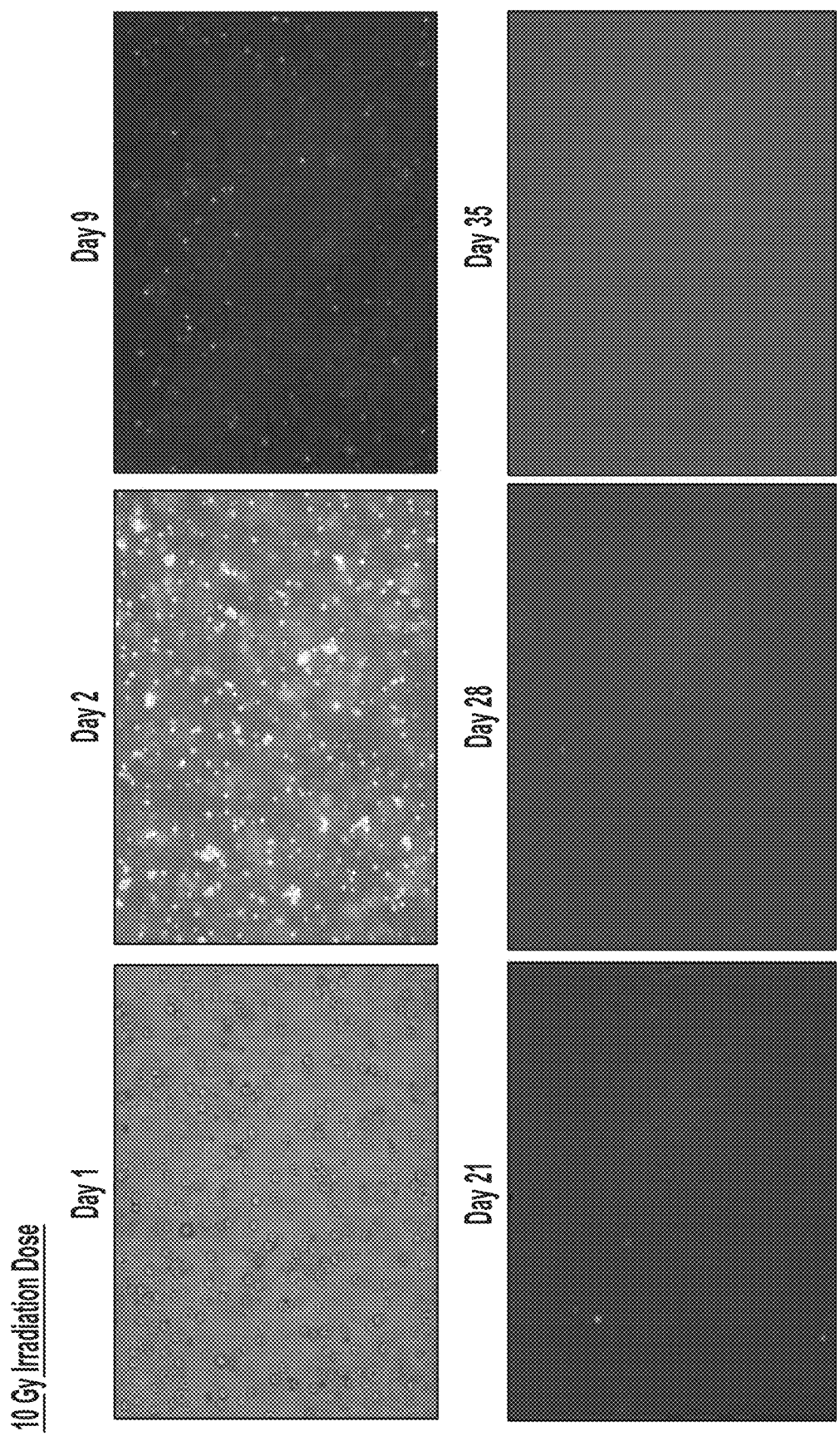
Figure 6:
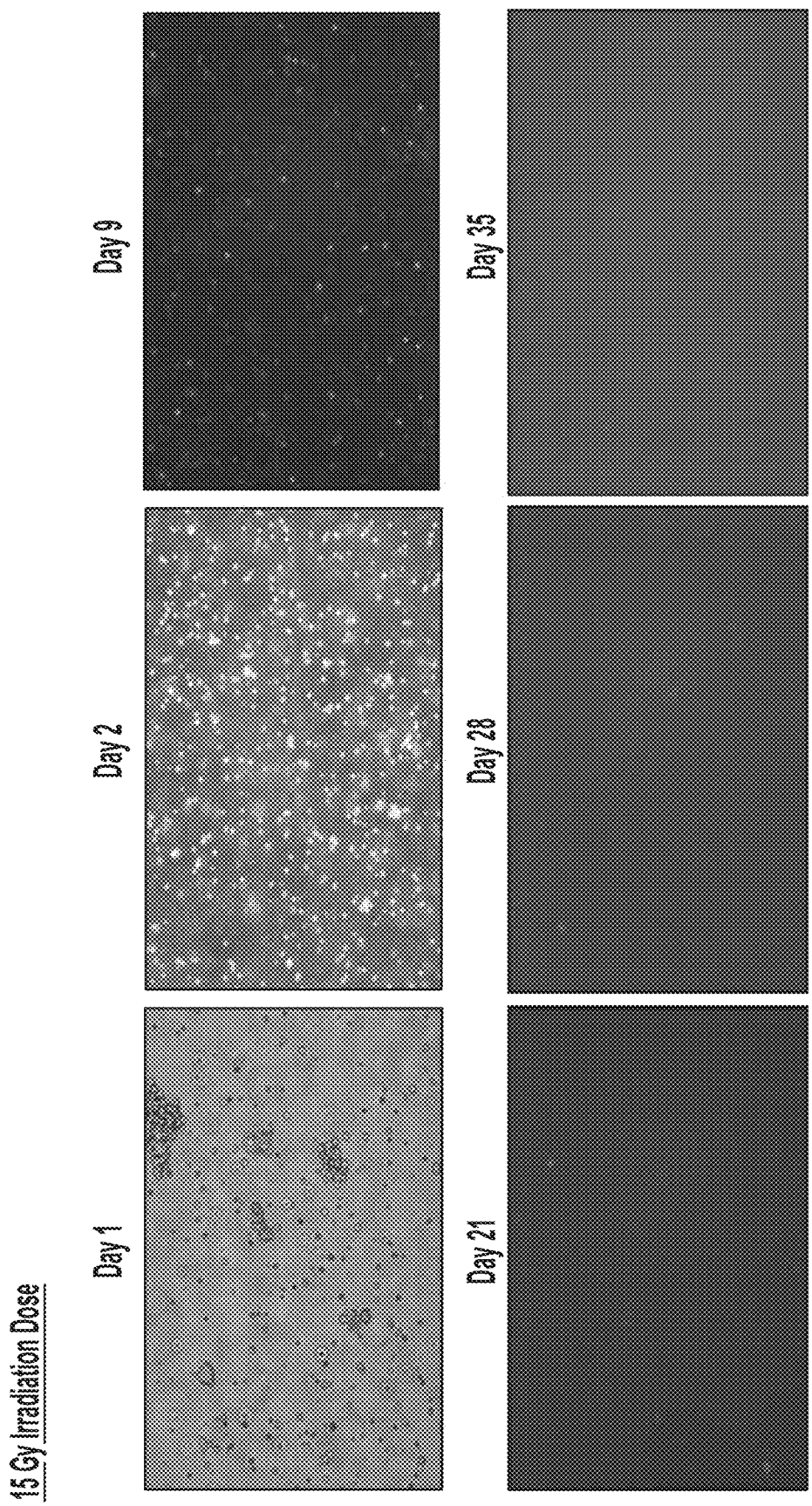
Figure 6:
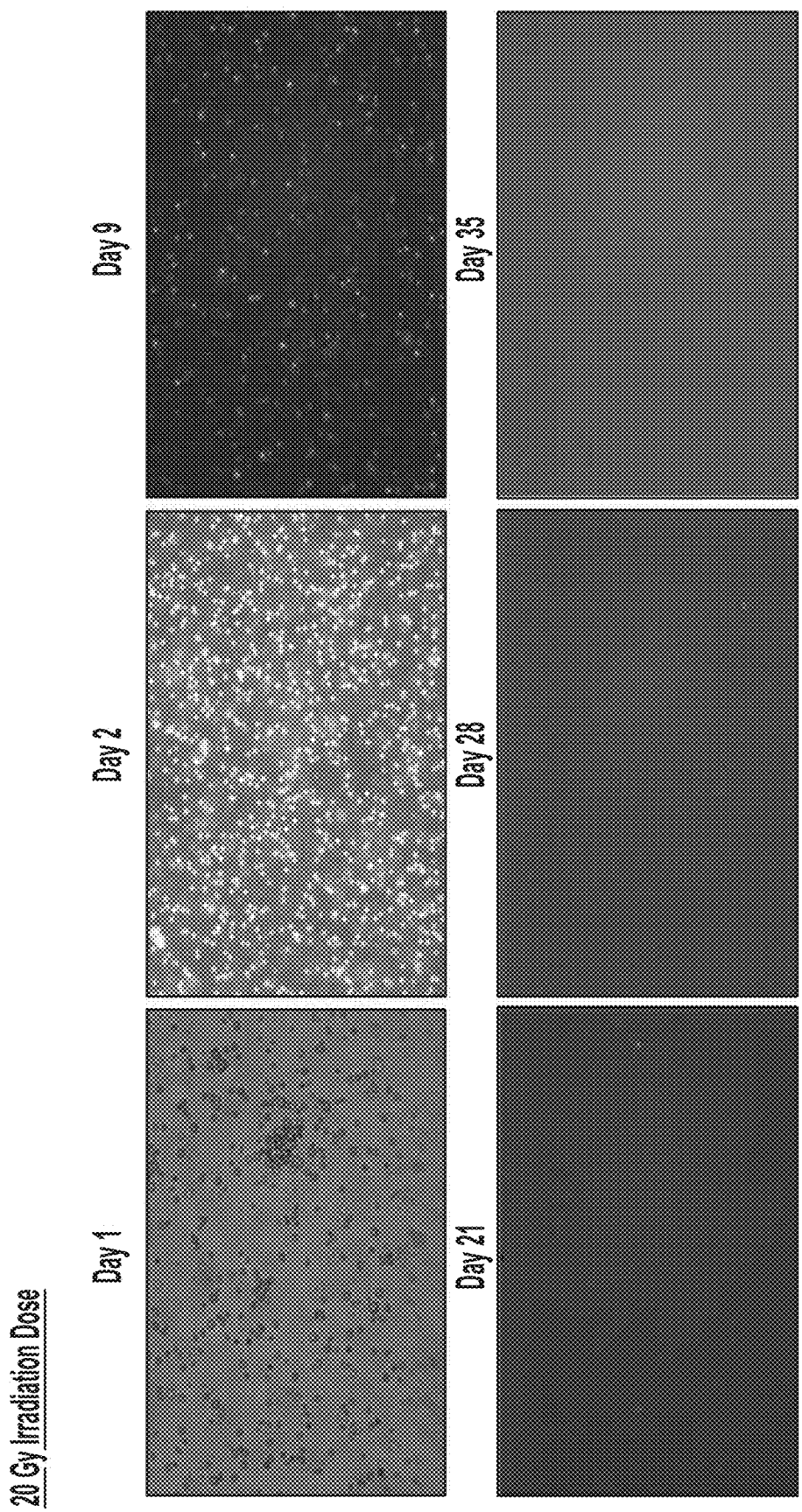
Figure 6:
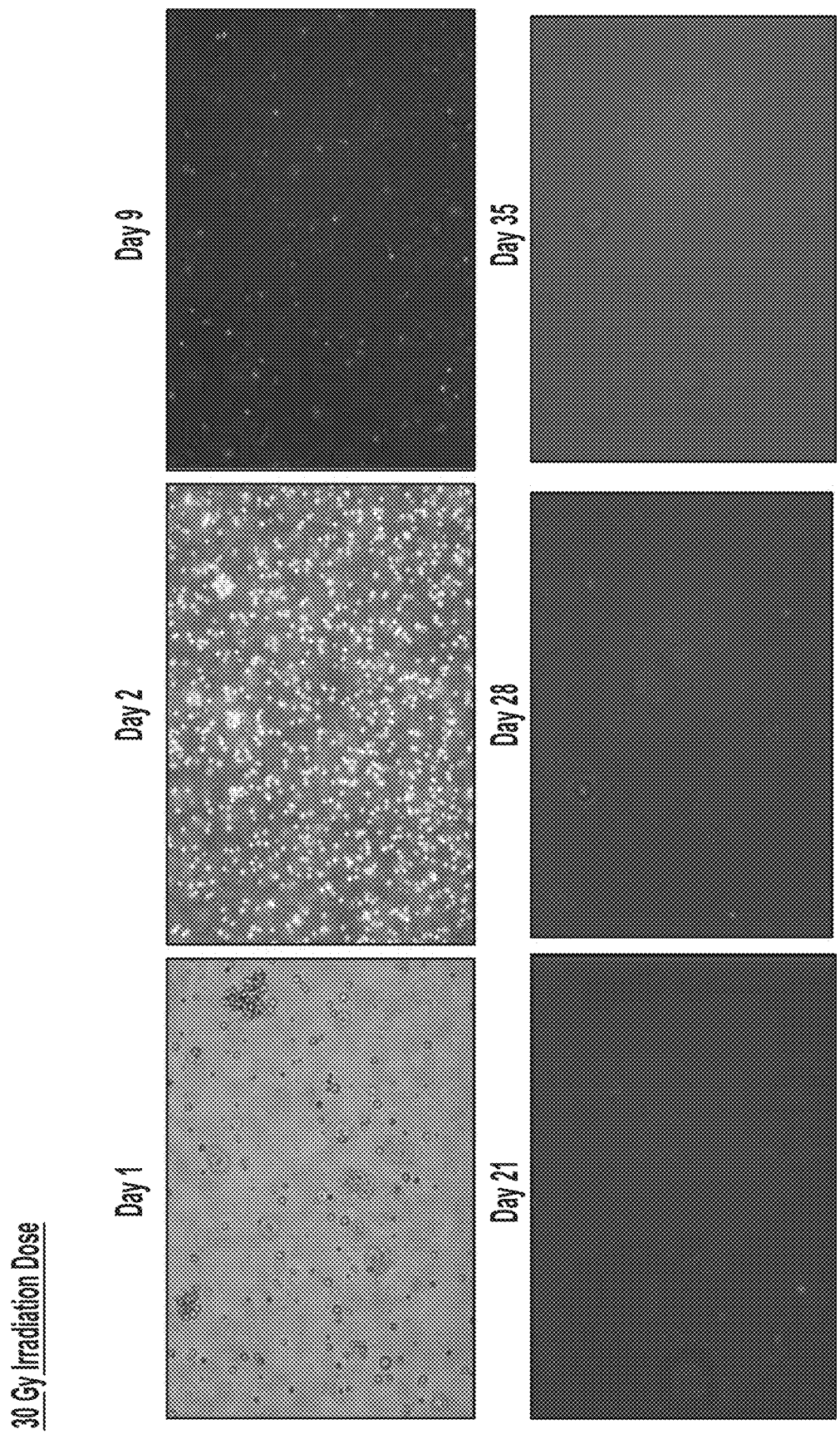
Figure 7A:
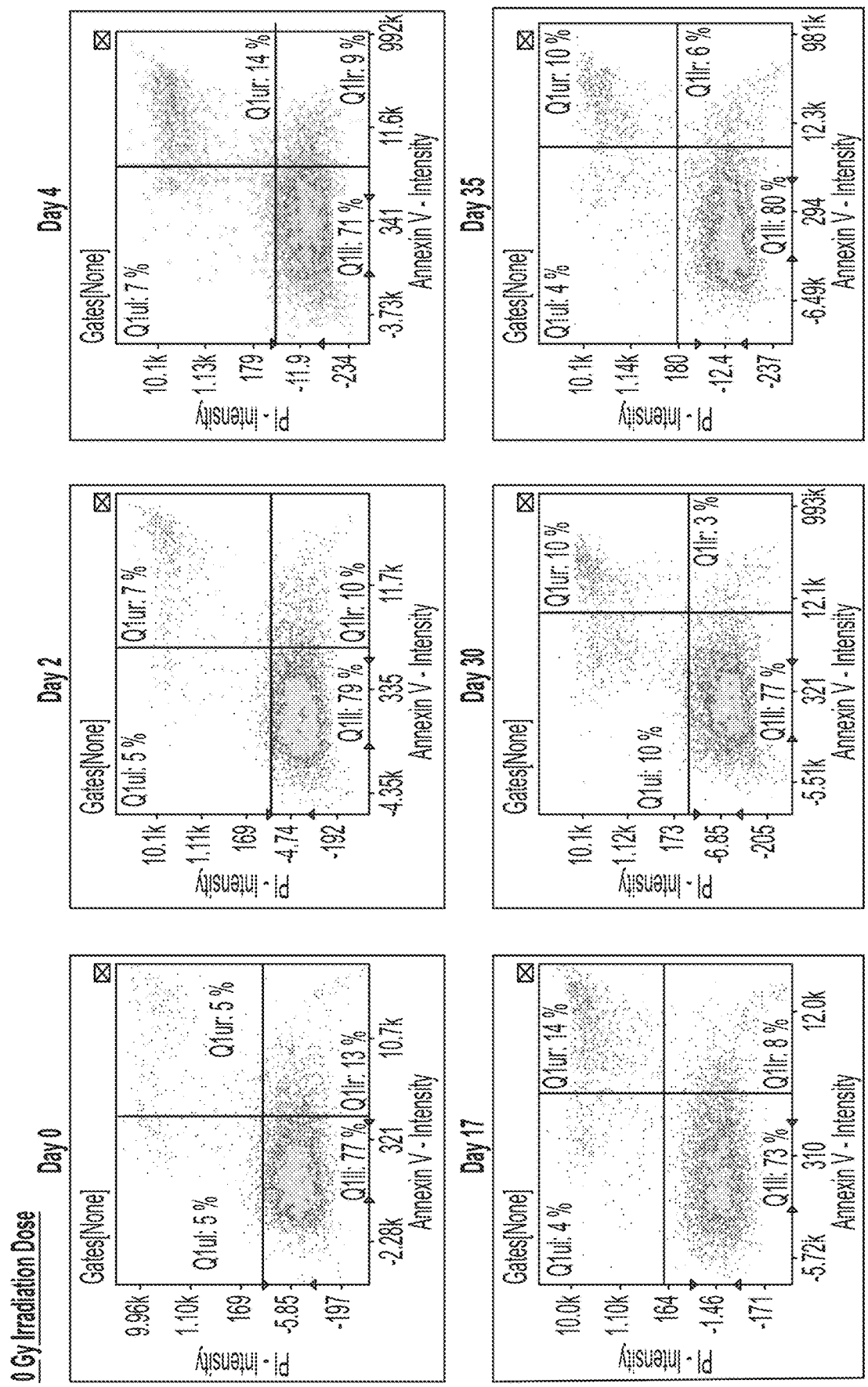
FIG. 7A shows cytometry images from an Annexin Assay of Annexin V stained PD-L1 t-haNK cells at Day 0, 2, 4, 17, 30, and 35 after 0, 2.5, 5, 10, 15, 20, or 30 Gy radiation, as indicated.
Figure 7A:
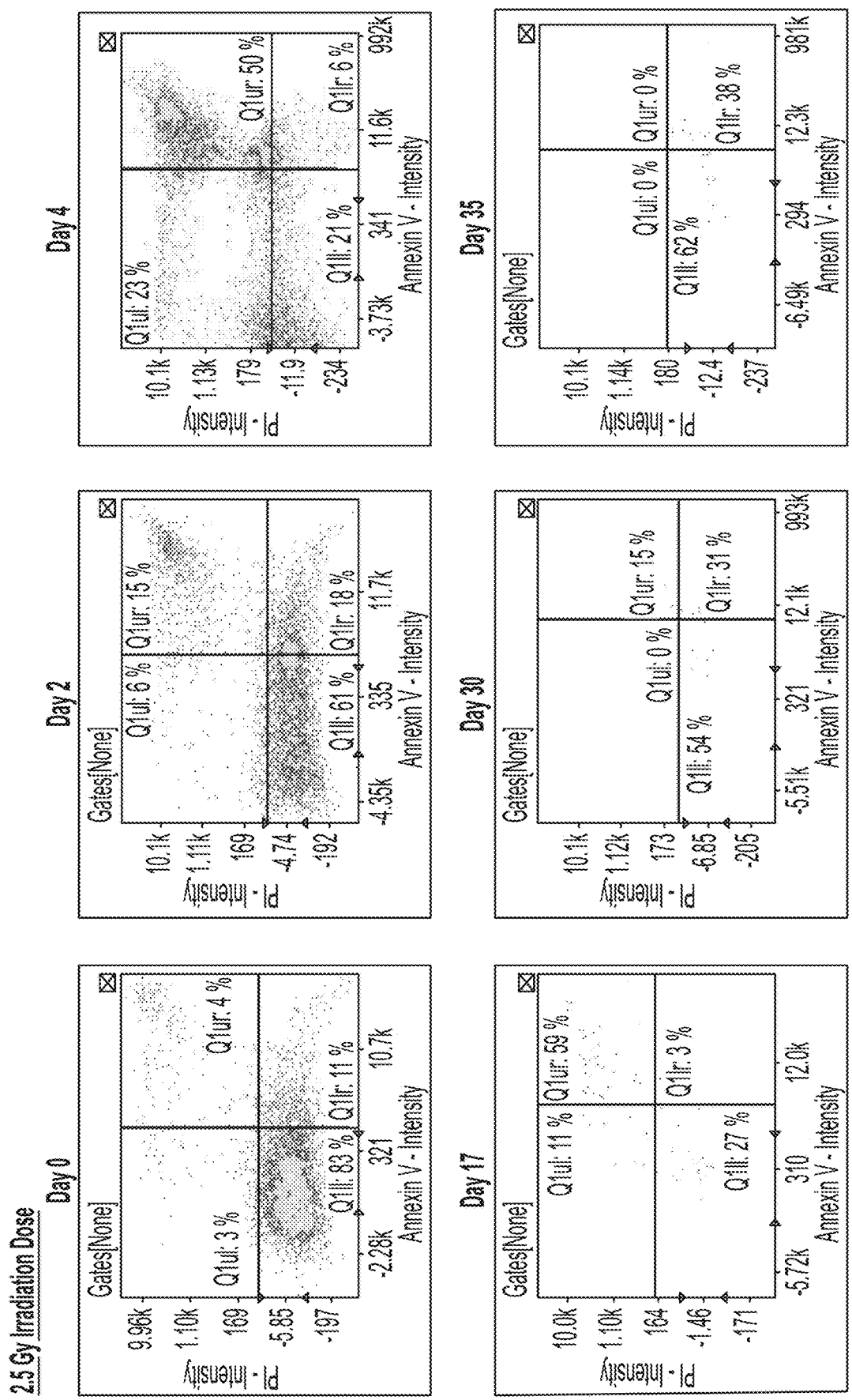
Figure 7A:
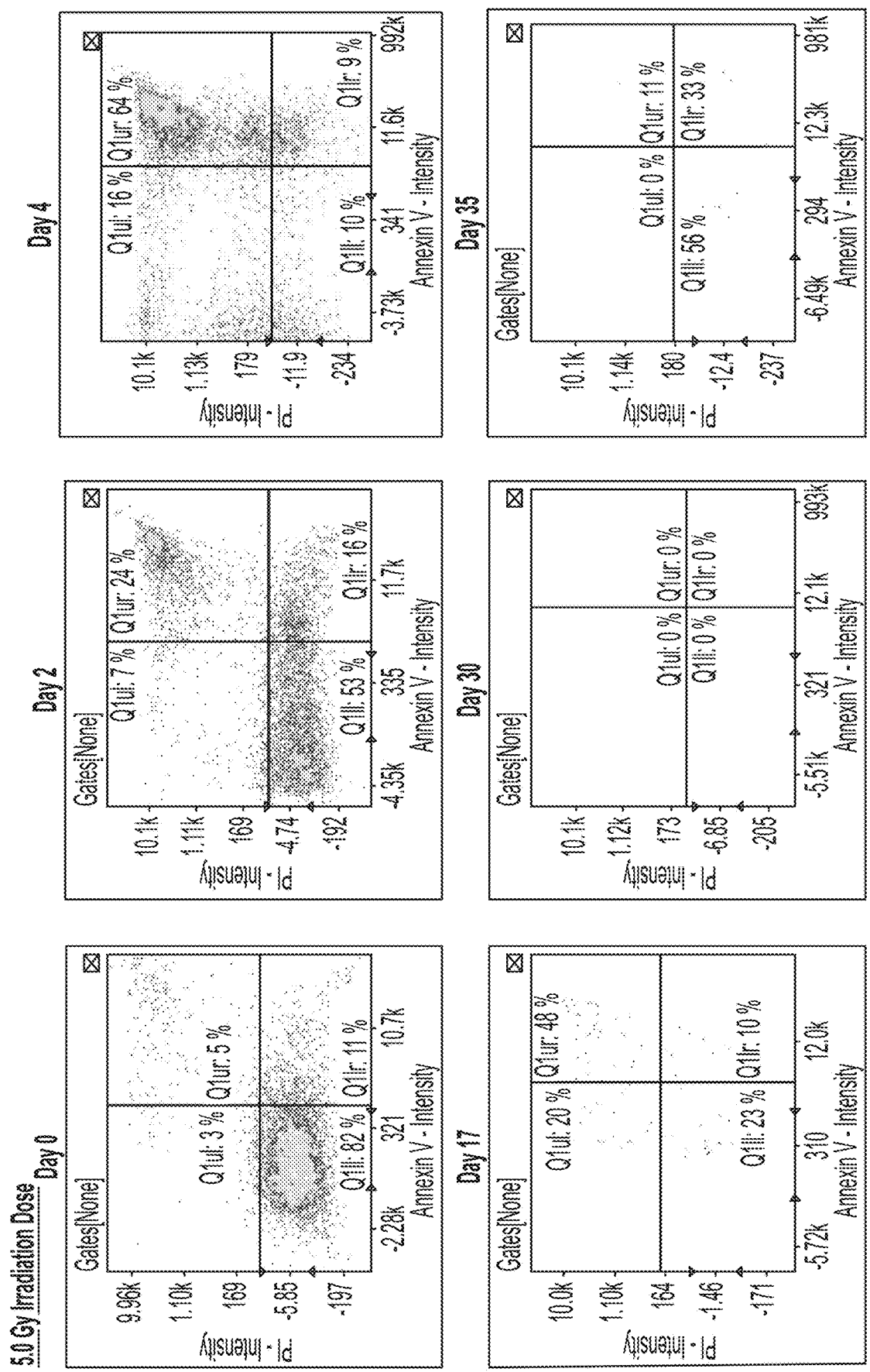
Figure 7A:
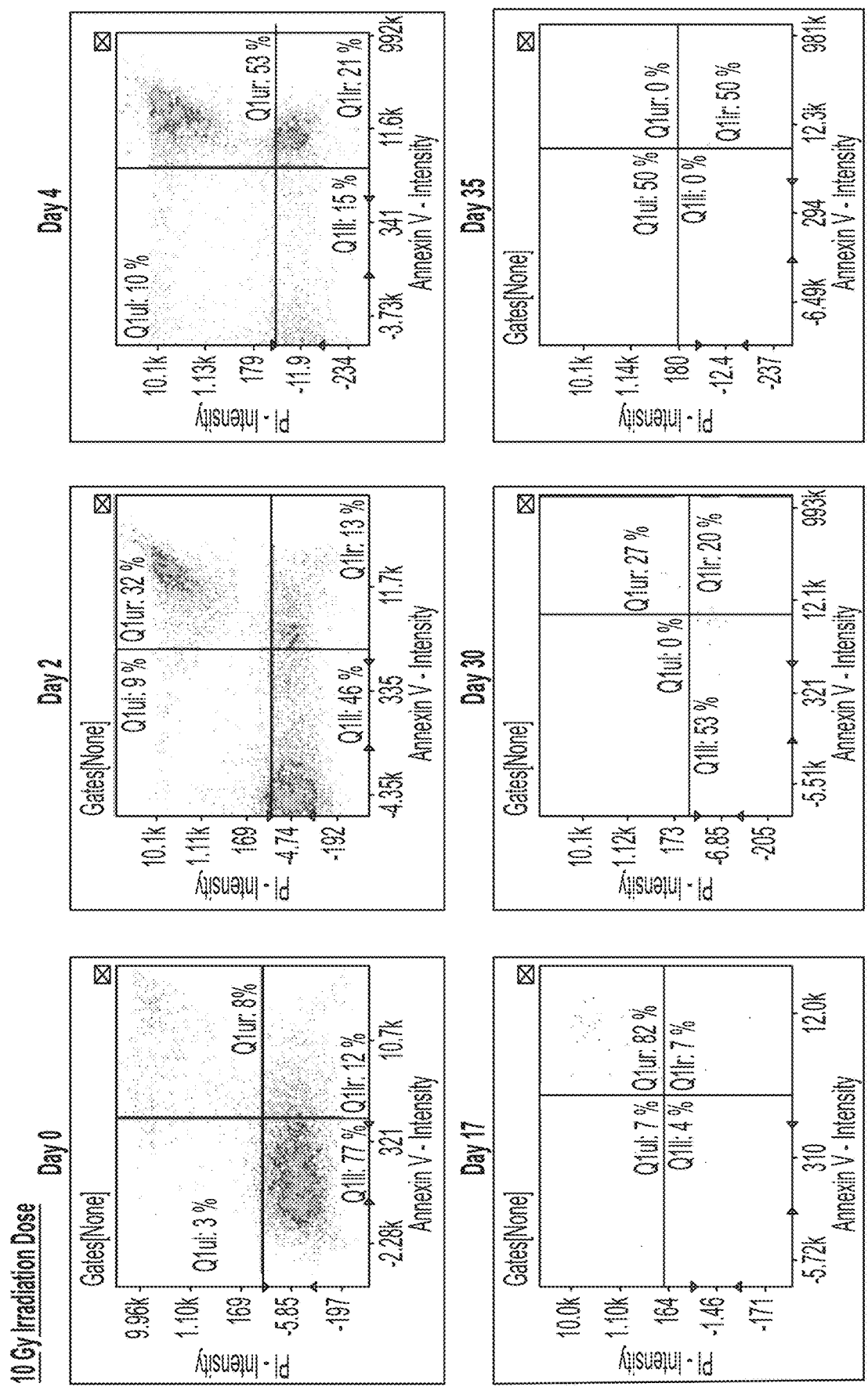
Figure 7A:
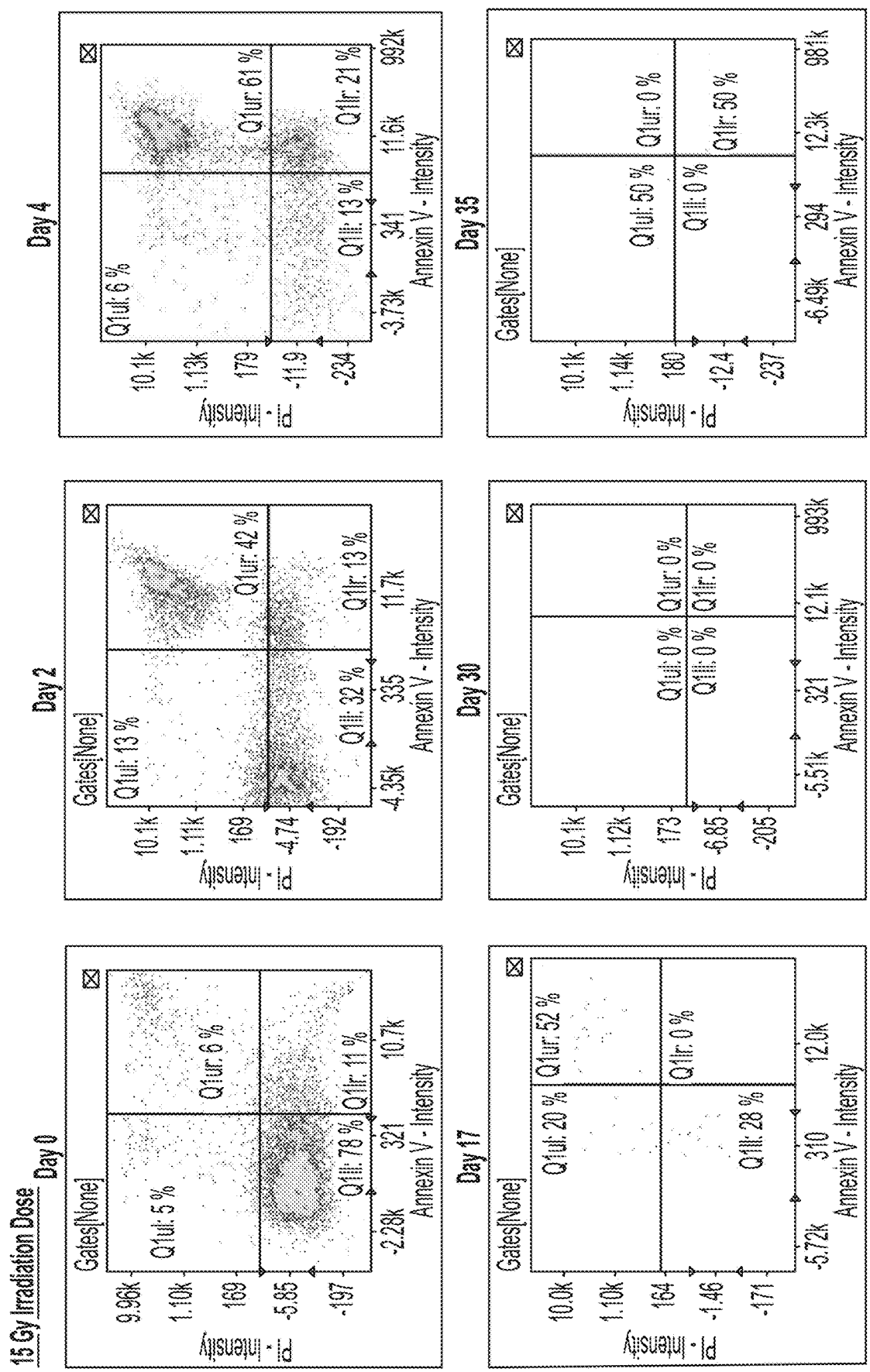
Figure 7A:
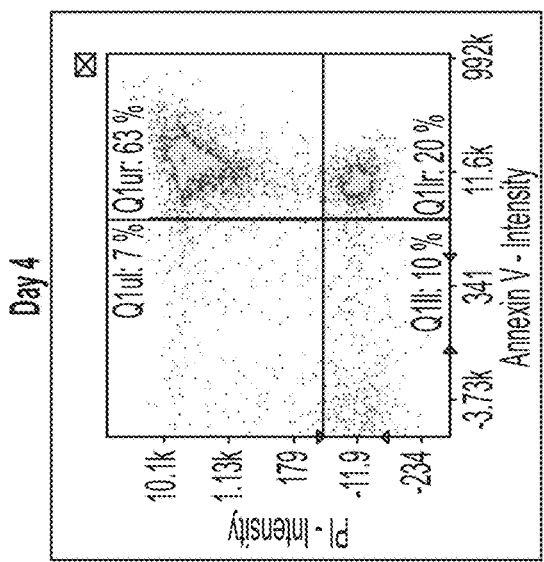
Figure 7A:
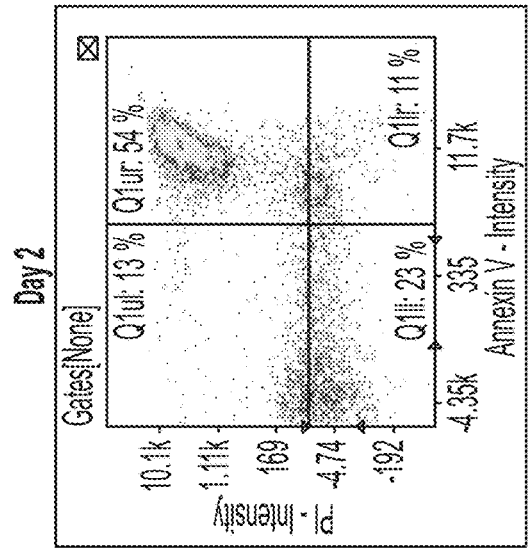
Figure 7A:
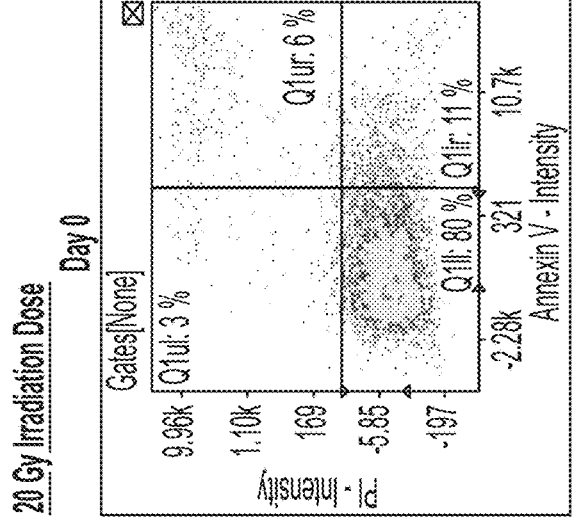
Figure 7A:
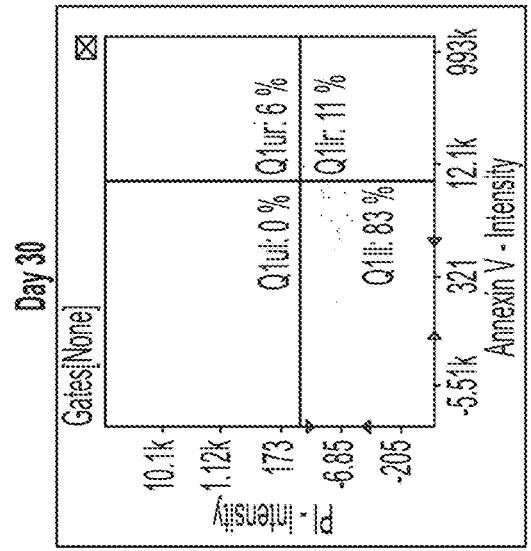
Figure 7A:
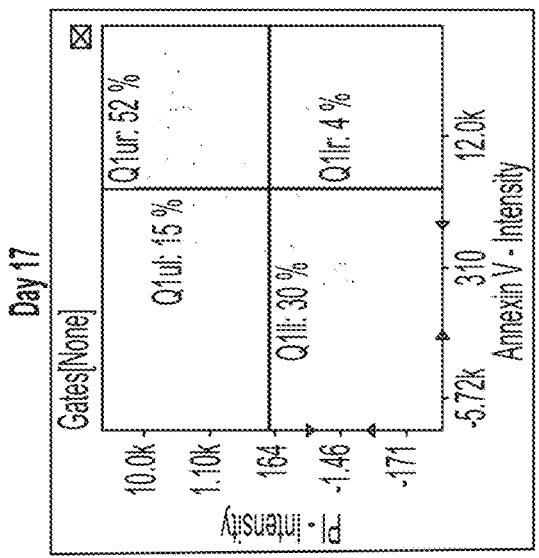
Figure 7A:
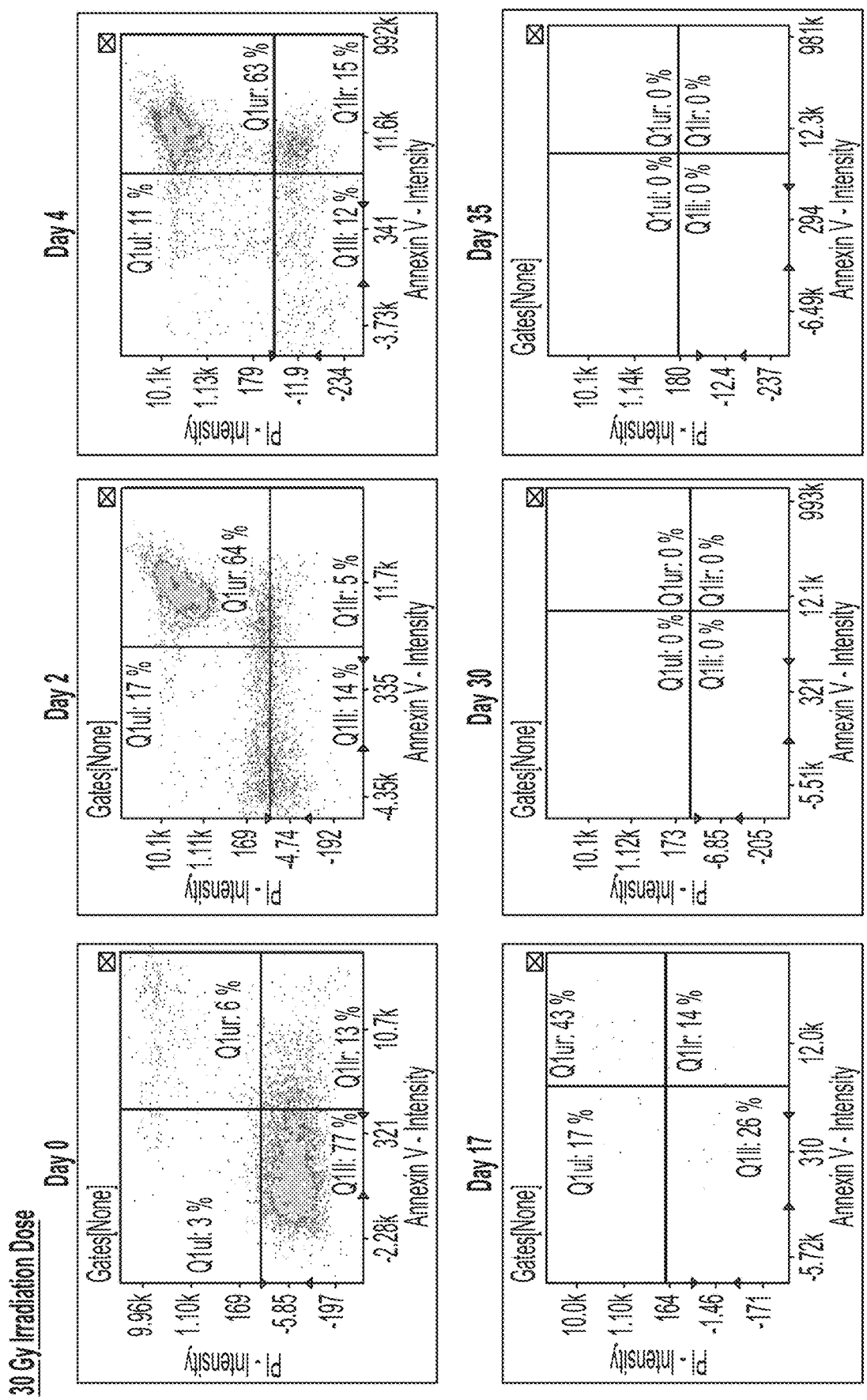
Figure 7B:
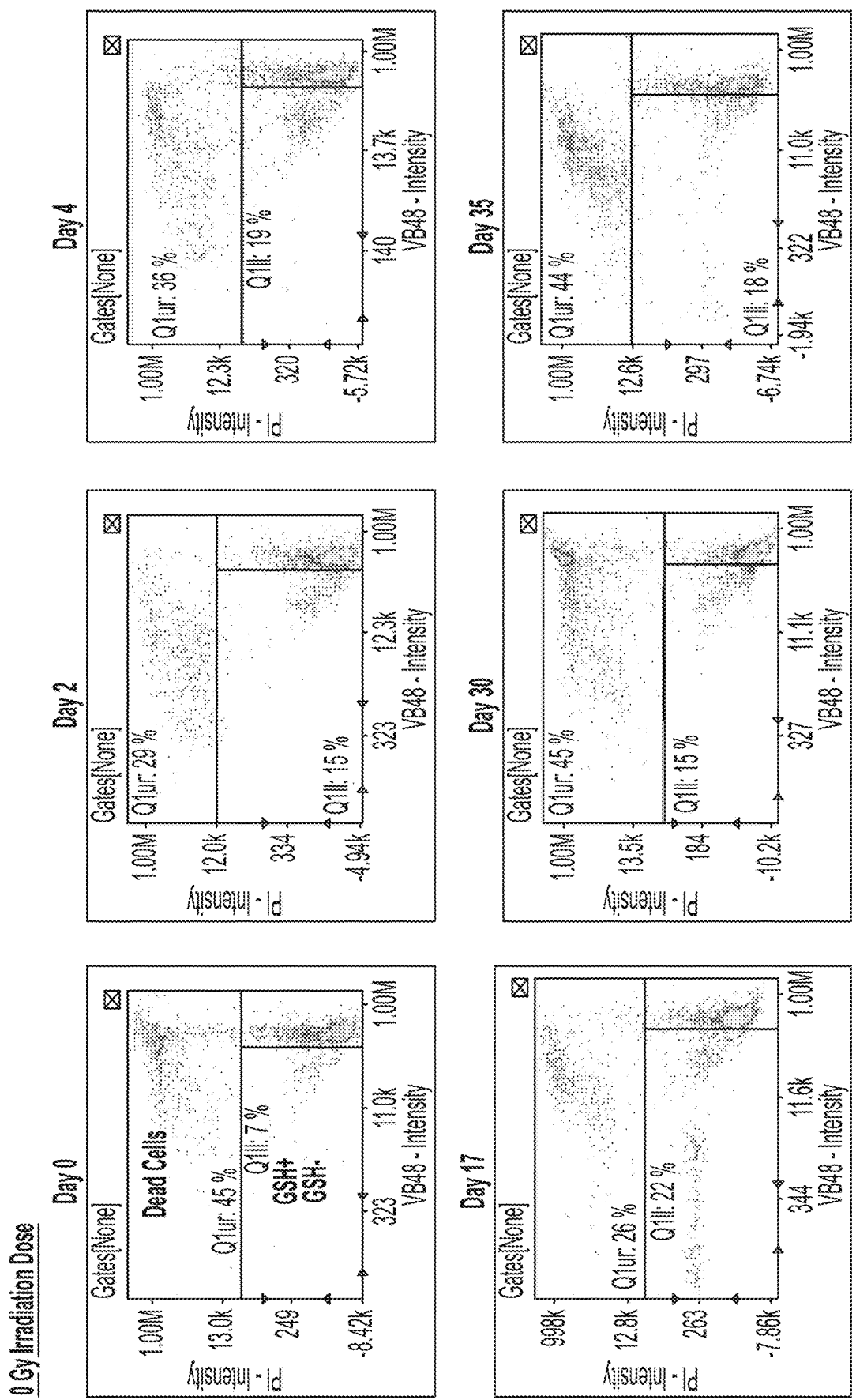
FIG. 7B shows cytometry images from a glutathione (GSH) Vitality Assay of PD-L1 t-haNK cells at Day 0, 2, 4, 17, 30, and 35 after 0, 2.5, 5, 10, 15, 20, or 30 Gy radiation, as indicated.
Figure 7B:
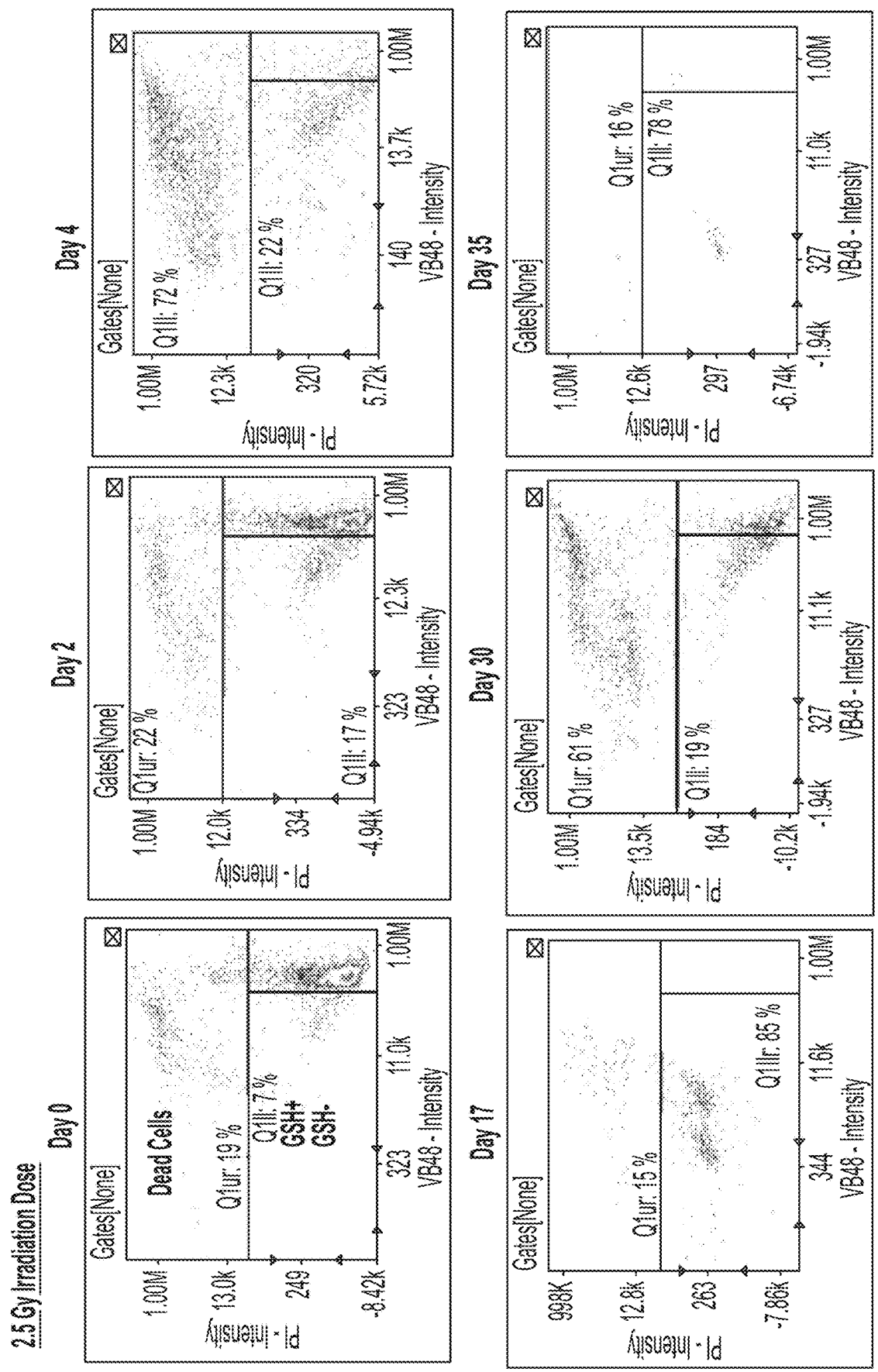
Figure 7B:
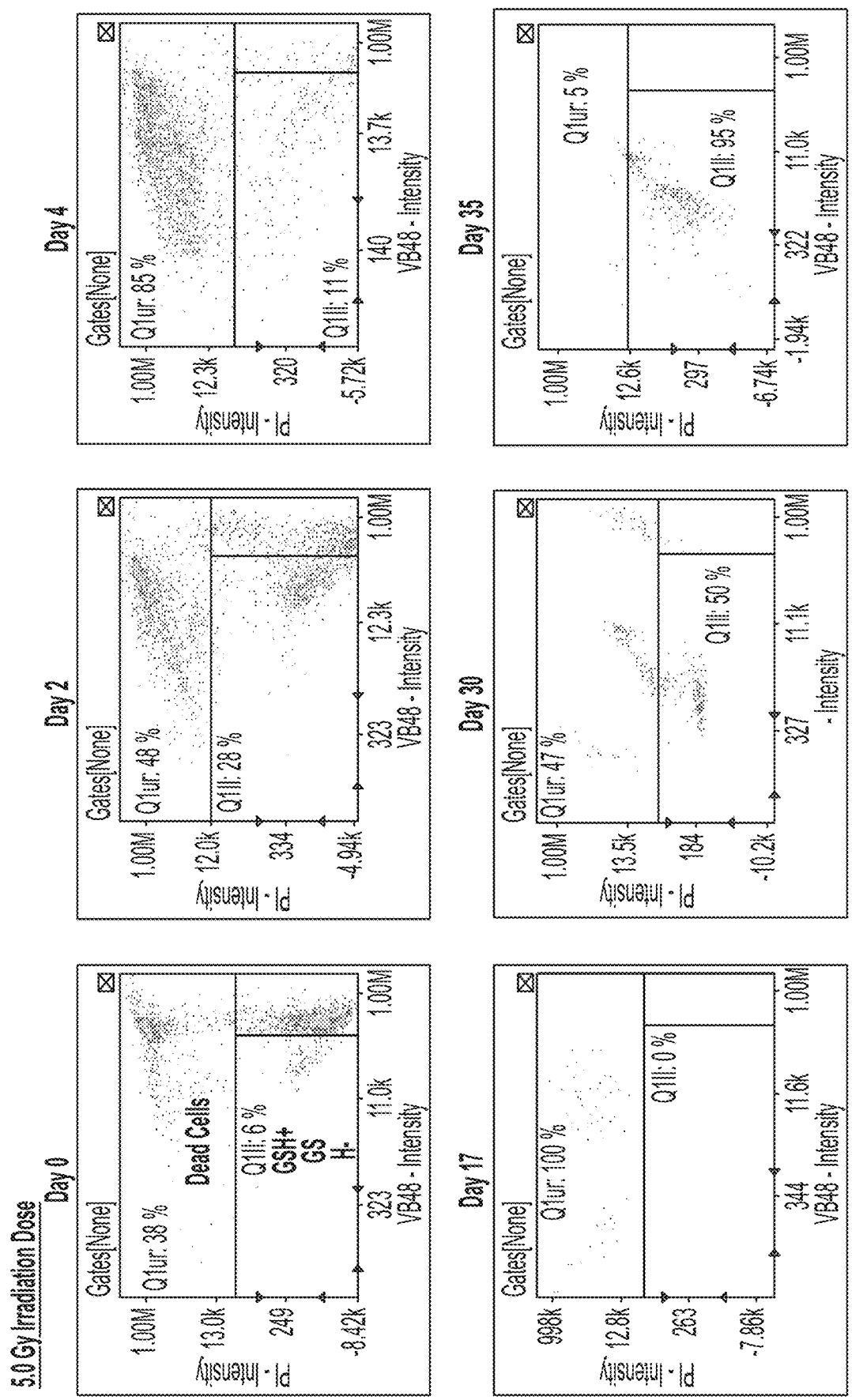
Figure 7B:
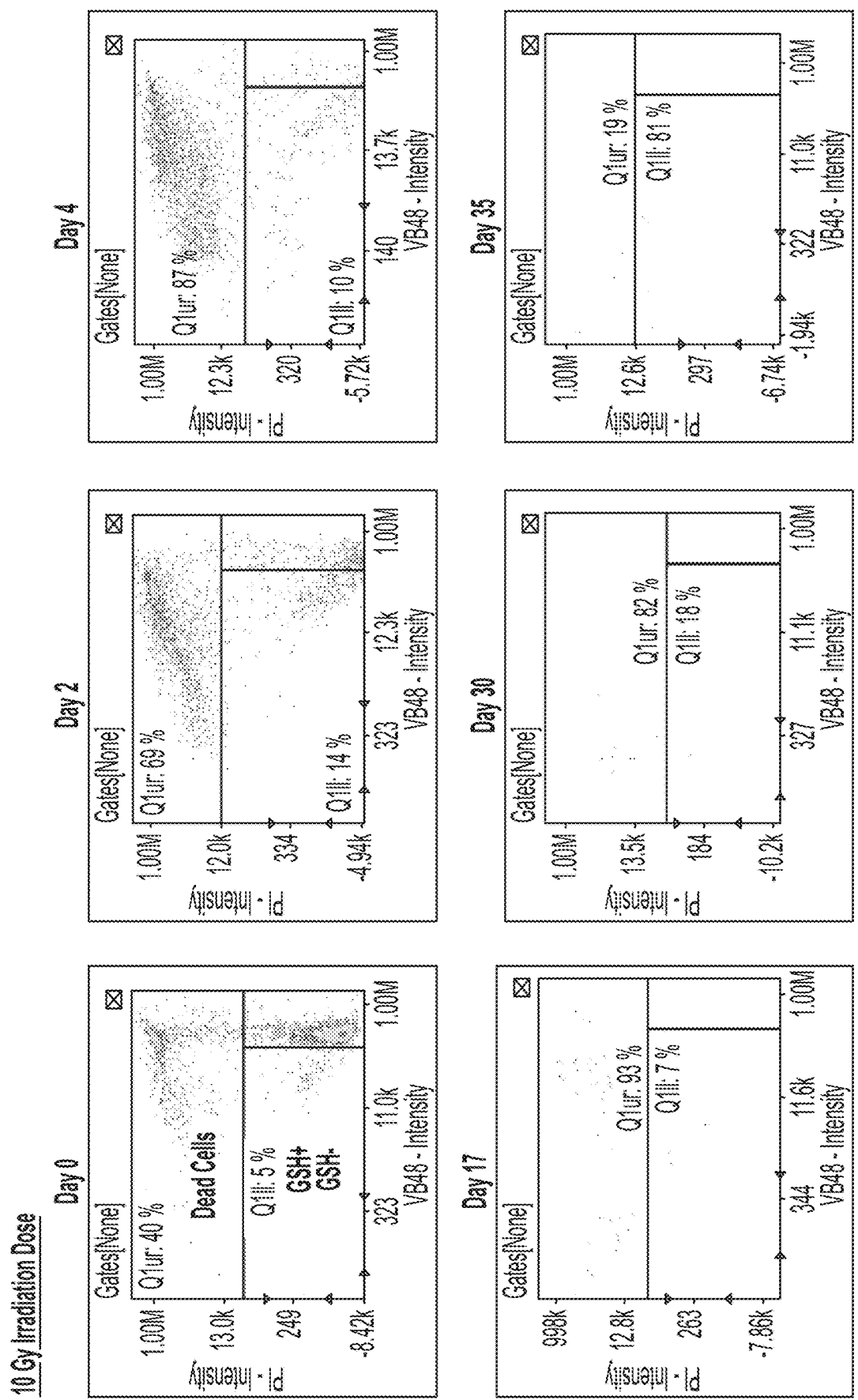
Figure 7B:
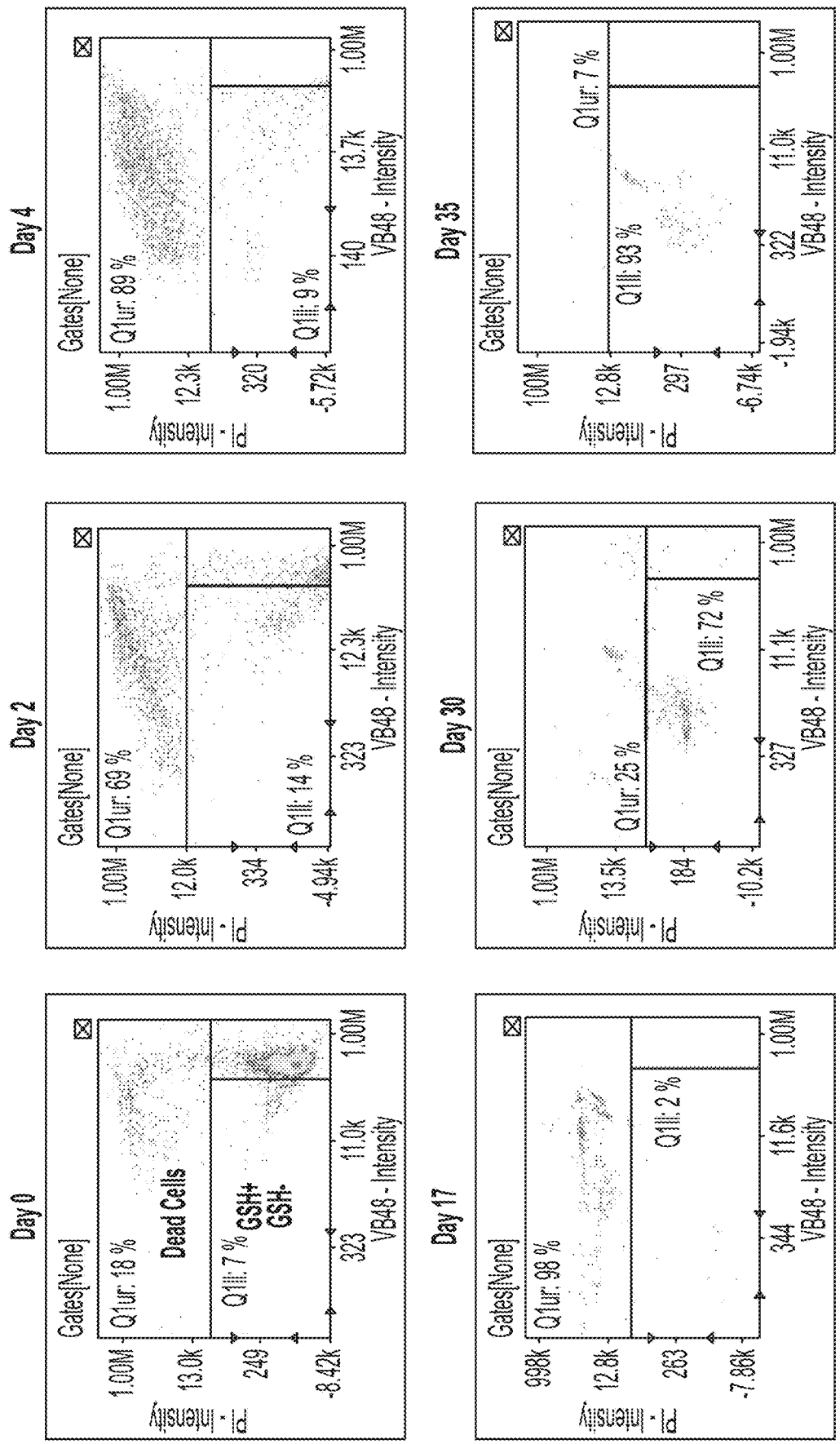
Figure 7B:
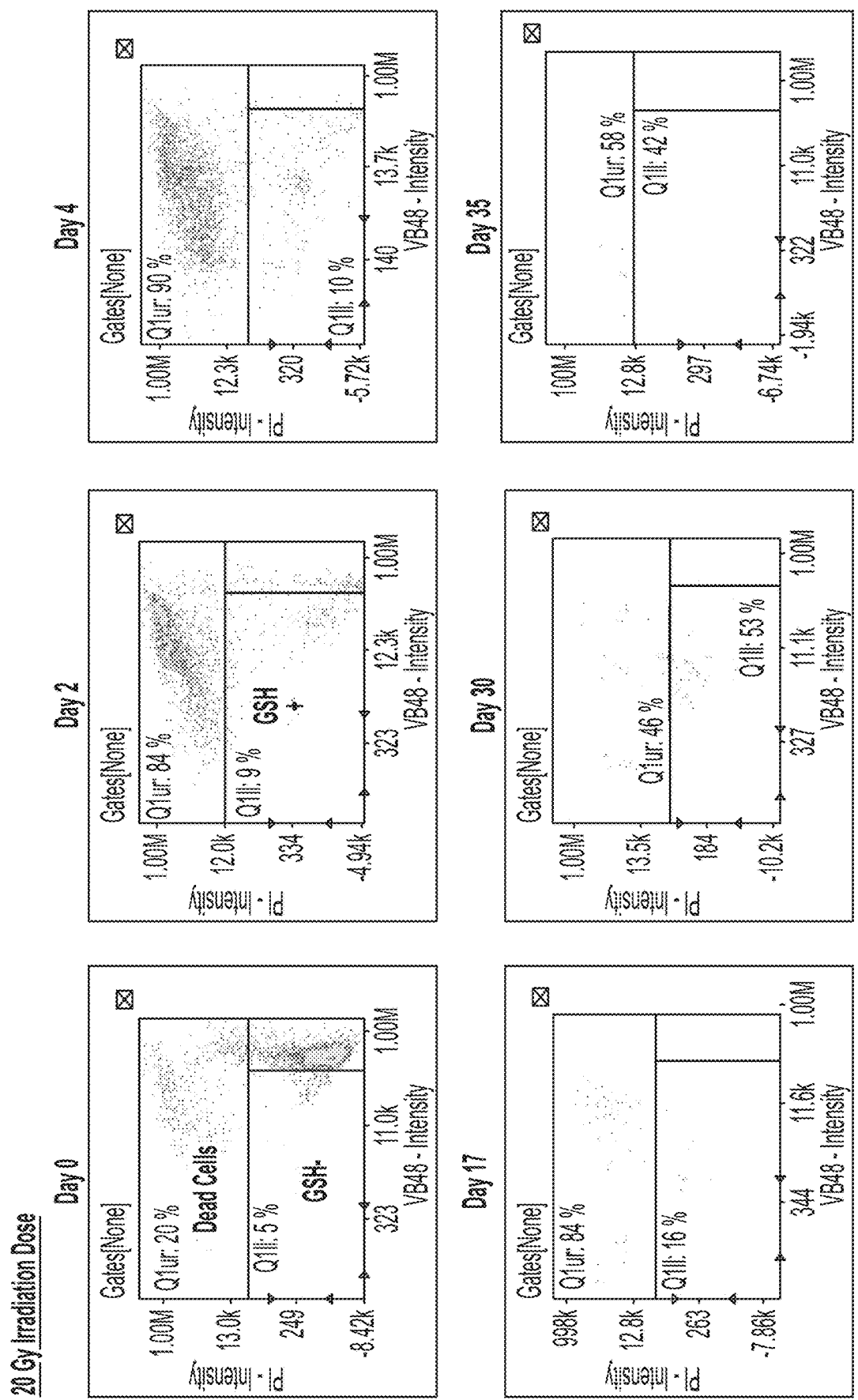
Figure 7B:
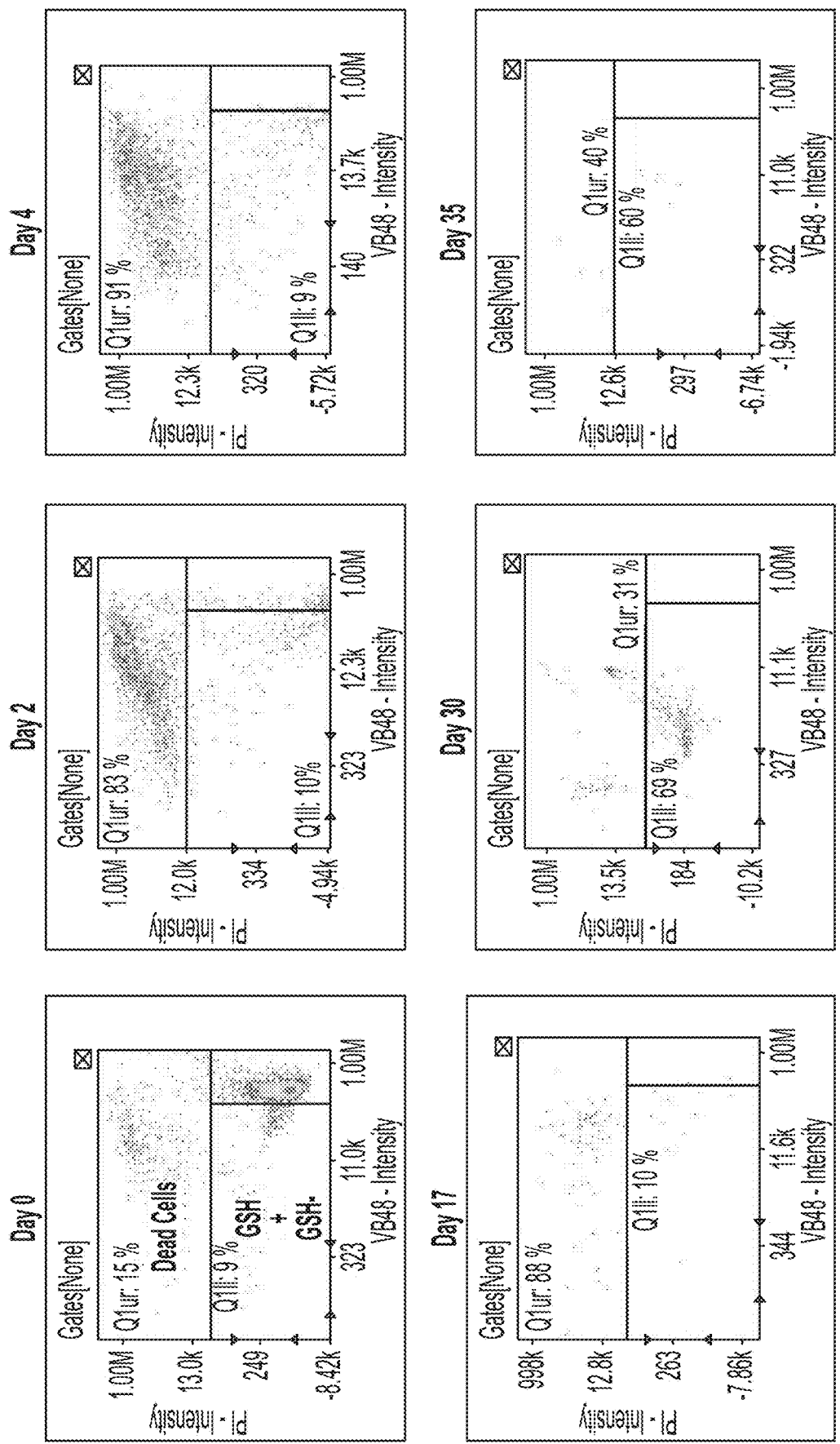

To evaluate the impact of irradiation on cell proliferative capacity, cell health (cell vitality) and viability was monitored over 35 days of culture. With reference to FIGS. 6, 7A, and 7B, samples were taken from the flasks on Days 1, 2, 3, 4, 7, 10, 15, 21, 28 and 35 and analytical testing was performed to measure; (a) cell viability and viable cell count by CCV NC-200 test method; (b) cell morphology by bright field microscopy and (c) cell health using NucleoCounter® NC3000™ image cytometer. Nonirradiated cells were used as study control.

Pd-L1 t-Hank Cell Growth Analysis Post Irradiation

Cell viability and viable cell counts were determined by CCV NC-200 test method. In the flask containing the irradiated cells, the viable cell density (VCD) of the cells significantly decreased from the initial $5 \times 10^5$ cells/mL by day 7 of culture while the numbers in non-irradiated flask showed a rapid outgrowth within seven days (FIGS. 5A-5B). No cell growth was observed in any of the flasks containing cells irradiated with approximately 5 Gy dose of irradiation for up to 35 days.

Cell counts by CCV NC-200 test method were further confirmed by brightfield imaging using EVOS microscope. Visualization of cell morphology during the culture period confirmed a significant decline in cell numbers in irradiated flasks by day 9 (FIG. 6) and no live cells were observed from day 15 till the end of the study.

In the Annexin assay, cells are stained using fluorescently labeled Annexin V and Propidium Iodide (PI), the latter to distinguish between the early and late apoptotic/necrotic cells. Culture cell health was evaluated by Annexin V staining using the imaging cytometry by NucleoCounter® NC3000™. Annexin V staining in combination with Hoeschst 33342 and Propidium Iodide (PI) showed an increase in number of apoptotic (Annexin+PI+, upper right quadrants) and pre-apoptotic (Annexin+PI−, lower right quadrants) cells after two days of culture in flasks irradiated with 2.5 Gy dose of irradiation and above (FIG. 7A).

Pd-L1 t-Hank Cell Health Evaluation Using Vitality Assay

Cell vitality was measured by detecting changes in levels of intracellular reduced thiols (glutathione; GSH), which is an early hallmark of cells death progression. The cell health in culture was evaluated by Vitality Assay using the imaging cytometry by NucleoCounter® NC3000™. A significant decrease in cellular GSH concentration (GSH+, lower right quadrants) and increase in PI positive dead cells (upper quadrants) was observed in flasks irradiated with 2.5 Gy dose of irradiation and above after two days of culture (FIG. 7B).

The objectives of this study were to assess the effect of different doses of X-ray irradiation on proliferative capacity of PD-LI t-haNK cells. These results collectively demonstrate that RS-2000 irradiator programmed at 15 Gy dose can prevent proliferative capacity of PD-LI t-haNK cells. However, no cell growth was observed when cultures were irradiated in the range of 5 to 30 Gy X-ray irradiation dose. The non-irradiated cells (control sample) were able to grow in culture for up to 35 days.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A recombinant natural killer (NK)-92 cell transfected with a plasmid expression vector and gamma (γ)-irradiated, wherein the plasmid expression vector comprises a nucleic acid that encodes i) a homing receptor; ii) an antigen binding protein (ABP) or a chimeric antigen receptor (CAR) that specifically binds a target antigen; iii) an Fc Receptor; and iv) a secreted immune modulator, wherein the secreted immune modulator is a TGFβ inhibitor,
wherein the homing receptor is selected from the group consisting of a G protein-coupled receptor, a chemokine receptor, a cytokine receptor, a cell adhesion molecule, a selectin, and an integrin,
wherein the TGFβ inhibitor has the amino acid sequence of SEQ ID NO:64 or SEQ ID NO:66 and
wherein the nucleic acid is operably linked to a promoter.

2. The recombinant NK-92 cell of claim 1, wherein the recombinant NK-92 cell is irradiated at between 2.5 to 20 Gy.

3. The recombinant NK-92 cell of claim 1, wherein the modified NK-92 cell is irradiated at 5, 10, or 15 Gy.

4. The recombinant NK-92 cell of claim 1, wherein the nucleic acid is a quadricistronic vector.

5. The recombinant NK-92 cell of claim 1, wherein the antigen binding protein is selected from a protein or antibody that binds to CD19, CD20, GD2, HER-2, CD30, EGFR, FAP, CD33, CD123, PD-L1, IGF1R, CSPG4, or B7-H4.

6. The recombinant NK-92 cell of claim 1, wherein the antigen binding protein binds to PD-L1.

7. The recombinant NK-92 cell of claim 1, wherein the Fc Receptor is CD16 or a high affinity CD16.

8. The recombinant NK-92 cell of claim 1, wherein the CAR specifically binds PD-L1.

9. The recombinant NK-92 cell of claim 1, wherein the recombinant NK-92 cell has inhibited cell replication after exposure to the gamma radiation and wherein the secreted TGFβ inhibitor is transiently active up to about 72 hours.

10. A composition comprising the recombinant NK-92 cell of claim 1 and a pharmaceutically acceptable excipient.

11. A kit comprising the recombinant NK-92 cell of claim 1 and instructions for use.

* * * * *